United States Patent
Chenard et al.

(10) Patent No.: US 9,447,114 B2
(45) Date of Patent: Sep. 20, 2016

(54) THIENO- AND FURO[2,3-D]PYRIMIDINE-2,4[1H,3H]-DIONE DERIVATIVES

(71) Applicant: Hydra Biosciences, Inc., Cambridge, MA (US)

(72) Inventors: Bertrand L. Chenard, Waterford, CT (US); Randall J. Gallaschun, Lebanon, CT (US)

(73) Assignee: Hydra Biosciences, Inc., Cambridge, MA (US)

( * ) Notice: Subject to any disclaimer, the term of this patent is extended or adjusted under 35 U.S.C. 154(b) by 0 days.

(21) Appl. No.: 14/822,018

(22) Filed: Aug. 10, 2015

(65) Prior Publication Data

US 2016/0039841 A1     Feb. 11, 2016

Related U.S. Application Data

(60) Provisional application No. 62/035,575, filed on Aug. 11, 2014.

(51) Int. Cl.

| A61K 31/519 | (2006.01) |
|---|---|
| C07D 495/04 | (2006.01) |
| C07D 491/048 | (2006.01) |
| C07D 491/04 | (2006.01) |

(52) U.S. Cl.
CPC ........... C07D 495/04 (2013.01); C07D 491/04 (2013.01); C07D 491/048 (2013.01); A61K 31/519 (2013.01)

(58) Field of Classification Search
CPC .............. C07D 495/04; C07D 491/04; C07D 491/048
See application file for complete search history.

(56) References Cited

U.S. PATENT DOCUMENTS

| 4,536,518 | A * | 8/1985 | Welch, Jr. ............ C07C 43/21 514/555 |
|---|---|---|---|
| 2012/0041004 | A1* | 2/2012 | Chaudhari ........... A61K 31/519 514/462.1 |
| 2012/0178766 | A1* | 7/2012 | Chaudhari ........... C07D 495/04 514/260.1 |
| 2015/0111038 | A1* | 4/2015 | Kadam ................ C07D 495/04 428/402 |
| 2015/0190366 | A1* | 7/2015 | Housley .............. A61K 31/352 514/6.5 |
| 2016/0046624 | A1* | 2/2016 | Chenard .............. C07D 471/04 514/264.1 |

FOREIGN PATENT DOCUMENTS

| JP | EP 0640606 A1 * | 3/1995 | ........... A61K 31/505 |
|---|---|---|---|
| WO | WO 02064572 A1 * | 8/2002 | ........... A64K 31/517 |
| WO | WO-2004028634 A1 | 4/2004 | |
| WO | WO-2008070529 A2 | 6/2008 | |
| WO | WO-2010017368 A2 | 2/2010 | |

OTHER PUBLICATIONS

CAS Registry No. 606122-61-6 (Entered STN: Oct. 17, 2003).*
CAS Registry No. 1497903-60-2 (Entered STN: Dec. 18, 2013).*
CAS Registry Nos. (Indexed 2012).*
CAS Registry Nos. (Indexed 2006).*
C. Hong et al., 138 Brain, 3030-3047 (2015).*
K.D. Phelan et al., 83 Molecular Pharmacology, 429-438 (2013).*
M. Raychaudhuri et al., 2011 International Journal of Alzheimer's Disease, 1-5 (2011).*
J. Richter et al., 171 British Journal of Pharmacology, 158-170 (2014).*
C-O Wong et al., 159 British Journal of Pharmacology, 1486-1496 (2010).*

* cited by examiner

*Primary Examiner* — Alexander R Pagano
(74) *Attorney, Agent, or Firm* — McCarter & English, LLP; Steven G. Davis; Kathryn M. Kizer

(57) ABSTRACT

This invention relates to novel Thieno- and Furo[2,3-d] pyrimidine-2,4[1H,3H]-dione derivatives of formula I

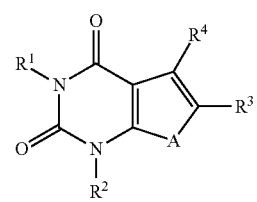

and their use as TRPC5 modulators, pharmaceutical compositions containing the same, and methods of using the same as agents for the treatment of TRPC5 receptor mediated disorders or conditions. A, $R^1$, $R^2$, $R^3$ and $R^4$ have meanings given in the description.

15 Claims, No Drawings

THIENO- AND FURO[2,3-D]PYRIMIDINE-2,4[1H,3H]-DIONE DERIVATIVES

RELATED APPLICATIONS

The present application is a U.S. Non-Provisional Application which claims priority to U.S. Provisional Patent Application No. 62/035,575, filed Aug. 11, 2014, the entirety of which applications is hereby incorporated herein by reference.

FIELD OF THE INVENTION

This invention relates to novel Thieno- and Furo[2,3-d]pyrimidine-2,4[1H,3H]-dione derivatives and their use as TRPC5 modulators, pharmaceutical compositions containing the same, and methods of using the same as agents for the treatment of TRPC5 receptor mediated disorders or conditions.

BACKGROUND

A variety of ion channel proteins exist to mediate ion flux across cellular membranes. The proper expression and function of ion channel proteins is essential for the maintenance of cell function, intracellular communication, and the like. Numerous diseases are the result of misregulation of membrane potential or aberrant calcium handling. Given the central importance of ion channels in modulating membrane potential and ion flux in cells, identification of agents that can promote or inhibit particular ion channels are of great interest as research tools and as possible therapeutic agents.

Cation channels such as TRPC5 modulate the flux of calcium and sodium ions across cellular membranes. Sodium and calcium influx leads to a depolarization of the cell. This increases the probability that voltage-gated ion channels will reach the threshold required for activation. As a result, activation of non-selective cation channels can increase electrical excitability and increase the frequency of voltage-dependent events. Voltage-dependent events include, but are not limited to, neuronal action potentials, cardiac action potentials, smooth muscle contraction, cardiac muscle contraction, and skeletal muscle contraction.

Calcium influx caused by the activation of non-selective cation channels such as TRPC5 also alters the intracellular free calcium concentration. Calcium is a ubiquitous second messenger molecule within the cell and the alterations in intracellular calcium levels have profound effects on signal transduction and gene expression. Thus, activation of non-selective cation channels such as TRPC5 can lead to changes in gene expression and cellular phenotype. Gene expression events include, but are not limited to, production of mRNAs encoding cell surface receptors, ion channels, and kinases. These changes in gene expression can lead to hyperexcitability in that cell.

Transient receptor potential (TRP) homomeric TRPC5 ion channels are signal transduction gated, $Ca^{2+}$-permeable channels predominantly expressed in the neurons. TRPC5 forms homomultimeric structures such as tetramers (i.e., TRPC5 homomultimers) and heteromultimeric structures such as tetramers (i.e., TRPC5-TRPC1 heteromultimers). Unless expressly stated otherwise, when the term TRPC5 is used herein, for example, when identifying a modulator of TRPC5 such as a TRPC5 antagonist, the term TRPC5 is used generically so as to include either or both of a TRPC5 homomultimer or a heteromultimer (e.g., TRPC5-TPRC1 or TRPC5-TRPC4 heteromultimer). Examples of TRPC5 in the literature include the following: Nature. 2008 Jan. 3; 451 (7174):69-72; Mol Pharmacol. 2008 January; 73 (1):42-9; J Biol Chem. 2007 Nov. 16; 282 (46):33868-78; Biochem Biophys Res Commun. 2008 Jan. 11; 365 (2):239-45; J Biol Chem. 2006 Nov. 3; 281 (44):33487-96; Eur J Pharmacol. 2005 Mar. 14; 510 (3):217-22; J Biol Chem. 2006 Feb. 24; 281 (8):4977-82; Biochem Soc Trans. 2007 February; 35 (Pt 1):101-4; Handb Exp Pharmacol. 2007; (179):109-23; J Biol Chem. 2005 Mar. 25; 280 (12):10997-1006; J Physiol. 2006 Jan. 15; 570 (Pt 2):219-35; and Nat Neurosci. (2003) 6: 837-45.

Modulating the function of TRPC5 proteins provides a means of modulating calcium homeostasis, sodium homeostasis, membrane polarization, and/or intracellular calcium levels, and compounds that can modulate TRPC5 function are useful in many aspects, including, but not limited to, maintaining calcium homeostasis, modulating intracellular calcium levels, modulating membrane polarization, and treating or preventing diseases, disorders, or conditions associated with calcium and/or sodium homeostasis or dyshomeostasis.

SUMMARY OF THE INVENTION

The present invention provides compounds of Formula (I):

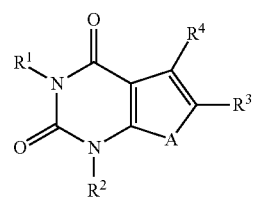

Formula (I)

or a pharmaceutically acceptable salt thereof, wherein constituent members are provided herein.

The present invention further provides compositions comprising a compound of Formula (I) and a pharmaceutically acceptable carrier.

The present invention further provides methods of treating a TRPC5 mediated disorder in a subject, e.g. a human subject, comprising administering to the subject a compound or composition of a compound of Formula (I) or a pharmaceutically acceptable salt thereof, to thereby treat the subject, e.g., a human subject.

The present invention provides methods and compositions for treating conditions such as a neuropsychiatric disorder, a neurodegenerative disorder, nephropathy, and seizure disorder by modulating the activity of the transient receptor potential cation channel subfamily C, member 5 (TRPC5), which can exist in homomultimeric form as well as heteromultimeric form with other ion channels such as TRPC1 or TRPC3 (i.e., TRPC5-TRPC1 and TRPC1-TRPC3-TRPC5). The compound of Formula (I) modulate the function of TRPC5 by inhibiting a TRPC5-mediated ion flux or by inhibiting the inward current, the outward current, or both currents mediated by TRPC5. The inhibition of a particular current is the ability to inhibit or reduce such current (e.g., inward and/or outward) in an in vitro or an in vivo assay. The activation of a particular current is the ability to activate or increase such current (e.g., inward and/or outward) in an in vitro or an in vivo assay.

DETAILED DESCRIPTION OF THE INVENTION

The present invention provides a compound of Formula (I):

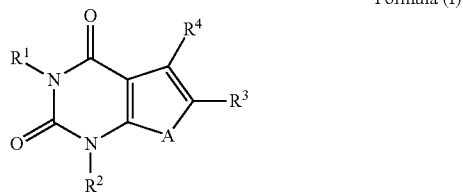

Formula (I)

or a pharmaceutically acceptable salt thereof, wherein:

A is S or O;

$R^1$ is $C_2$-$C_{10}$ hydroxyalkyl, optionally substituted with 1-3 $R^5$;

$R^2$ is H, $C_1$-$C_6$ alkyl, $C_1$-$C_6$ hydroxyalkyl, $C_3$-$C_{10}$ cycloalkyl, $C_2$-$C_6$ alkenyl, $C_2$-$C_6$ alkynyl, or $C_1$-$C_6$ alkoxy;

$R^3$ is $C_1$-$C_6$ alkyl, $C_2$-$C_6$ alkenyl, $C_2$-$C_6$ alkynyl, $C_1$-$C_6$ acyl, $C_3$-$C_{10}$ cycloalkyl, $C_1$-$C_6$ alkoxy, $C_4$-$C_{10}$ cycloalkyloxy, halo, $C_1$-$C_6$ haloalkyl, $C_1$-$C_6$ haloalkoxy, hydroxyl, alkylthio, thionyl, sulfonyl, sulfonamidyl, $C_6$-$C_{12}$ aryl, 5-14-membered heteroaryl, $C_6$-$C_{12}$ aryl-$C_1$-$C_6$ alkyl, 5-14-membered heteroaryl-$C_1$-$C_6$ alkyl, $C_6$-$C_{12}$ aryloxy, —O—$C_6$-$C_{12}$ aryl-$C_1$-$C_6$ alkyl, —O— $C_1$-$C_6$ alkyl-$C_6$-$C_{12}$ aryl, —$C_6$-$C_{12}$ aryl-$C_1$-$C_6$ alky-O, 5-14-membered heteroaryloxy, 3-18-membered heterocycloalkyl, amino, $C_1$-$C_6$ alkylamino, $C_2$-$C_{12}$ dialkylamino, —C(O)NH—, —C(O)N—C)N—$C_6$ alkyl-, —NHC(O)—, —N—$C_1$-$C_6$ alkyl C(O)—, urea, sulfonylurea, nitro, cyano, each of which is optionally substituted with 1-4 $R^5$;

$R^4$ is $C_1$-$C_6$ alkyl, $C_2$-$C_6$ alkenyl, $C_2$-$C_6$ alkynyl, $C_1$-$C_6$ acyl, $C_3$-$C_{10}$ cycloalkyl, $C_1$-$C_6$ alkoxy, $C_4$-$C_{10}$ cycloalkyloxy, halo, $C_1$-$C_6$ haloalkyl, $C_1$-$C_6$ haloalkoxy, hydroxyl, alkylthio, thionyl, sulfonyl, sulfonamidyl, $C_6$-$C_{12}$ aryl, 5-14-membered heteroaryl, $C_6$-$C_{12}$ aryl-$C_1$-$C_6$ alkyl, 5-14-membered heteroaryl-$C_1$-$C_6$ alkyl, $C_6$-$C_{12}$ aryloxy, —O—$C_6$-$C_{12}$ aryl-$C_1$-$C_6$ alkyl, —O— $C_1$-$C_6$ alkyl-$C_6$-$C_{12}$ aryl, —$C_6$-$C_{12}$ aryl-$C_1$-$C_6$ alky-O, 5-14-membered heteroaryl-$C_1$-$C_6$ alkyl, 5-14-membered heteroaryloxy, 3-18-membered heterocycloalkyl, amino, $C_1$-$C_6$ alkylamino, $C_2$-$C_{12}$ dialkylamino, —C(O)NH—, —C(O)N—$C_1$-$C_6$ alkyl-, —NHC(O)—, —N—$C_1$-$C_6$ alkyl C(O)—, urea, sulfonylurea, nitro, cyano, each of which is optionally substituted with 1-4 $R^5$;

each $R^5$ is independently $C_1$-$C_6$ alkyl, $C_2$-$C_6$ alkenyl, $C_2$-$C_6$ alkynyl, $C_1$-$C_6$ acyl, $C_3$-$C_{10}$ cycloalkyl, $C_1$-$C_6$ alkoxy, $C_4$-$C_{10}$ cycloalkyloxy, halo, $C_1$-$C_6$ haloalkyl, $C_1$-$C_6$ haloalkoxy, hydroxyl, alkylthio, thionyl, sulfonyl, sulfonamidyl, amino, $C_1$-$C_6$ alkylamino, $C_2$-$C_{12}$ dialkylamino, keto, —C(O)NH—, —C(O)N—$C_1$-$C_6$ alkyl-, —NHC(O)—, —N—$C_1$-$C_6$ alkyl C(O)—, urea, sulfonylurea, nitro, cyano, each of which is optionally substituted with 1-5 $R^6$; and each $R^6$ is independently $C_1$-$C_6$ alkyl, $C_2$-$C_6$ alkenyl, $C_2$-$C_6$ alkynyl, $C_1$-$C_6$ acyl, $C_1$-$C_6$ alkoxy, halo, $C_1$-$C_6$ haloalkyl, $C_1$-$C_6$ haloalkoxy, hydroxyl, amino, —C(O)NH—, —C(O)N—$C_1$-$C_6$ alkyl-, —NHC(O)—, —N—$C_1$-$C_6$ alkyl C(O)—, nitro, or cyano.

In a second embodiment, in the general formula I, $R^2$, $R^3$, $R^4$, $R^5$, $R^6$ and A have the same meaning as defined the preceding embodiment and $R^1$ is $C_2$-$C_6$ hydroxyalkyl; or a pharmaceutically acceptable salt thereof.

In another embodiment, in the general formula I, $R^2$, $R^3$, $R^4$, $R^5$, $R^6$ and A have the same meaning as defined in any of the preceding embodiments and $R^1$ is 3-hydroxypropyl; or a pharmaceutically acceptable salt thereof.

In another embodiment, in the general formula I, $R^1$, $R^3$, $R^4$, $R^5$, $R^6$ and A have the same meaning as defined in any of the preceding embodiments and $R^2$ is $C_1$-$C_4$ alkyl or $C_1$-$C_4$ hydroxyalkyl; or a pharmaceutically acceptable salt thereof.

In another embodiment, in the general formula I, $R^1$, $R^3$, $R^4$, $R^5$, $R^6$ and A have the same meaning as defined in any of the preceding embodiments and $R^2$ is methyl or 3-hydroxypropyl; or a pharmaceutically acceptable salt thereof.

In another embodiment, in the general formula I, $R^1$, $R^2$, $R^3$, $R^4$, $R^5$, and $R^6$ have the same meaning as defined in any of the preceding embodiments and A is O; or a pharmaceutically acceptable salt thereof.

In another embodiment, in the general formula I, $R^1$, $R^2$, $R^3$, $R^4$, $R^5$, and $R^6$ have the same meaning as defined in any of the preceding embodiments and A is S; or a pharmaceutically acceptable salt thereof.

In another embodiment, in the general formula I, A, $R^1$, $R^2$, and $R^4$ have the same meaning as defined in any of the preceding embodiments and $R^3$ is $C_2$-$C_4$ alkyl, phenyl, pyridyl, phenoxy, which the latter three groups are optionally substituted with one or more substituents selected from phenyl, halogen or —OCF$_3$; or a pharmaceutically acceptable salt thereof.

In another embodiment, in the general formula I, A, $R^1$, $R^2$, and $R^3$ have the same meaning as defined in any of the preceding embodiments and $R^4$ is $C_1$-$C_5$ alkyl, $C_2$-$C_5$ acyl, or benzyl, each group optionally substituted with one or more methyl, hydroxyl, or halogens; or a pharmaceutically acceptable salt thereof.

In another embodiment, in the general formula I, A, $R^1$, $R^2$, and $R^4$ have the same meaning as defined in any of the preceding embodiments and $R^3$ is

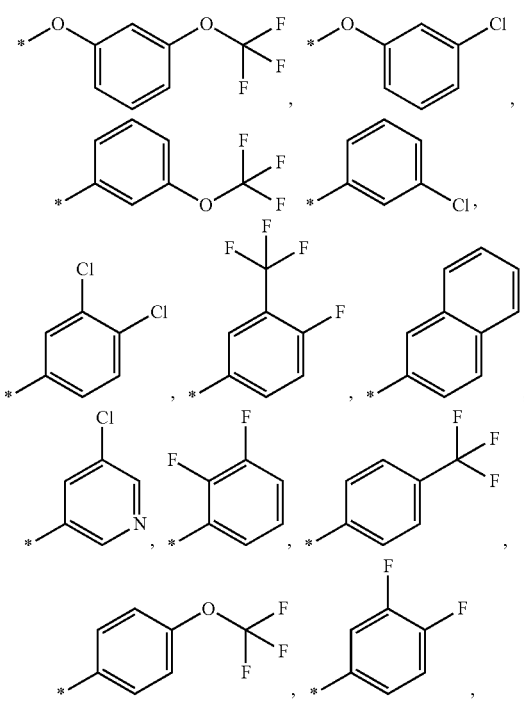

-continued

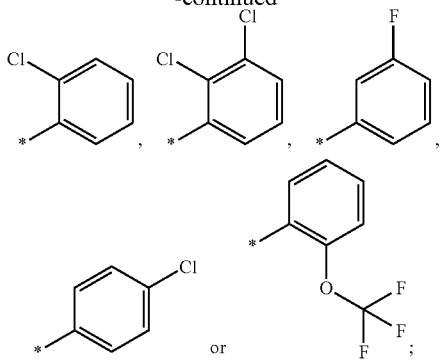

or pharmaceutically acceptable salt thereof.

In another embodiment, in the general formula I, A, $R^1$, $R^2$, and R have the same meaning as defined in any of the preceding embodiments and $R^4$ is methyl,

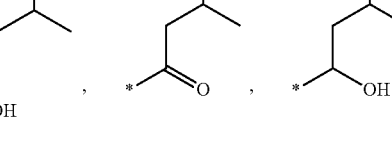

or a pharmaceutically acceptable salt thereof.

In another embodiment, in the general formula I, $R^1$, $R^2$, $R^3$, $R^4$, $R^5$, $R^6$ and A have the same meaning as defined in any of the preceding embodiments and, namely a compound of formula Ia or Ib

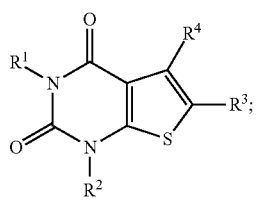

Ia

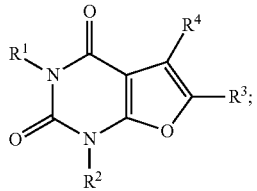

Ib in which
$R^1$ is 3-hydroxypropyl;
$R^2$ is methyl or 3-hydroxypropyl;

$R^3$ is

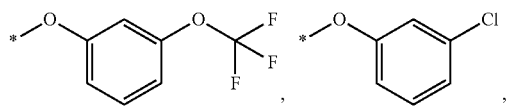

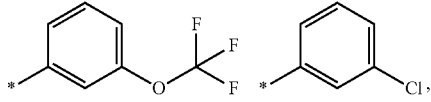

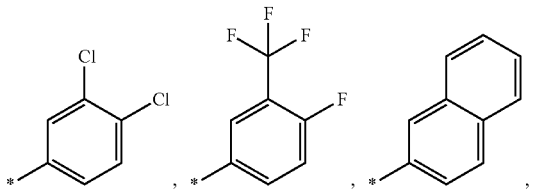

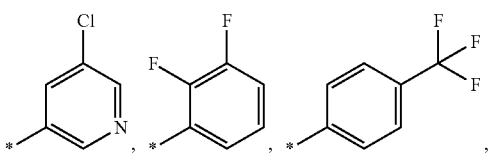

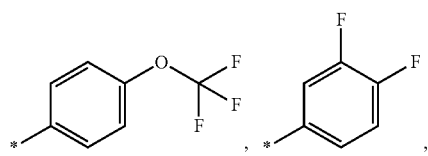

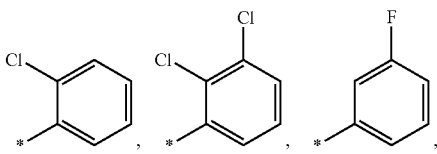

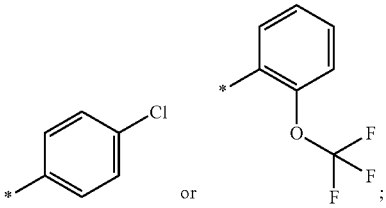

and
$R^4$ is methyl,

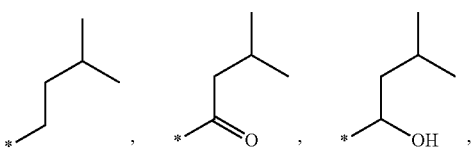

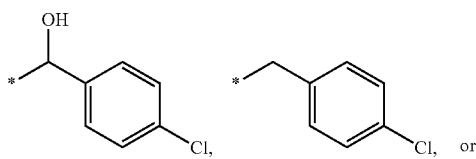
or a pharmaceutically acceptable salt thereof.
In certain embodiments, exemplary compounds of Formula (I) include the compounds described in Table 1 and in the Examples.
TABLE 1
| Compound Number | Structure |
| --- | --- |
| 1 | 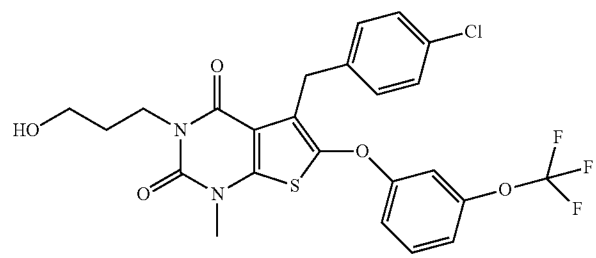 [SMILES: Cn1c(=O)n(CCCO)c(=O)c2c(Cc3ccc(Cl)cc3)c(Oc3cccc(OC(F)(F)F)c3)sc21] |
| 2 | 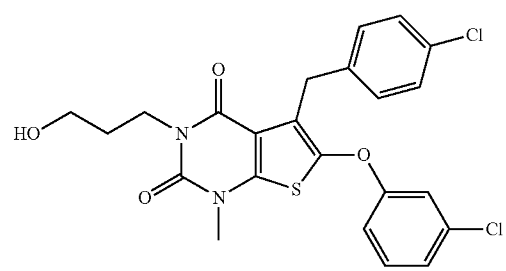 [SMILES: Cn1c(=O)n(CCCO)c(=O)c2c(Cc3ccc(Cl)cc3)c(Oc3cccc(Cl)c3)sc21] |
| 3 | 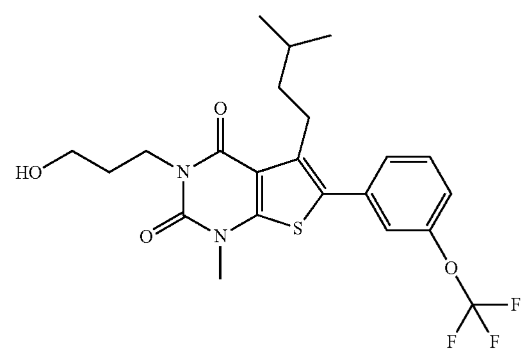 [SMILES: CC(C)CCc1c(-c2cccc(OC(F)(F)F)c2)sc2c1c(=O)n(CCCO)c(=O)n2C] |
| 4 | 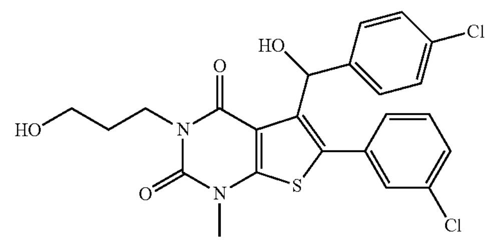 [SMILES: Cn1c(=O)n(CCCO)c(=O)c2c(C(O)c3ccc(Cl)cc3)c(-c3cccc(Cl)c3)sc21] |

TABLE 1-continued

| Compound Number | Structure |
|---|---|
| 5 | 3-(3-hydroxypropyl)-1,5-dimethyl-6-(3,4-dichlorophenyl)thieno[2,3-d]pyrimidine-2,4(1H,3H)-dione |
| 6 | 3-(3-hydroxypropyl)-1,5-dimethyl-6-(4-fluoro-3-(trifluoromethyl)phenyl)thieno[2,3-d]pyrimidine-2,4(1H,3H)-dione |
| 7 | 3-(3-hydroxypropyl)-1,5-dimethyl-6-(naphthalen-2-yl)thieno[2,3-d]pyrimidine-2,4(1H,3H)-dione |
| 8 | 3-(3-hydroxypropyl)-1,5-dimethyl-6-(5-chloropyridin-3-yl)thieno[2,3-d]pyrimidine-2,4(1H,3H)-dione |
| 10 | 3-(3-hydroxypropyl)-1,5-dimethyl-6-(2,3-difluorophenyl)thieno[2,3-d]pyrimidine-2,4(1H,3H)-dione |
| 11 | 3-(3-hydroxypropyl)-1,5-dimethyl-6-(4-(trifluoromethyl)phenyl)thieno[2,3-d]pyrimidine-2,4(1H,3H)-dione |
| 12 | 3-(3-hydroxypropyl)-1,5-dimethyl-6-(4-(trifluoromethoxy)phenyl)thieno[2,3-d]pyrimidine-2,4(1H,3H)-dione |

TABLE 1-continued

| Compound Number | Structure |
|---|---|
| 13 | 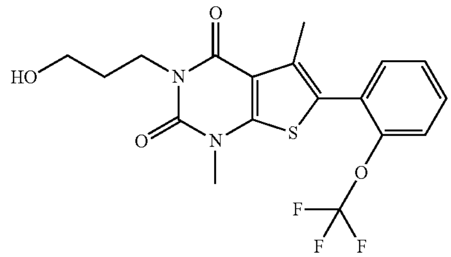 [SMILES: Cc1c(-c2ccccc2OC(F)(F)F)sc2c1c(=O)n(CCCO)c(=O)n2C] |
| 14 | 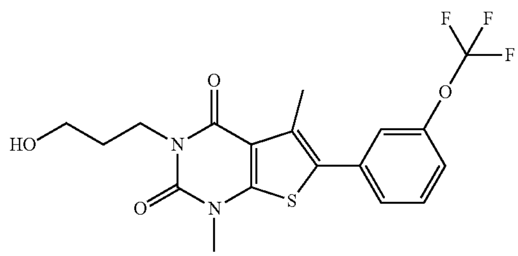 [SMILES: Cc1c(-c2cccc(OC(F)(F)F)c2)sc2c1c(=O)n(CCCO)c(=O)n2C] |
| 15 | 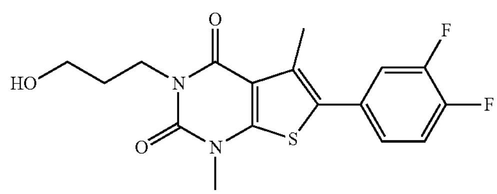 [SMILES: Cc1c(-c2ccc(F)c(F)c2)sc2c1c(=O)n(CCCO)c(=O)n2C] |
| 16 | 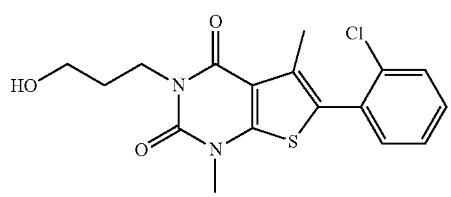 [SMILES: Cc1c(-c2ccccc2Cl)sc2c1c(=O)n(CCCO)c(=O)n2C] |
| 17 | 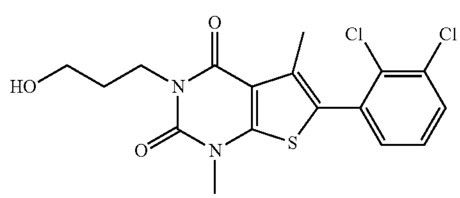 [SMILES: Cc1c(-c2cccc(Cl)c2Cl)sc2c1c(=O)n(CCCO)c(=O)n2C] |
| 18 | 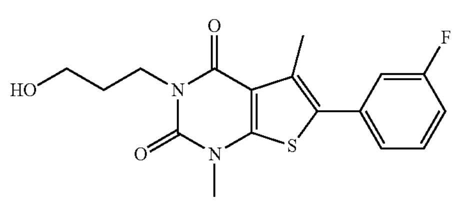 [SMILES: Cc1c(-c2cccc(F)c2)sc2c1c(=O)n(CCCO)c(=O)n2C] |
| 19 | 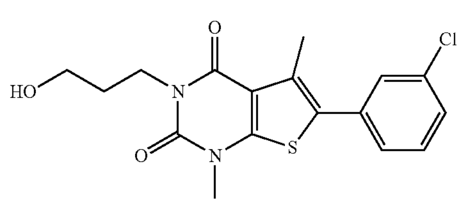 [SMILES: Cc1c(-c2cccc(Cl)c2)sc2c1c(=O)n(CCCO)c(=O)n2C] |

TABLE 1-continued
| Compound Number | Structure |
|---|---|
| 20 | 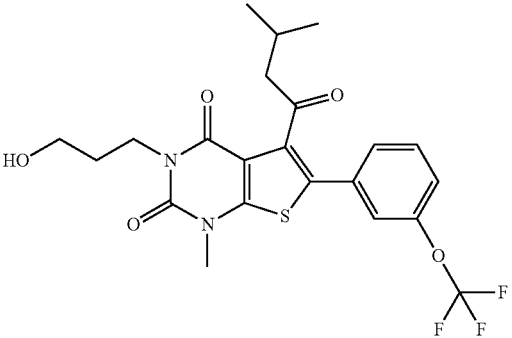 [SMILES: CC(C)CC(=O)c1c(-c2cccc(OC(F)(F)F)c2)sc2c1c(=O)n(CCCO)c(=O)n2C] |
| 21 | 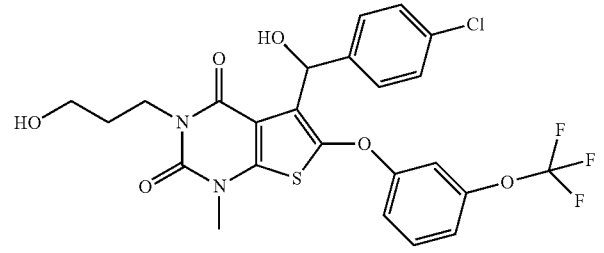 [SMILES: Cn1c(=O)n(CCCO)c(=O)c2c(C(O)c3ccc(Cl)cc3)c(Oc3cccc(OC(F)(F)F)c3)sc21] |
| 22 | 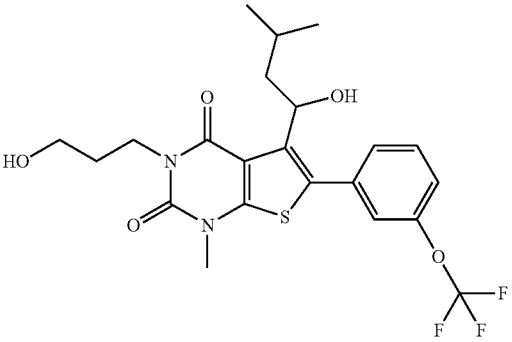 [SMILES: CC(C)CC(O)c1c(-c2cccc(OC(F)(F)F)c2)sc2c1c(=O)n(CCCO)c(=O)n2C] |
| 23 | 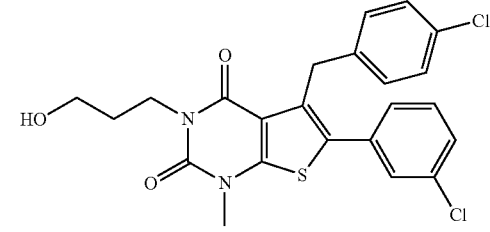 [SMILES: Cn1c(=O)n(CCCO)c(=O)c2c(Cc3ccc(Cl)cc3)c(-c3cccc(Cl)c3)sc21] |
| 24 | 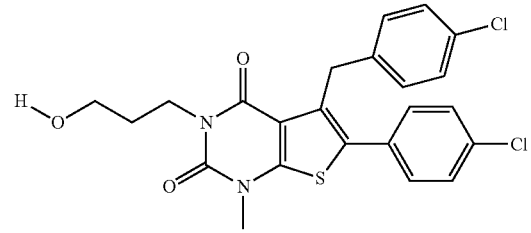 [SMILES: Cn1c(=O)n(CCCO)c(=O)c2c(Cc3ccc(Cl)cc3)c(-c3ccc(Cl)cc3)sc21] |

TABLE 1-continued

| Compound Number | Structure |
|---|---|
| 25 | *(structure)* |
| 26 | *(structure)* |
| 27 | *(structure)* |
| 28 | *(structure)* |

The present invention further provides compositions comprising a compound of Formula (I) and a pharmaceutically acceptable carrier.

The present invention further provides methods of treating a TRPC5 mediated disorder in a subject, e.g. a human subject, comprising administering to the subject a compound or composition of a compound of Formula (I) or a pharmaceutically acceptable salt thereof, to thereby treat the subject, e.g., a human subject.

The present invention provides methods and compositions for treating conditions such as a neuropsychiatric disorder, a neurodegenerative disorder, nephropathy, and seizure disorder by modulating the activity of the transient receptor potential cation channel subfamily C, member 5 (TRPC5), which can exist in homomultimeric form as well as heteromultimeric form with other ion channels such as TRPC1 or TRPC3 (i.e., TRPC5-TRPC1 and TRPC1-TRPC3-TRPC5). The compound of Formula (I) modulate the function of TRPC5 by inhibiting a TRPC5-mediated ion flux or by inhibiting the inward current, the outward current, or both currents mediated by TRPC5. The inhibition of a particular current is the ability to inhibit or reduce such current (e.g., inward and/or outward) in an in vitro or an in vivo assay. The activation of a particular current is the ability to activate or increase such current (e.g., inward and/or outward) in an in vitro or an in vivo assay.

In one aspect, the invention relates to a method for treating a condition for which reduced TRPC5 activity can reduce the severity of the condition, by administering a TRPC5 antagonist, such as a compound of Formula (I), that inhibits TRPC5-mediated current and/or TRPC5-mediated ion flux. Described in greater detail herein are compounds of Formula (I), which are TRPC5 antagonists that have a measured $IC_{50}$ for inhibition of TRPC5 of 10 nanomolar or less.

In certain embodiments, the compounds of Formula (I), which are TRPC5 antagonists inhibit one or both of inward and outward TRPC5-mediated currents with an $IC_{50}$ 10 nanomolar or less. In certain embodiments, the compounds of Formula (I) inhibit at least 95% of TRPC5-mediated current or TRPC5-mediated ion flux when administered at 1 micromolar or less.

In another aspect, compounds of Formula (I), which are TRPC5 antagonists, can be used to inhibit a function of TRPC5, for example a TRPC5-mediated current and/or a TRPC5-mediated ion flux. In some embodiments, compounds of Formula (I) can be used to inhibit a TRPC5 mediated current in vitro, for example in cells in culture. In other embodiments, compounds of Formula (I) can be used to inhibit a TRPC5 mediated current in vivo. In certain embodiments, compounds of Formula (I) inhibit both an inward and an outward TRPC5-mediated current.

Another aspect of the invention features a pharmaceutical preparation suitable for use in a human patient, or for veterinary use, comprising an effective amount of a compound of Formula (I) (or a salt thereof, or a solvate, hydrate, oxidative metabolite or prodrug of the compound or its salt), and one or more pharmaceutically acceptable excipients, diluents, or carriers. The invention further contemplates the use of compounds of Formula (I) in the manufacture of a medicament or pharmaceutical preparation to treat or reduce the symptoms of any of the diseases or conditions provided in the specification. The compounds of Formula (I) for use in treating a particular disease or condition can be formulated for administration via a route appropriate for the particular disease or condition.

Compounds of Formula (I) can be administered alone or in combination with another therapeutic agent. For instance, the compounds of Formula (I) can be administered conjointly with one or more of an anti-inflammatory agent, anti-acne agent, anti-wrinkle agent, anti-scarring agent, anti-psoriatic agent, anti-proliferative agent, anti-fungal agent, anti-viral agent, anti-septic agent, anti-migraine agent, keratolytic agent, or a hair growth inhibitor.

Compounds of Formula (I) can be administered topically, orally, transdermally, rectally, vaginally, parentally, intranasally, intrapulmonary, intraocularly, intravenously, intramuscularly, intraarterially, intrathecally, intracapsularly, intraorbitally, intracardiacly, intradermally, intraperitoneally, transtracheally, subcutaneously, subcuticularly, intraarticularly, subcapsularly, subarachnoidly, intraspinally, intrasternally, sublingually, or by inhalation.

In some embodiments, compounds of Formula (I) can be administered topically.

In some embodiments, compounds of Formula (I) can be administered orally.

In some embodiments, compounds of Formula (I) can be administered parentally.

DEFINITIONS

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

For compounds of the invention in which a variable appears more than once, each variable can be a different moiety selected from the Markush group defining the variable. For example, where a structure is described having two R groups that are simultaneously present on the same compound; the two R groups can represent different moieties selected from the Markush group defined for R.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination. Compounds may be depicted by both chemical name and structure and in the event of conflict between the two the structure controls.

As used herein, "acyl" refers to the group ($C_1$-$C_6$ alkyl)-C(O)—.

As used herein, "alkyl," by itself or as part of another substituent, means, unless otherwise stated, a straight or branched chain, and can have a number of carbon atoms optionally designated (i.e., $C_1$-$C_6$ means one to six carbons). Examples of saturated hydrocarbon groups include, but are not limited to, groups such as methyl, ethyl, n-propyl, isopropyl, n-butyl, t-butyl, isobutyl, sec-butyl, n-pentyl, isopentyl, homologs and isomers of, for example, n-pentyl, n-hexyl, and the like.

As used herein, "alkenyl" can be a straight or branched hydrocarbon chain, containing at least one double bond, and having from two to six carbon atoms (i.e., $C_2$-$C_6$ alkenyl). Examples of alkenyl groups, include, but are not limited to, groups such as ethenyl (i.e., vinyl), prop-1-enyl (i.e., allyl), but-1-enyl, pent-1-enyl, penta-1,4-dienyl, and the like.

As used herein, "alkynyl" can be a straight or branched hydrocarbon chain, containing at least one triple bond, having from two to six carbon atoms (i.e., $C_2$-$C_6$ alkynyl). Examples of alkynyl groups, include, but are not limited to, groups such as ethynyl, propynyl, butynyl, pentynyl, hexynyl, and the like.

As used herein, "alkoxy" can be a straight chain or branched alkoxy group having from one to six carbon atoms (i.e., $C_1$-$C_6$ alkoxy). Examples of alkoxy groups, include, but are not limited to, groups such as methoxy, ethoxy, propyloxy, isopropyloxy, butyloxy, isobutyloxy, tert-butyloxy, pentyloxy, or hexyloxy, and the like.

As used herein, "amide" or "amido" refers to a chemical moiety with the formula —C(O)NR$^a$— or —NR$^a$C(O)— wherein R$^a$ is H or $C_1$-$C_6$ alkyl.

As used herein, "amino" or "amine" refers to a —NH$_2$ radical group.

As used herein, "alkylamino" refers to a group of formula —NH(alkyl), wherein the alkyl group each has 1 to 6 carbons.

As used herein, the term "dialkylamino" refers to a group of formula —N(alkyl)$_2$, wherein the two alkyl groups each independently have 1 to 6 carbons.

As used herein, "aryl" refers to a polyunsaturated, aromatic, hydrocarbon moiety which can be a single ring or multiple rings (e.g., 1 to 2 rings) which are fused together or linked covalently, having from six to twelve carbon atoms (i.e., $C_6$-$C_{12}$ aryl). Non-limiting examples of aryl groups include phenyl, 1-naphthyl, 2-naphthyl, and 4-biphenyl.

As used herein, "arylalkyl" refers to an (aryl)alkyl- radical wherein aryl and alkyl moieties are as disclosed herein. The arylalkyl may be represented as $C_6$-$C_{12}$ aryl-$C_1$-$C_6$ alkyl, a phenylalkyl, e.g. benzyl, and as structures such as the following non-limiting exemplary structures:

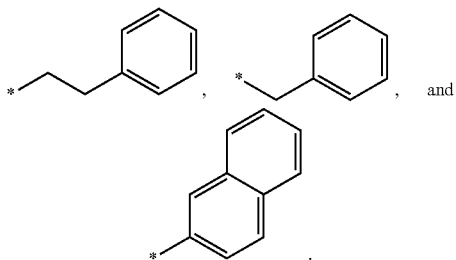

As used herein, "aryloxy" refers to —O-(aryl), wherein the aryl moiety is as defined herein. In one-non-limiting example, the may be phenoxy including the following exemplary structure.

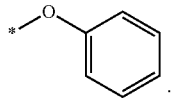

As used herein, "arylalkoxy" refers to —O-(arylalkyl), wherein the arylalkyl moiety is as defined herein e.g. —O—$C_6$-$C_{12}$ aryl-$C_1$-$C_6$ alkyl, —O— $C_1$-$C_6$ alkyl-$C_6$-$C_{12}$ aryl, and —$C_6$-$C_{12}$ aryl-$C_1$-$C_6$ alky-O.

As used herein, "carboxyl" refers to a —(C=O) radical.

As used herein, "cyano" refers to a —CN radical.

As used herein, "cycloalkyl" refers to a monocyclic or polycyclic radical that contains only carbon and hydrogen, and may be saturated, or partially unsaturated. Cycloalkyl groups include groups having from 3 to 10 ring atoms (i.e. $C_3$-$C_{10}$ cycloalkyl). Examples of cycloalkyl groups include, but are not limited to, groups such as cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like.

As used herein, "cycloalkyloxy" refers to —O-(cycloalkyl), wherein the cycloalkyl moiety is as defined herein e.g. —O—($C_3$-$C_{10}$ cycloalkyl).

As used herein, "halo" or "halogen," independently or as part of another substituent, mean, unless otherwise stated, a fluorine, chlorine, bromine, or iodine atom. The term "halide" by itself or as part of another substituent, refers to a fluoride, chloride, bromide, or iodide atom.

As used herein, "haloalkyl" and "haloalkoxy" can include alkyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

As used herein, "heteroaryl" refers to a 5- to 14-membered aromatic radical (e.g., $C_2$-$C_{13}$ heteroaryl) that includes one or more ring heteroatoms selected from nitrogen, oxygen and sulfur, and which may be a monocyclic or bicyclic ring system. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. An N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryl groups include without limitation, pyridyl, pyrimidinyl, pyrazinyl, pyridazinyl, triazinyl, furyl (furanyl), quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like.

As used herein, "heteroarylalkyl" refers to refers to an (heteroaryl)alkyl- radical wherein the heteroaryl and alkyl moieties are as disclosed herein. A heteroarylalkyl may be represented as 5-14-membered heteroaryl-$C_1$-$C_6$ alkyl, by name such as a pyridylalkyl and may be depicted as a structure as in the following non-limiting structural example

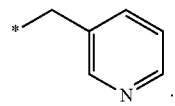

As used herein, "heteraryloxy" refers to —O-(heteroaryl), wherein the heteroaryl moiety is as defined herein. For example, such heteraryloxy may include a pyridyloxy as depicted in the following structural example

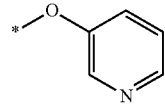

As used herein, "heterocycloalkyl" can be a stable 3- to 18-membered non-aromatic ring radical that comprises two to twelve carbon atoms and from one to six heteroatoms selected from nitrogen, oxygen and sulfur. Examples of heterocycloalkyl groups include, but are not limited to, groups such as dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, and the like.

As used herein, "hydroxy" or "hydroxyl" refers to —OH.

As used herein, "hydroxyalkyl" refers to an alkyl group having 1 to 10 carbon atoms, which is substituted with a hydroxyl group, e.g., hydroxypropyl.

As used herein, "keto" refers to a =O radical.

As used herein, "nitro" refers to —$NO_2$.

As used herein, "urea" refers to —$NR^a$—C(O)—$NR^a{}_2$ or —$NR^a$—C(O)$NR^a$—, wherein $R^a$ is H or $C_1$-$C_6$ alkyl.

As used herein, "sulfonyl" refers to —$S(O)_2$—$R^a$, wherein $R^a$ is $C_1$-$C_6$ alkyl.

As used herein, "sulfonylurea" refers to —$S(O)_2$—$NR^a$—C(O)—$NR^a$— or —$NR^a$—C(O)—$NR^a$—$SO_2$—, wherein $R^a$ is H or $C_1$-$C_6$ alkyl.

As used herein, "sulfonamidyl" refers to —S(O)$_2$—NR$^a$— or —NR$^a$—S(O)$_2$—, wherein R$^a$ is H or C$_1$-C$_6$ alkyl.

As used herein, "thionyl" refers to —S(O)—R$^a$, wherein R$^a$ is C$_1$-C$_6$ alkyl.

The terms "antagonist" and "inhibitor" are used interchangeably to refer to an agent that decreases or suppresses a biological activity, such as to repress an activity of an ion channel, such as TRPC5. TRPC5 ion channels as described herein include homomultimeric and heteromultimeric structures (e.g., homomultimeric TRPC5 and heteromeric TRPC5-TRPC1 or TRPC5-TRPC4). TRPC5 antagonists include inhibitors having any combination of the structural and/or functional properties disclosed herein.

An "effective amount" of, e.g., a TRPC5 antagonist, with respect to the subject methods of inhibition or treatment, refers to an amount of the antagonist in a preparation which, when applied as part of a desired dosage regimen brings about a desired clinical or functional result. Without being bound by theory, an effective amount of a TRPC5 antagonist for use in the methods of the present invention includes an amount of a TRPC5 antagonist effective to decrease one or more in vitro or in vivo function of a TRPC5 channel. Exemplary functions include, but are not limited to, membrane polarization (e.g., an antagonist may promote hyperpolarization of a cell), ion flux, ion concentration in a cell, outward current, and inward current. Compounds that antagonize TRPC5 function include compounds that antagonize an in vitro or in vivo functional activity of TRPC5. When a particular functional activity is only readily observable in an in vitro assay, the ability of a compound to inhibit TRPC5 function in that in vitro assay serves as a reasonable proxy for the activity of that compound. In certain embodiments, an effective amount is an amount sufficient to inhibit a TRPC5-mediated current and/or the amount sufficient to inhibit TRPC5 mediated ion flux.

The TRPC5 antagonists for use in the methods of the present invention may be characterized according to their activity, or lack of activity, against one or more other ion channels. When other ion channels are referred to, inhibition of a function of such other ion channels is defined similarly. For example, inhibition of an ion channel or an activity of an ion channel means the antagonist inhibits one or more functional activities of the other ion channel. Such functions include the current mediated by the particular ion channel, ion flux, or membrane polarization.

The term "preventing" is art-recognized, and when used in relation to a condition, such as a local recurrence, a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "small molecule" refers to a compound having a molecular weight less than about 2500 amu, preferably less than about 2000 amu, even more preferably less than about 1500 amu, still more preferably less than about 1000 amu, or most preferably less than about 750 amu.

The terms "TRPC5", "TRPC5 protein", and "TRPC5 channel" are used interchangeably throughout the application. Unless expressly stated, the term TRPC5 includes homomultimeric structures (e.g., homomultimeric TRPC5) and heteromultimeric structures (e.g., heteromultimeric TRPC5-TRPC1).

The term "oxidative metabolite" is intended to encompass compounds that are produced by metabolism of the parent compound under normal physiological conditions. Specifically, an oxidative metabolite is formed by oxidation of the parent compound during metabolism. For example, a thioether group may be oxidized to the corresponding sulfoxide or sulfone.

The term "solvate" as used herein, refers to a compound formed by solvation (e.g., a compound formed by the combination of solvent molecules with molecules or ions of the solute).

The term "hydrate" as used herein, refers to a compound formed by the union of water with the parent compound.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

Contemplated equivalents of the compounds described above include compounds which otherwise correspond thereto, and which have the same general properties thereof (e.g., the ability to antagonize TRPC5 activity), wherein one or more simple variations of substituents are made which do not adversely affect the efficacy of the compound. In general, the compound of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as (3-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art. Compounds of the invention also include tautomeric forms, such as keto-enol tautomers.

Compounds of the invention can exist in unsolvated forms as well as solvated forms, including hydrated forms. In general, the solvated forms are equivalent to unsolvated forms and are encompassed within the scope of the present invention.

The term "pharmaceutically acceptable salts" includes salts of a compound of formula (I) which are prepared with relatively nontoxic acids or bases. Base addition salts can be obtained by contacting the neutral form of a compound of formula (I) with a sufficient amount of the desired base, either neat or in a suitable inert solvent. Examples of pharmaceutically acceptable base addition salts include sodium, potassium, calcium, ammonium, organic amino, or magnesium salt, or a similar salt. Acid addition salts can be obtained by contacting the neutral form of a compound of formula (I) with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, trifluoroacetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are the salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19).

The neutral forms of a compound of Formula (I) is preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The term "low enough pyrogen activity", with reference to a pharmaceutical preparation, refers to a preparation that does not contain a pyrogen in an amount that would lead to an adverse effect (e.g., irritation, fever, inflammation, diarrhea, respiratory distress, endotoxic shock, etc.) in a subject to which the preparation has been administered. For example, the term is meant to encompass preparations that are free of, or substantially free of, an endotoxin such as, for example, a lipopolysaccharide (LPS).

Diseases, Disorders, or Conditions Related to TRPC5 Function

In certain embodiments, the invention provides methods and compositions for antagonizing a function of a TRPC5 channel in vitro or in vivo. Exemplary functions include, but are not limited to, TRPC5-mediated current. In certain embodiments, the invention provides methods for treating a disease or disorder or condition by administering a compound of the invention. In other embodiments, the compound as described herein selectively inhibits the expression level and/or activity of a TRPC5 protein. In other words, in certain embodiment, the compound as described herein inhibits the activity of a TRPC5 protein preferentially in comparison to the activity of one or more other ion channels.

Treatment of Anxiety and Fear-Related Disorders

In certain embodiments, the compounds of the invention can be used for preventing or treating anxiety and fear-related disorders (see, e.g., Riccio et al. (2009) Cell 137: 761-72). Examples of such disorders include post-traumatic stress disorder, panic disorder, agoraphobia, social phobias, generalized anxiety disorder, panic disorder, social anxiety disorder, obsessive-compulsive disorder, and separation anxiety.

Memory, Motion and Mood Disorders

A compound of Formula (I) is also useful for the treatment of Parkinson's disease, epilepsy, memory disorders, stroke, seizure, and mood disorders. Mood disorders include depression (e.g., major depression, psychiatric depression, dysthymia, and postpartum depression) and bipolar disorder (e.g., bipolar I, bipolar II, and cyclothymia). Memory disorders are conditions associated with any memory loss and may result from Alzheimer's disease, amnesia, aphasia, atherosclerosis, brain injury or disorder, brain tumor, chronic fatigue syndrome, Creutzfedt-Jacob disease, dissociative amnesia, depression, fuge amnesia, Huntington's disease, learning disorders, sleeping disorders, multiple personality disorder, pain, post-traumatic stress disorder, schizophrenia, sports injuries, stroke, and Wernicke-Korsakoff syndrome.

Treatment of Pain, Sensitivity to Pain and Touch, or Pain-Related Diseases or Disorders In certain embodiments, a compound of Formula (I) is used to treat or ameliorate pain. Exemplary classes of pain that can be treated using a compound of Formula (I) include, but are not limited to nociceptive pain, inflammatory pain, and neuropathic pain. The pain can be chronic or acute.

A compound of Formula (I) may be particularly useful in the treatment of pain associated with cancer, osteoarthritis, rheumatoid arthritis, post-herpetic neuralgia, burns, and other indications detailed above. To further illustrate, additional exemplary indications for which a compound of Formula (I) can be used include oral pain, pelvic pain, Fabry's disease, complex regional pain syndrome, pancreatitis, and fibromyalgia syndrome.

A compound of Formula (I) may also be used in connection with prevention or treatment of sensitivity to pain and touch. Pain or sensitivity to pain and touch may be indicated in a variety of diseases, disorders or conditions, including, but not limited to, diabetic neuropathy, breast pain, psoriasis, eczema, dermatitis, burn, post-herpetic neuralgia (shingles), nociceptive pain, peripheral neuropathic and central neuropathic pain, chronic pain, cancer and tumor pain, spinal cord injury, crush injury and trauma induced pain, migraine, cerebrovascular and vascular pain, sickle cell disease pain, rheumatoid arthritis pain, musculoskeletal pain including treating signs and symptoms of osteoarthritis and rheumatoid arthritis, orofacial and facial pain, including dental, temperomandibular disorder, and cancer related, lower back or pelvic pain, surgical incision related pain, inflammatory and non-inflammatory pain, visceral pain, psychogenic pain and soft tissue inflammatory pain, fibromyalgia-related pain, and reflex sympathetic dystrophy, and pain resulting from kidney stones or urinary tract infection.

The foregoing are merely exemplary of diseases and conditions that cause or lead to inflammation, lesions, ulcers, or other sources of oral pain. In other embodiments, the oral pain is due to an injury to the mouth, jaw, lips, gums, or teeth. In other embodiments, the oral pain is due to oral surgery, for example, surgery for cancer, tooth extraction, or jaw remodeling. Other conditions that may lead to oral ulcers, and thus oral pain, include, but are not limited to chickpox, herpes zoster, infectious mononucleosis, syphilis, tuberculosis, acute necrotizing gingivitis, and burning mouth syndrome.

Fibromyalgia (FMS; fibromyalgia syndrome) is a widespread musculoskeletal pain and fatigue disorder. Fibromyalgia is characterized by pain in the muscles, ligaments, and tendons. The condition affects more women than men, and occurs in people of all ages. Overall, FMS is estimated to afflict 3-6% of the population. Patients have described the pain associated with fibromylagia as deep muscular aching, throbbing, shooting, and stabbing. The pain sometimes includes an intense burning sensation. The pain and stiffness are often worse in the morning or after repetitive use of a particular muscle group.

Additionally, varying levels of fatigue ranging from mild to incapacitating are often associated with fibromylagia. Other symptoms of fibromylagia include gastrointestinal symptoms. Irritable bowel syndrome and IBS-like symptoms such as constipation, diarrhea, frequent abdominal pain, abdominal gas, and nausea occur in roughly 40 to 70% of FMS patients. Acid reflux or gastroesophogeal reflux disease (GERD) occurs at a similar frequency.

Complex Regional Pain Syndrome (CRPS; also known as chronic regional pain syndrome) is a chronic pain condition. CRPS was formerly known as reflex sympathetic dystrophy (RSD). CRPS is a chronic, painful, and progressive neurological condition that affects skin, muscles, joints, and bones. The syndrome usually develops in an injured limb, such as a broken leg or following surgery. However, many cases involve only a minor injury, such as a sprain, and sometimes no precipitating injurious event can be identified. CRPS involves continuous, intense pain that is disproportionate to the severity of the injury. The pain worsens, rather than improves, over time.

Although CRPS can affect a variety of regions of the body, it most often affects the arms, legs, hands, or feet. Often the pain begins in one portion of a limb, but spreads over time to include the entire limb or even to include a different limb. Typical features include dramatic changes in the color and temperature of the skin over the affected limb or body part, accompanied by intense burning pain, skin sensitivity, sweating, and swelling.

The compounds disclosed herein can also be used to treat endometriosis and the pain associated therewith.

Neurological or Neurodegenerative Diseases and Disorders

Neurodegenerative diseases and disorders include but are not limited to Alzheimer's disease (AD), Parkinson's disease, Huntington's disease, amyotrophic lateral sclerosis (ALS), and other brain disorders caused by trauma or other insults including aging.

Mechanisms associated with calcium signaling may be altered in many neurodegenerative diseases and in disorders resulting from brain injury. For example, fibroblasts or T-lymphocytes from patients with AD have consistently displayed an increase in $Ca^{2+}$ release from intracellular stores compared to controls (Ito et al. (1994) Proc. Natl. Acad. Sci. U.S.A. 91:534-538; Gibson et al. (1996) Biochem. Biophys. ACTA 1316:71-77; Etchenberrigaray et al. (1998) Neurobiology of Disease, 5:37-45). Consistent with these observations, mutations in presenilin genes (PS1 or PS2) associated with familial AD (FAD) have been shown to increase InsP3-mediated $Ca^{2+}$ release from internal stores (Guo et al. (1996) Neuro Report, 8:379-383; Leissring et al. (1999) J. Neurochemistry, 72:1061-1068; Leissring et al. (1999) J. Biol. Chem. 274 (46):32535-32538; Leissring et al. (2000) J. Cell Biol. 149 (4):793-797; Leissring et al. (2000) Proc. Natl. Acad. Sci. U.S.A. 97 (15):8590-8593). Furthermore, mutations in PS1 or PS2 associated with an increase in amyloidogenic amyloid β peptide generation in AD are reported to be associated with a decrease in intracellular calcium level (Yoo et al. (2000) Neuron, 27 (3):561-572).

Experimental traumatic brain injury has been shown to initiate massive disturbances in $Ca^{2+}$ concentrations in the brain that may contribute to further neuronal damage. Intracellular $Ca^{2+}$ may be elevated by many different ion channels. It has been further shown that channel blockers may be beneficial in the treatment of neurological motor dysfunction when administered in the acute posttraumatic period (Cheney et al. (2000) J. Neurotrauma, 17 (1):83-91).

Seizure

Excitotoxicity of a variety of origins leads to seizures. Commonly excess neuronal firing can drive seizure activity. Compounds that reduce the hyperexcitability of relevant neuronal populations have significant potential in reducing seizure activity.

Proteinuric Kidney Disease

TRPC5 is also expressed in the podocyte of the kidney. It has been proposed that there is an antagonistic regulation of actin dynamics and cell in the podocytes by TRPC5 and TRPC6 (Tian et al., (2010) Science Signaling). Thus, inhibiting TRPC5 may impact the reaction of the podocyte to injury.

Combination Therapy

The present invention provides a compound of Formula (I) for use in vitro and in vivo. The present invention also provides compositions and pharmaceutical compositions comprising a compound of Formula (I) that inhibits TRPC5 activity. In certain embodiments, the compound of Formula (I) is selective. In other words, in certain embodiments, the compound of Formula (I) inhibits TRPC5 activity preferentially over the activity of other ion channels. In certain embodiments, the compound of Formula (I) inhibits TRPC5 activity preferentially over TRPV1, TRPV2, TRPV3, TRPV4, TRPC3, TRPC6, TRPC7, TRPA1, and/or TRPM8 activity. For example, in certain embodiments, the compound of Formula (I) inhibits the activity of TRPC5 and also inhibits the activity of one or more of TRPC4, TRPV1, TRPV2, TRPV3, TRPV4, TRPC3, TRPC6, TRPC7, TRPA1, and TRPM8.

A compound of Formula (I) can be used alone or in combination with other pharmaceutically active agents. Examples of such other pharmaceutically active agents include, but are not limited to, anti-depressants, anti-anxiety agents, anti-epileptic agents, anti-inflammatory agents (e.g., NSAIDS, bradykinin receptor antagonists, hormones and autacoids such as corticosteroids), or anti-migraine agents. Certain active agents belong to more than one category.

In certain embodiments, a compound of Formula (I) is conjointly administered with an analgesic. Suitable analgesics include, but are not limited to, opioids, glucocorticosteroids, non-steroidal anti-inflammatories, naphthylalkanones, oxicams, para-aminophenol derivatives, propionic acids, propionic acid derivatives, salicylates, fenamates, fenamate derivatives, pyrozoles, and pyrozole derivatives. Examples of such analgesic compounds include, but are not limited to, codeine, hydrocodone, hydromorphone, levorphanol, morphine, oxycodone, oxymorphone, butorphanol, dezocine, nalbuphine, pentazocine, etodolac, indomethacin, sulindac, tolmetin, nabumetone, piroxicam, acetaminophen, fenoprofen, flurbiprofen, ibuprofen, ketoprofen, naproxen, diclofenac, oxaprozin, aspirin, diflunisal, meclofenamic acid, mefanamic acid, prednisolone, and dexamethasone. Preferred analgesics are non-steroidal anti-inflammatories and opioids (preferably morphine).

In some embodiments, a compound of Formula (I) can be administered in conjunction with a therapeutic whose administration causes pain. For example, a compound of Formula (I) can be administered in conjunction with an anesthetic, to reduce the pain caused by the administration of the anaesthetic. A compound of Formula (I) can also be administered in conjunction with a chemotherapeutic agent, to reduce the pain caused by administration of the chemotherapeutic agent.

In certain embodiments, a compound of Formula (I) is conjointly administered with a non-steroidal anti-inflammatory. Suitable non-steroidal anti-inflammatory compounds include, but are not limited to, piroxicam, diclofenac, etodolac, indomethacin, ketoralac, oxaprozin, tolmetin, naproxen, flubiprofen, fenoprofen, ketoprofen, ibuprofen, mefenamic acid, sulindac, apazone, phenylbutazone, aspirin, celecoxib and rofecoxib.

Pharmaceutical Compositions

Suitable preparations for administering the compounds of the present invention will be apparent to those with ordinary skill in the art and include for example tablets, pills, capsules, suppositories, lozenges, troches, solutions, syrups, elixirs, sachets, injectables, inhalatives, powders, etc. The content of the pharmaceutically active compound(s) should be in the range from 0.1 to 95 wt.-%, preferably 5.0 to 90 wt.-% of the composition as a whole.

Suitable tablets may be obtained, for example, by mixing one or more compounds of the present invention with known excipients, for example inert diluents, carriers, disintegrants, adjuvants, surfactants, binders and/or lubricants. The tablets may also consist of several layers.

Dosages

The dose range of the compounds of the invention applicable per day is usually from 1 to 1000 mg, preferably from 5 to 800 mg, more preferably from 25 to 500 mg. Each dosage unit may conveniently contain from 1 to 1000 mg, preferably 25 to 500 mg.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Disease and Injury Models

A compound of Formula (I) which antagonizes TRPC5 function may be useful in the prophylaxis and treatment of any of the foregoing injuries, diseases, disorders, or conditions. In addition to in vitro assays of the activity of the compound of Formula (I), its efficacy can be readily tested in one or more animal models. By way of example, numerous well known animal models exist. One or more suitable animal models (e.g., suitable in light of the particular indication) can be selected.

Fear-related behaviors can be measured as described, e.g., in Riccio et al. Pain behaviors can be studied using various agents or procedures to simulate pain resulting from injuries, diseases, or other conditions. Blackburn-Munro (2004) Trends in Pharmacological Sciences 25: 299-305. Behavioral characteristics of challenged animals can then be observed. Compounds or procedures that may reduce pain in the animals can be readily tested by observing behavioral characteristics of challenged animals in the presence versus the absence of the test compound(s) or procedure.

Exemplary behavioral tests used to study chronic pain include tests of spontaneous pain, allodynia, and hyperalgesia. Id. To assess spontaneous pain, posture, gait, nocifensive signs (e.g., paw licking, excessive grooming, excessive exploratory behavior, guarding of the injured body part, and self-mutilation) can be observed. To measure evoked pain, behavioral responses can be examined following exposure to heat (e.g., thermal injury model).

Exemplary animal models of pain include, but are not limited to, the Chung model, the carageenan induced hyperalgesia model, the Freund's complete adjuvant induced hyperalgesia model, the thermal injury model, the formalin model and the Bennett Model. The Chung model of neuropathic pain (without inflammation) involves ligating one or more spinal nerves. Chung et al. (2004) Methods Mol Med 99: 35-45; Kim and Chung (1992) Pain 50: 355-363. Ligation of the spinal nerves results in a variety of behavioral changes in the animals including heat hyperalgesia, cold allodynia, and ongoing pain. Compounds that antagonize TRPC5 can be administered to ligated animals to assess whether they diminish these ligation-induced behavioral changes in comparison to that observed in the absence of compound.

Useful anxiety and depression models include the maternal separation model, the elevated plus-maze model, the forced swim test, the tail suspension test, the light/dark preference model, the light-enhanced startle model, and the ultrasonic vocalization model.

Useful seizure models include but are not limited to maximal electric shock (MES), acoustic startle in susceptible animals (eg DBA mice), and chemical induced seizure (with proconvulsant compounds such as pilocarpine, pentalene tetrazole, kainic acid, N-methyl-D-aspartic acid).

Useful models of kidney function include the LPS-induced proteinuria (waiting for a reference for others).

EXAMPLES

Example 1

High Throughput Screening Assay

The assay depended on detection of the rise in intracellular Ca2+ concentration ([Ca2+]i) following channel activation in cells inducibly expressing the TRPC5 channel. Ca2+ rise was quantified with the use of fluorescent Ca2+ indicators that were loaded into cells and thereafter indicated the [Ca2+]i Ca2+ influx followed activation of the TRPC5 channel. Compounds inhibiting the [Ca2+]i rise were considered hits for further investigation.

The commercially available HEK293/TREx line (Invitrogen) was stably transfected with a TRPC5 construct and screened by conventional calcium imaging to find clones with TRPC5 expression following stimulation with 1 µg/ml tetracycline. These cells were maintained in the growth medium recommended by the manufacturer supplemented with 100 µg/ml hygromycin to promote retention of the TRPC5 construct. After growing to near confluency, cells were plated at a density of ~35,000 cells/well in 384 well CellBind plates (Corning) in the presence of 1 µg/ml tetracycline, and allowed to grow for 20-30 hrs. A nearly confluent monolayer resulted. Cells were then loaded with Ca2+ dye: Fura-2/AM or Fluo4/AM was added to the wells to a final concentration of 4 µM or 0.5 µM, respectively, and incubated for 80 min or 60 min, respectively, at room temperature. Supernatant was then removed from the cells by inverting plates with a sharp flick, and 25 µl Hank's Balanced Salt Solution (HBSS; 0.185 g/l D-glucose, 0.9767 g/l MgS04 (anhydrous), 0.4 g/l KCl, 0.06 g/l KH2PO4 (anhydrous), 0.35 g/l NaHCO3, 8.0 g/l NaCl, and 0.04788 g/l Na2HPO4 (anhydrous); pH 7.4) was then added to each well. Following ~0.5 hour for recovery from loading, cells were assayed using the Hamamatsu FDSS 6000 system, which permitted illumination alternately at 340 nm and 380 nm for Fura-2 experiments, or at 485 nm for Fluo4 experiments. Frames were acquired at a rate of 0.2 Hz. During the assay, the plates were continuously vortexed, with pipette mixing of wells following addition of each reagent. For the screening assay, 26 µl of a diluted compound stock (at 50 µM) was added to each well for 2 minutes following the collection of a short (4 frame) baseline. 13 µl 62 mM high-Ca2+Ringer solution (4.17 ml of normal ringer (with 2 mM Ca2+) plus 5.83 ml of isotonic calcium ringer (105 mM Ca2+; in this ringer all sodium has been replaced with calcium)) was then added to each well, achieving a final concentration of 14 mM Ca2+ and 10 µM test compound. Data was collected for ~3 minutes following addition of high Ca2+Ringer, where the fluorescent intensity (for Fluo4) and the F340/F380 ratio (for Fura-2) were proportional to the [Ca2+]i Negative controls consisted of HEK293/TREx TRPC5 cells exposed to high Ca2+ solution, but no compound. Positive control conditions consisted of addition of 2-APB, a promiscuous blocker of TRPC5 and other channels, to columns 23 and 24 of the plates, to a final concentration of 200 µM. These controls defined a screening window, and "hits" were defined as those compounds inhibiting the fluorescence response by at least 40%. $IC_{50}$ values were determined for compounds defined as "hits." The Fluo4 cell-based fluorescence assay was used to determine the intracellular Ca2+ concentration in the presence of varying drug concentration. Final concentrations of compounds tested were 20 µM, 6.667 µM, 2.222 µM, 0.741 µM, 0.247 µM, 0.082 µM, and 0.027 µM. Compounds were tested in triplicate at all concentrations. Standard software was used to fit $IC_{50}$ curves.

Additionally or alternatively, efficacy can be represented as % inhibition in the presence (of a given concentration of compound) versus the absence of compound or in comparison to a control compound. For example, efficacy can be represented as % inhibition of ion flux in the presence versus the absence of compound. Exemplary compounds are shown in Table 2 below.

TABLE 2

| Compound Number | $IC_{50}$ (nM) |
| --- | --- |
| 1 | 584 |
| 2 | 117 |
| 3 | 340 |
| 4 | 55 |
| 5 | <27 |
| 6 | <27 |
| 7 | 34.9 |
| 8 | 1700 |
| 13 | <21 |
| 14 | 82.2 |
| 15 | 112 |
| 16 | 27 |
| 17 | 31.6 |
| 18 | 27 |
| 19 | 226 |
| 21 | 194 |
| 22 | 369 |
| 23 | 27 |
| 24 | 242 |
| 25 | 168 |
| 26 | 1.91 |
| 27 | 134 |
| 28 | 4330 |

Example 2

Patch Clamp Experiments

Patch clamp experiments permit the detection of currents through the TRPC5 channel in the cell line described above. In normal whole-cell patch clamp recordings, a glass electrode is brought into contact with a single cell and a high-resistance (gigaohm) seal is established with the cell membrane. The membrane is then ruptured to achieve the whole-cell configuration, permitting control of the voltage of the cell membrane and measurement of currents flowing across the membrane using the amplifier attached to the electrode and resulting in the replacement of cytoplasm with the pipette solution. A perfusion system permits control of the extracellular solution, including the addition of blockers and activators of the current. The current can be activated by including 1.4 µM free $Ca^{2+}$ in the pipette (intracellular) solution, and 80 µM $LaCl_3$ in the extracellular solution.

TRPC5 cells were induced 20-48 hours, removed from growth plates, and replated at low density (to attain good single-cell physical separation) on glass coverslips for measurement. In some cases, cells were grown in low density overnight on glass coverslips. Patch clamp recordings were made in the whole-cell mode with a holding potential of −40 mV. Every 5 seconds, a voltage ramp was applied from −120 to +100 mV, 400 ms in duration. Currents elicited were quantified at −80 mV and +80 mV. The internal solution consisted of 140 mM cesium aspartate, 10 mM HEDTA, 2 mM $CaCl_2$, 2.27 mM $MgCl_2$ and 10 mM HEPES, pH 7.2, with 1,400 nM calculated free $Ca^{2+}$. The external solution consisted of 150 mM NaCl, 4.5 mM KCl, 1 mM $MgCl_2$, 2 mM $CaCl_2$ 10 mM HEPES, 10 mM glucose, 1 mM EGTA, pH 7.4. Upon addition of $LaCl_3$, TRPC5 current was induced only in TRPC5-expressing cells and not in parental HEK293 TREx cells. Removal of the $LaCl_3$ stimulus causes most of the current to go away. Potential blockers were tested for ability to block both inward and outward currents in the continued presence of $LaCl_3$.

$IC_{50}$ of a compound of Formula (I) was estimated by testing the compound at 5 µM and 500 nM. When 5 µM of a compound showed no block, $IC_{50}$ was estimated as >10 µM. When 5 µM of a compound showed 50% or less block, a rough estimate of $IC_{50}$ in the range of 5-10 µM could be made. $IC_{50}$ for a compound of Formula (I) between 500 nM and 5 µM was similarly estimated. Exemplary compounds are shown in Table 3 below.

TABLE 3

| Compound Number | $IC_{50}$ (nM) |
|---|---|
| 1 | <1 |
| 2 | <1 |
| 24 | 1.84 |
| 25 | 15.7 |
| 26 | <1 |
| 27 | <1 |

Example 3

General Experimental Procedures

General Procedures

All reagents were purchased from commercial suppliers and used without further purification unless otherwise stated. Reactions were monitored via thin layer chromatography (TLC) on silica gel plates and visualized using UV light (254 nm or 365 nm) and/or staining with a solution of DNP (12 g of 2,4-dinitrophenylhydrazine dissolved in $H_2SO_4$ (60 mL), water (80 mL) and ETOH (200 mL) and subsequent heating or monitored by LCMS. Preparative TLC plates used were Analtech Uniplate Silica Gel GF plates or Shanghia SANPONT PLC plate SGF254 20×20 cm size and 2000 um thickness.

All reactions were run under an inert atmosphere using either argon or nitrogen. All non-aqueous reactions were run using anhydrous solvents. All reactions were stirred either with a magnetic stir bar or with overhead mechanical stirring. All saturated extraction solutions are assumed to be aqueous ($NH_4Cl$ for example). All drying agents are anhydrous. Drying organic solutions with a drying agent implies that the drying agent was removed from the organic solution by filtration. Chromatography refers to column chromatography on silica gel. Concentration of reaction mixtures implies concentration under reduced pressure using of a Rotary Evaporation instrument. Drying of final products implies drying under high vacuum conditions. (MW) means using a microwave instrument with reaction carried out in a sealed microwave vial. Microwave reactions were carried out using a Biotage Smith Synthesizer.

LCMS were performed on a SHIMADZU LCMS-2010EV instrument using one of two sets of conditions. LCMS conditions one: (Chromolith SdeedROP, RP-18e column. 50×4.6 mm. mobile phase: Solvent A: $CH_3CN/H_2O/HCOOH=10/90/0.05$. Solvent B: $CH_3CN/H_2O/HCOOH=90/10/0.05$, 0.8 min @10% B. 2.7 min gradient (10-95% B), then 0.8 min @95% B. Flow rate: 3 mL/min. temperature: 40° C.). LCMS conditions two: (Zorbax. 3.5 micron. 2.1×50 mm $C_{18}$ column. Mobile phase: Solvent A: 0.1% $HCOOH/CH_3CN$. Solvent B: 0.1% $HCOOH/H2O$. Gradient 5% to 95% B using a 5 min or 8 min runtime.

Preparative HPLC was performed either on a SHIMADZU LC-8A instrument. (Column: YMC Pack ODS-A (150*30 mm 10 um)) or LC-6AD (column: Shim=Pack PREP-ODS-H (250*20 mm, 10 um)) with UV detection which was controlled by LC solution Chemstation software. $H_2O$ (0.1% HCOOH) and methanol ($CH_3OH$) as mobile phase at the indicated flow rate.

Analytical HPLC was performed on a SHIMADZU LCMS-2010EV (Chromolith SpeedROD, RP-18e, 50×4.6 mm, mobile phase: Solvent A: $CH_3CN/H_2O/HCOOH=10/90/0.05$, Solvent B: $CH_3CN/H_2O/HCOOH=90/10/0.05$, 0.8 min@10% B, 2.7 min gradient (10-95% B), then 0.8 min@95% B, Flow rate: 3 mL/min, temperature: 40° C.

$^1H$ NMR spectra were recorded on either a Bruker Avance II 400 MHz or a Varian Unity Inova 400 MHz instrument. Chemical shifts (δ) are reported in ppm relative to tetramethylsilane (δ=o.oo ppm) and the spectra were calibrated to the residual solvent signal of Chloroform (δ=7.26). Dimethyl sulfoxide (δ=2.52), methanol (δ=3.34). Data for $^1H$ NMR spectra are reported as follows: chemical shift (multiplicity, J value, number of hydrogens). Abbreviations are as follows: s (singlet), d (doublet), t (triplet), td (doublet of triplets) q (quartet), quint (quintet), m (multiplet), brd (broad).

LIST OF ABBREVIATIONS AND TERMS

AcONa sodium acetate
$Ac_2O$ acetic anhydride
aq. aqueous
Bn benzyl
Celite diatomaceous earth
$CDCl_3$ deuterated chloroform
CDI 1,1'-carbonyldiimidazole
$CD_3OD$ deuterated methanol
d deuterated
DCM dichloromethane
DHP dihydropyran
DIPEA diisopropylethylamine
DMA dimethylacetamide
DMAP 4-dimethylaminopyridine
DMF N,N-dimethylformamide
DMSO dimethyl sulfoxide
DMSO-$d_6$ deuterated DMSO
EA ethyl acetate
ETOH ethanol 200 proof
h hours
Hex hexanes
Hep heptanes
HPLC high pressure liquid chromatography
HOAc acetic acid
IBX 2-iodobenzoic acid
LAH lithium aluminum hydride
LCMS liquid chromatography-mass spectrometry
LDA lithium diisopropylamine
MeOH methanol
M molarity
mmol millimolar
mg milligrams
mL milliliters
min minutes
MW microwave reactor
MTBE methyl tert-butyl ether
Na sodium
n-BuLi n-butyllithium
N normality
NCS n-chlorosuccinimide NBS n-bromosuccinimide
NMR nuclear magnetic resonance
Pd/C palladium on activated carbon
Pd(dppf)Cl₂ [1,1'Bis(diphenylphosphino)ferrocene]dichloropalladium(II)
Pd(PPh₃)₄ Bis(triphenylphosphine)palladium(II) dichloride
PE petroleum ether
PPTS pyridinium p-toluenesulfonate
Prep TLC preparative thin layer chromatography
Prep HPLC preparative high pressure liquid chromatography
psi pounds per square inch
RT room temperature
SEM 2-(trimethylsilyl)ethoxymethyl
TBAI tetrabutylammonium iodide
TBAF tetrabutylammonium fluoride
TBS t-butyldimethyl silyl
TEA triethylamine
TFA trifluoroacetic acid
THP tetrahydropyranyl
TLC thin layer chromatography
THF tetrahydrofuran
$T_r$ LCMS retention time Preparation of Compounds Compound 1

5-(4-chlorobenzyl)-3-(3-hydroxypropyl)-1-methyl-6-(3-(trifluoromethoxy)phenoxy)thieno[2,3-d]pyrimidine-2,4(1H,3H)-dione

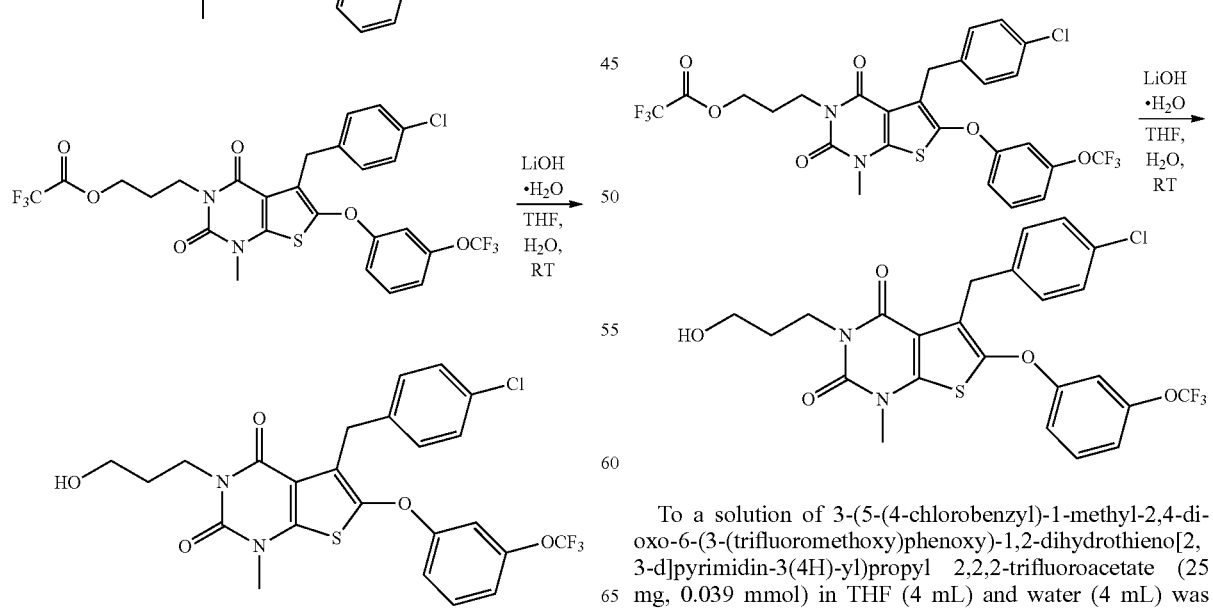

Step 1 3-(5-(4-chlorobenzyl)-1-methyl-2,4-dioxo-6-(3-(trifluoromethoxy)phenoxy)-1,2-dihydrothieno[2,3-d]pyrimidin-3(4H)-yl)propyl 2,2,2-trifluoroacetate

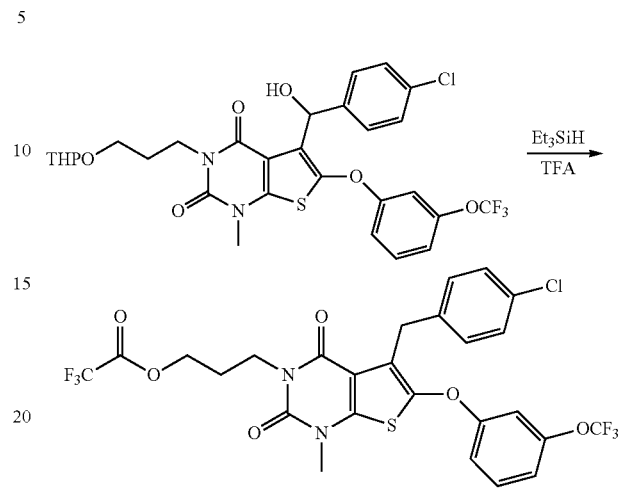

To a solution of 5-((4-chlorophenyl)(hydroxy)methyl)-1-methyl-3-(3-((tetrahydro-2H-pyran-2-yl)oxy)propyl)-6-(3-(trifluoromethoxy)phenoxy)thieno[2,3-d]pyrimidine-2,4(1H,3H)-dione (See Compound 21, Step 2, 30 mg, 0.047 mmol) in TFA (2 mL) was added triethylsilane (1 mL). The reaction was stirred at RT for 3 h then diluted with DCM (5 mL) and water (5 mL). The organic layer was dried over Na₂SO₄ and concentrated to give 3-(5-(4-chlorobenzyl)-1-methyl-2,4-dioxo-6-(3-(trifluoromethoxy)phenoxy)-1,2-dihydrothieno[2,3-d]pyrimidin-3(4H)-yl)propyl 2,2,2-trifluoroacetate (25 mg, 83.9% yield) as an oil. LCMS: MH⁺ 637 and $T_R$=2.274 min.

Step 2 5-(4-chlorobenzyl)-3-(3-hydroxypropyl)-1-methyl-6-(3-(trifluoromethoxy)phenoxy)thieno[2,3-d]pyrimidine-2,4(1H,3H)-dione

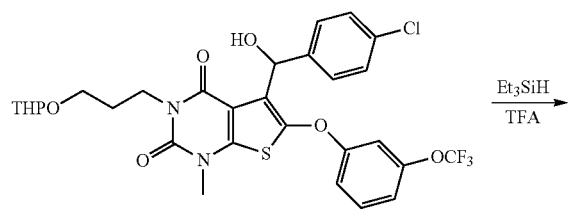

To a solution of 3-(5-(4-chlorobenzyl)-1-methyl-2,4-dioxo-6-(3-(trifluoromethoxy)phenoxy)-1,2-dihydrothieno[2,3-d]pyrimidin-3(4H)-yl)propyl 2,2,2-trifluoroacetate (25 mg, 0.039 mmol) in THF (4 mL) and water (4 mL) was added LiOH/H₂O (3.29 mg, 0.079 mmol). The reaction was stirred at RT for 15 min then diluted with DCM (5 mL) and water (5 mL). The organic layer was dried over $Na_2SO_4$ and concentrated to a residue which was purified by Prep HPLC to give 5-(4-chlorobenzyl)-3-(3-hydroxypropyl)-1-methyl-6-(3-(trifluoromethoxy)phenoxy)thieno[2,3-d]pyrimidine-2,4(1H,3H)-dione (10 mg, 47.1% yield) as a white solid. $^1$H NMR (DMSO-$d_6$) δ: 7.49 (t, J=8.3 Hz, 1H), 7.21 (dd, J=18.8, 8.6 Hz, 4H), 7.17-7.07 (m, 2H), 7.03 (s, 1H), 4.50 (t, J=5.1 Hz, 1H), 4.10 (s, 2H), 3.99-3.86 (m, 2H), 3.51-3.42 (m, 2H), 3.41 (s, 3H), 1.69 (s, 2H). LCMS: MH$^+$ 541 and $T_R$=3.317 min.

Compound 2

5-(4-chlorobenzyl)-6-(3-chlorophenoxy)-3-(3-hydroxypropyl)-1-methylthieno[2,3-d]pyrimidine-2,4(1H,3H)-dione

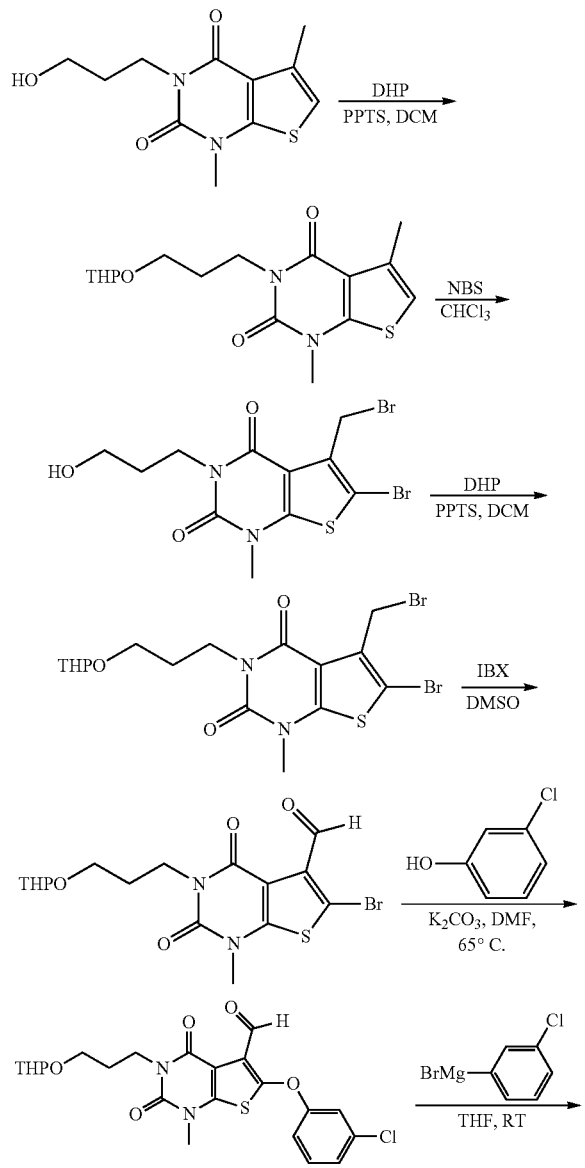

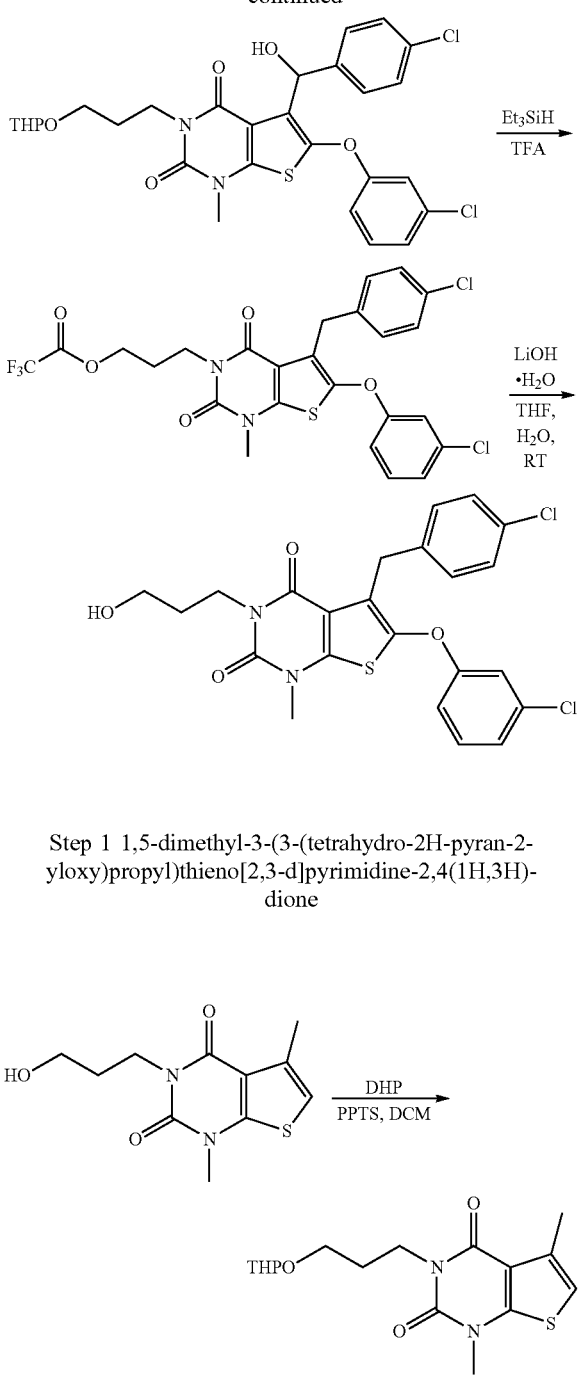

Step 1 1,5-dimethyl-3-(3-(tetrahydro-2H-pyran-2-yloxy)propyl)thieno[2,3-d]pyrimidine-2,4(1H,3H)-dione To a solution of 3-(3-hydroxypropyl)-1,5-dimethylthieno[2,3-d]pyrimidine-2,4(1H,3H)-dione (9 g, 35.4 mmol) and PPTS (900 mg, 3.54 mmol) in DCM (90 mL) at 0° C. was added DHP (8.96 g, 0.106 mol) dropwise. The reaction was stirred at RT for 18 h, poured into water (30 mL) and extracted with DCM (2×20 mL). The combined organic layers were washed with brine (20 mL), dried over $Na_2SO_4$ and concentrated to a residue which was purified by chromatography and eluted with PE/EA (4:1) to give 1,5-dimethyl-3-(3-(tetrahydro-2H-pyran-2-yloxy)propyl)thieno[2,3-d]pyrimidine-2,4(1H,3H)-dione (11.2 g, 93.4% yield) as a yellow oil. LCMS: [MH$^+$-THP] 255 and $T_R$=1.473 min.

Step 2 6-bromo-5-(bromomethyl)-3-(3-hydroxypropyl)-1-methylthieno[2,3-d]pyrimidine-2,4(1H,3H)-dione

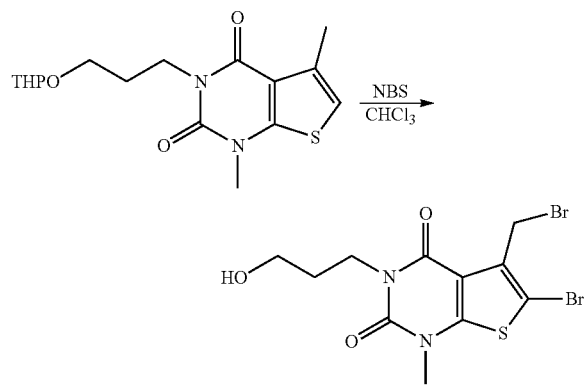

To a stirred solution of 1,5-dimethyl-3-(3-(tetrahydro-2H-pyran-2-yloxy)propyl)thieno[2,3-d]pyrimidine-2,4(1H,3H)-dione (11.2 g, 33.1 mmol) in CHCl$_3$ (100 mL) at 0° C. was added portion wise NBS (23.6 g, 0.132 mol). The reaction mixture was stirred at 0° C. for 2 h, poured into water (30 mL) and extracted with DCM (2×20 mL). The combined organic layers were washed with brine (20 mL), dried over Na$_2$SO$_4$ and concentrated to a residue which was purified by chromatography eluted with PE/EA (1:1) to give 6-bromo-5-(bromomethyl)-3-(3-hydroxypropyl)-1-methylthieno[2,3-d]pyrimidine-2,4(1H,3H)-dione (2.5 g, 18.5% yield) as a yellow solid.

Step 3 6-bromo-5-(bromomethyl)-1-methyl-3-(3-(tetrahydro-2H-pyran-2-yloxy)propyl)thieno-[2,3-d]pyrimidine-2,4(1H,3H)-dione

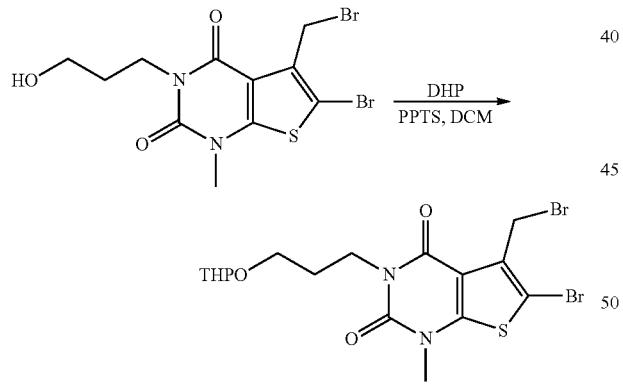

To a solution of 6-bromo-5-(bromomethyl)-3-(3-hydroxypropyl)-1-methylthieno[2,3-d]pyrimidine-2,4(1H,3H)-dione (2.5 g, 6.1 mmol) and PPTS (153 mg, 0.61 mmol) in DCM (25 mL) at 0° C. was added DHP (2.00 g, 24.5 mmol) dropwise. The reaction was stirred at RT for 18 h, poured into water (30 mL) and extracted with DCM (2×20 mL). The combined organic layers were washed with brine (20 mL), dried over Na$_2$SO$_4$ and concentrated to a residue which was purified by chromatography eluted with PE/EA (4:1) to give 6-bromo-5-(bromomethyl)-1-methyl-3-(3-(tetrahydro-2H-pyran-2-yloxy)propyl)thieno[2,3-d]pyrimidine-2,4(1H,3H)-dione (1.7 g, 56.7% yield) as a yellow oil.

Step 4 6-bromo-1-methyl-2,4-dioxo-3-(3-(tetrahydro-2H-pyran-2-yloxy)propyl)-1,2,3,4-tetrahydrothieno[2,3-d]pyrimidine-5-carbaldehyde

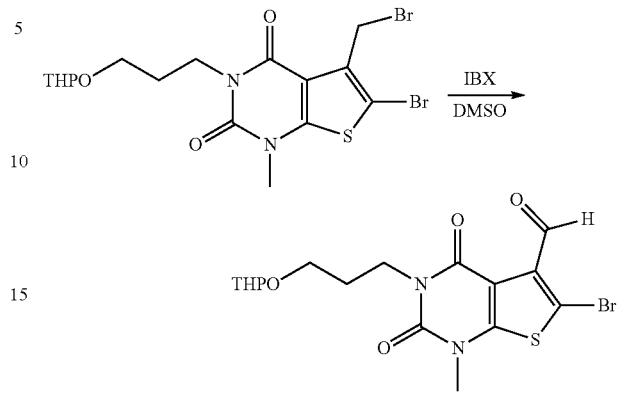

To a solution of 6-bromo-5-(bromomethyl)-1-methyl-3-(3-(tetrahydro-2H-pyran-2-yloxy)propyl) thieno[2,3-d]pyrimidine-2,4(1H,3H)-dione (1.7 g, 3.43 mmol) in DMSO (20 mL) was added IBX (1.92 g, 6.85 mmol). The reaction was heated at 50° C. for 2 h, cooled to RT then diluted with EA (80 mL) and water (50 mL). The organic layer was dried over Na$_2$SO$_4$ and concentrated to a residue which was purified by chromatography eluted with PE/EA (5:1) to give 6-bromo-1-methyl-2,4-dioxo-3-(3-(tetrahydro-2H-pyran-2-yloxy)propyl)-1,2,3,4-tetrahydrothieno[2,3-d]pyrimidine-5-carbaldehyde (500 mg, 33.8% yield) as a yellow oil. LCMS: MH$^+$ 431 and T$_R$=1.313 min.

Step 5 6-(3-chlorophenoxy)-1-methyl-2,4-dioxo-3-(3-(tetrahydro-2H-pyran-2-yloxy)propyl)-1,2,3,4-tetrahydrothieno[2,3-d]pyrimidine-5-carbaldehyde

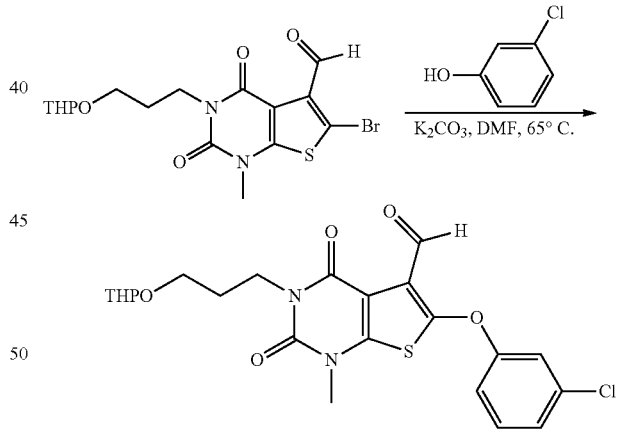

To a mixture of 6-bromo-1-methyl-2,4-dioxo-3-(3-(tetrahydro-2H-pyran-2-yloxy)propyl)-1,2,3,4-tetrahydrothieno[2,3-d]pyrimidine-5-carbaldehyde (100 mg, 0.23 mmol), K$_2$CO$_3$ (159 mg, 1.15 mmol) in DMF (3 mL) was added 3-chlorophenol (90 mg, 0.70 mmol). The reaction was heated at 65° C. for 1 h, cooled to RT then diluted with EA (30 mL) and water (30 mL). The organic layer was dried over Na$_2$SO$_4$ and concentrated to a residue which was purified by chromatography and eluted with PE/EA (5:1) to give 6-(3-chlorophenoxy)-1-methyl-2,4-dioxo-3-(3-(tetrahydro-2H-pyran-2-yloxy)propyl)-1,2,3,4-tetrahydrothieno[2,3-d]pyrimidine-5-carbaldehyde (65 mg, 58.6% yield) as a yellow oil. LCMS: MH$^+$ 479 and T$_R$=1.836 min.

Step 6 6-(3-chlorophenoxy)-5-((4-chlorophenyl)(hydroxy)methyl)-1-methyl-3-(3-(tetrahydro-2H-pyran-2-yloxy)propyl)thieno[2,3-d]pyrimidine-2,4(1H,3H)-dione

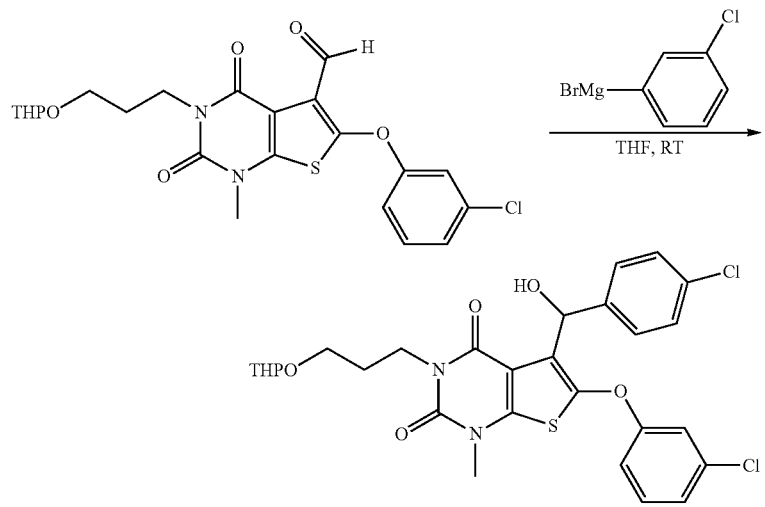

To a solution of 6-(3-chlorophenoxy)-1-methyl-2,4-dioxo-3-(3-(tetrahydro-2H-pyran-2-yloxy) propyl)-1,2,3,4-tetrahydrothieno[2,3-d]pyrimidine-5-carbaldehyde (65 mg, 0.136 mmol) in THF (2 mL) was added (3-chlorophenyl)magnesium bromide (35 mg, 0.163 mmol). The reaction was stirred at RT for 15 minutes then diluted with EA (20 mL) and water (20 mL). The organic layer was dried over Na$_2$SO$_4$ and concentrated to give a residue which was purified by chromatography eluted with PE/EA (4:1) to give 6-(3-chlorophenoxy)-5-((4-chlorophenyl) (hydroxy)methyl)-1-methyl-3-(3-(tetrahydro-2H-pyran-2-yloxy)propyl)thieno[2,3-d]pyrimidine-2,4(1H,3H)-dione (45 mg, 56.3% yield) as a yellow oil. LCMS: MH$^+$ 591 and T$_R$=2.138 min.

Step 7 3-(5-(4-chlorobenzyl)-6-(3-chlorophenoxy)-1-methyl-2,4-dioxo-1,2-dihydrothieno[2,3-d]pyrimidin-3(4H)-yl)propyl 2,2,2-trifluoroacetate

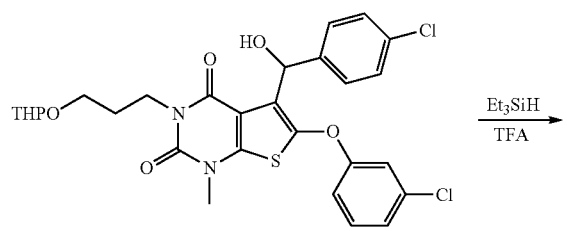

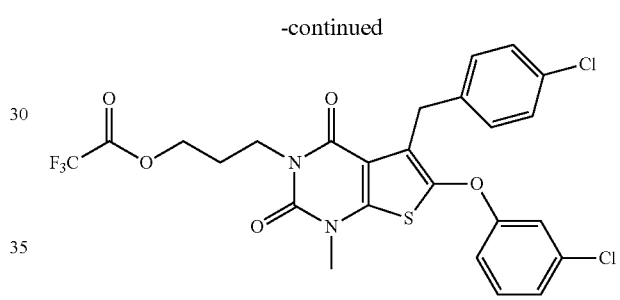

To a solution of 6-(3-chlorophenoxy)-5-((4-chlorophenyl)(hydroxy)methyl)-1-methyl-3-(3-(tetrahydro-2H-pyran-2-yloxy)propyl)thieno[2,3-d]pyrimidine-2,4(1H,3H)-dione (45 mg, 0.076 mmol) in TFA (0.9 mL) was added Et$_3$SiH (0.3 mL). The reaction was stirred at RT for 15 min then diluted with EA (20 mL) and water (20 mL). The organic layer was dried over Na$_2$SO$_4$ and concentrated to give 3-(5-(4-chlorobenzyl)-6-(3-chlorophenoxy)-1-methyl-2,4-dioxo-1,2-dihydrothieno[2,3-d]pyrimidin-3(4H)-yl)propyl 2,2,2-trifluoroacetate (40 mg, 89.5% yield) as an oil. LCMS: MH$^+$ 587 and T$_R$=2.308 min.

Step 8 5-(4-chlorobenzyl)-6-(3-chlorophenoxy)-3-(3-hydroxypropyl)-1-methylthieno[2,3-d]pyrimidine-2,4(1H,3H)-dione

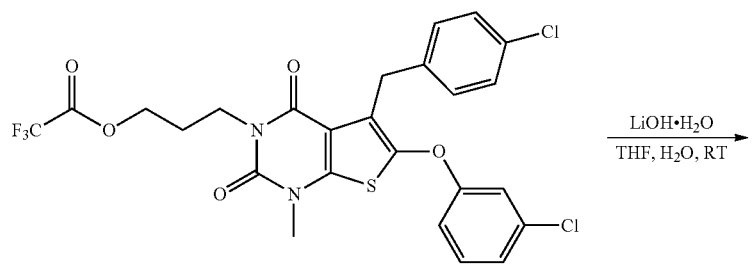

-continued

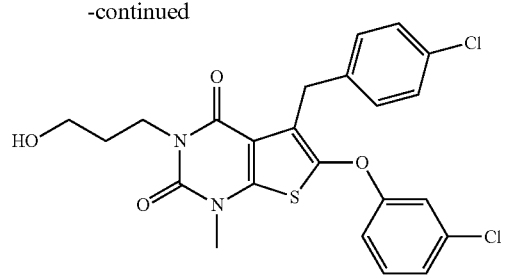

To a solution of 3-(5-(4-chlorobenzyl)-6-(3-chlorophenoxy)-1-methyl-2,4-dioxo-1,2-dihydro thieno[2,3-d]pyrimidin-3(4H)-yl)propyl 2,2,2-trifluoroacetate (40 mg, 0.068 mmol) in THF (3 mL) and water (3 mL) was added LiOH.H$_2$O (8.6 mg, 0.20 mmol). The reaction was stirred at RT for 15 min then diluted with EA (20 mL) and water (20 mL). The organic layer was dried over Na$_2$SO$_4$ and concentrated to a residue which was purified by Prep HPLC to give 5-(4-chlorobenzyl)-6-(3-chlorophenoxy)-3-(3-hydroxypropyl)-1-methylthieno[2,3-d]pyrimidine-2,4(1H,3H)-dione (13 mg, 38.9% yield) as a white solid. $^1$H NMR (CDCl$_3$) δ: 7.26-7.24 (m, 2H), 7.23 (d, J=6.0 Hz, 2H), 7.20 (s, 3H), 7.16 (d, J=8.5 Hz, 4H), 7.11 (d, J=8.0 Hz, 2H), 6.93 (dd, J=19.3, 5.2 Hz, 4H), 4.18 (dd, J=14.0, 8.0 Hz, 9H), 3.60-3.44 (m, 1H), 3.23 (t, J=7.1 Hz, 2H), 1.96-1.85 (m, 4H). LCMS: MH$^+$ 491 and T$_R$=3.276 min.

Compound 3

3-(3-hydroxypropyl)-5-isopentyl-1-methyl-6-(3-(trifluoromethoxy)phenyl)thieno[2,3-d]pyrimidine-2,4(1H,3H)-dione

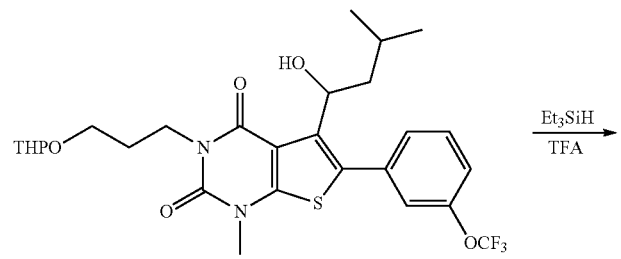

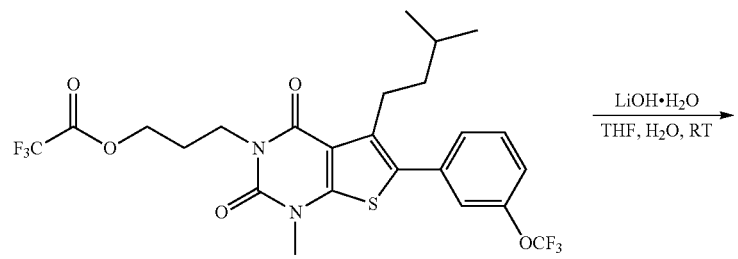

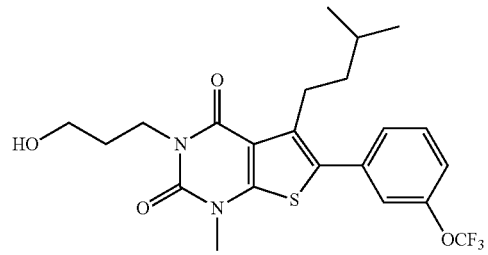

Step 1 3-(5-isopentyl-1-methyl-2,4-dioxo-6-(3-(trifluoromethoxy)phenyl)-1,2-dihydrothieno-[2,3-d]pyrimidin-3 (4H)-yl)propyl 2,2,2-trifluoroacetate

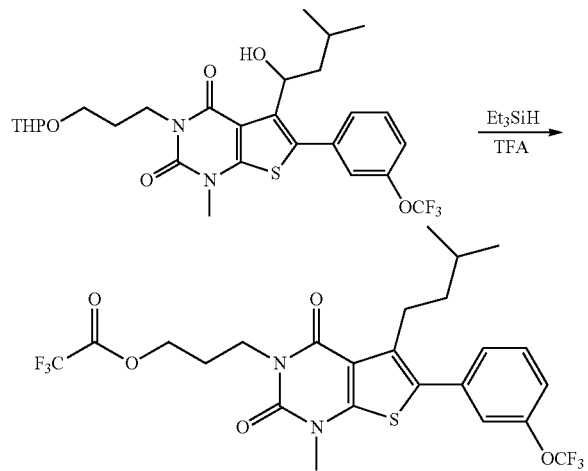

To a solution of 5-(1-hydroxy-3-methylbutyl)-1-methyl-3-(3-((tetrahydro-2H-pyran-2-yl)oxy) propyl)-6-(3-(trifluoromethoxy)phenyl)thieno[2,3-d]pyrimidine-2,4(1H,3H)-dione (See Compound 22, Step 3, 40 mg, 0.070 mmol) in TFA (2 mL) was added triethylsilane (1 mL). The reaction was stirred at RT for 48 h then diluted with DCM (5 mL) and water (5 mL). The organic layer was dried over $Na_2SO_4$ and concentrated to give 3-(5-isopentyl-1-methyl-2,4-dioxo-6-(3-(trifluoromethoxy)phenyl)-1,2-dihydrothieno[2,3-d]pyrimidin-3 (4H)-yl)propyl 2,2,2-trifluoroacetate (35 mg, 88.1% yield) as an oil. LCMS: $MH^+$ 567 and $T_R$=2.383 min.

Step 2 3-(3-hydroxypropyl)-5-isopentyl-1-methyl-6-(3-(trifluoromethoxy)phenyl)thieno[2,3-d]pyrimidine-2,4(1H,3H)-dione

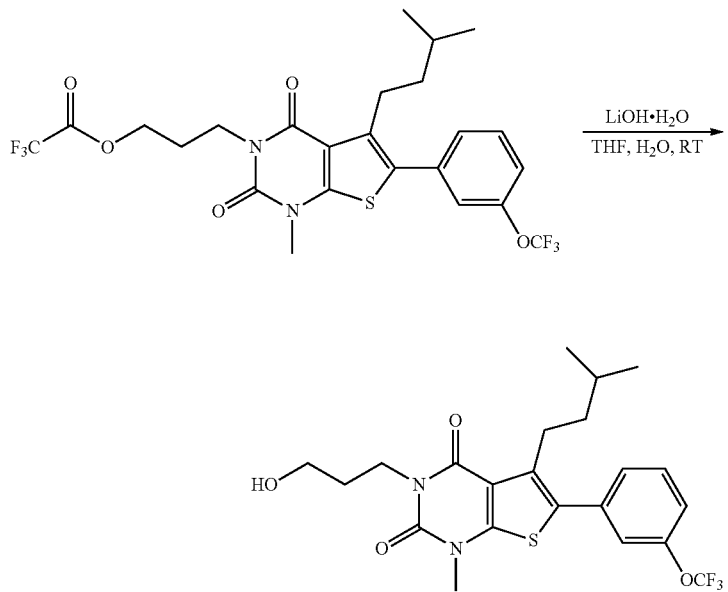

To a solution of 3-(5-isopentyl-1-methyl-2,4-dioxo-6-(3-(trifluoromethoxy)phenyl)-1,2-dihydro thieno[2,3-d]pyrimidin-3(4H)-yl)propyl 2,2,2-trifluoroacetate (35 mg, 0.062 mmol) in THF (4 mL) and water (4 mL) was added $LiOH.H_2O$ (5.19 mg, 0.123 mmol). The reaction was stirred at RT for 15 min then diluted with DCM (5 mL) and water (5 mL). The organic layer was dried over $Na_2SO_4$ and concentrated to a residue which was purified by Prep HPLC to give 3-(3-hydroxypropyl)-5-isopentyl-1-methyl-6-(3-(trifluoromethoxy)phenyl)thieno[2,3-d]pyrimidine-2,4(1H, 3H)-dione (15 mg, 51.6% yield) as a white solid. $^1H$ NMR (DMSO-$d_6$) δ: 7.65 (t, J=8.0 Hz, 1H), 7.47 (dd, J=12.5, 8.3 Hz, 2H), 7.41 (s, 1H), 4.49 (s, 1H), 4.02-3.89 (m, 2H), 3.47 (s, 5H), 2.91-2.78 (m, 2H), 1.78-1.63 (m, 2H), 1.51 (dd, J=12.4 and 6.0 Hz, 1H), 1.48-1.37 (m, 2H), 0.81 (d, J=6.4 Hz, 6H). LCMS: $MH^+$ 471 and $T_R$=3.347 min.

Compound 4

6-(3-chlorophenyl)-5-((4-chlorophenyl) (hydroxy) methyl)-3-(3-hydroxypropyl)-1-methylthieno[2,3-d] pyrimidine-2,4(1H,3H)-dione

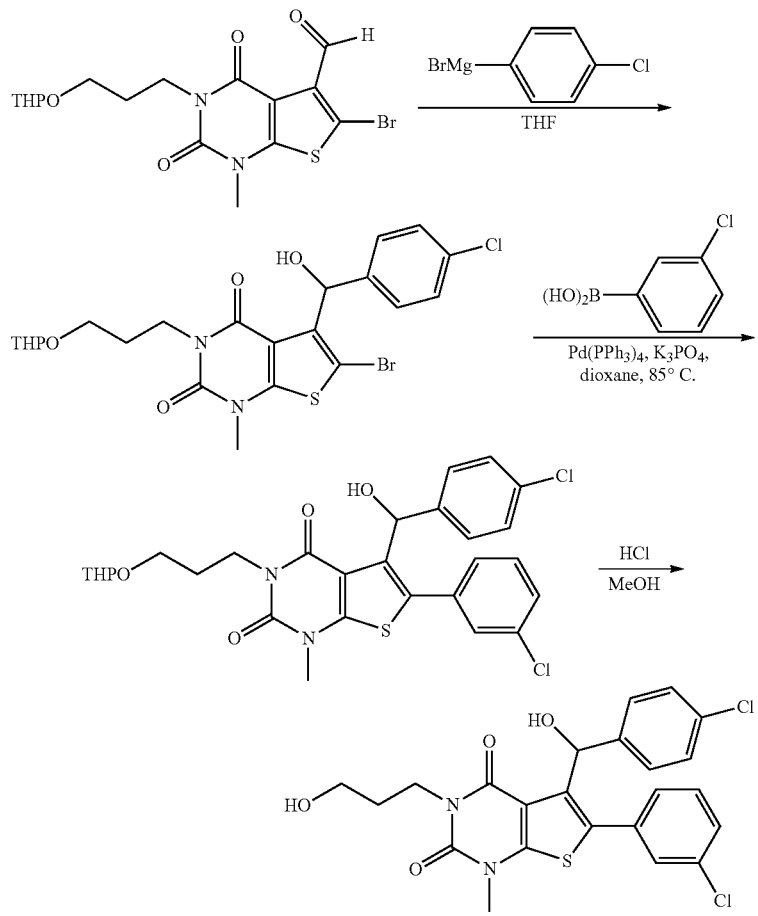

Step 1 6-bromo-5-((4-chlorophenyl)(hydroxy) methyl)-1-methyl-3-(3-((tetrahydro-2H-pyran-2-yl) oxy) propyl)thieno[2,3-d]pyrimidine-2,4(1H,3H)-dione

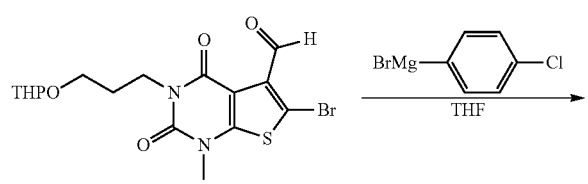

-continued

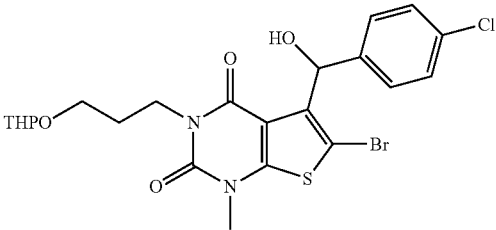

To a solution of 6-bromo-1-methyl-2,4-dioxo-3-(3-((tetrahydro-2H-pyran-2-yl)oxy)propyl)-1,2,3,4-tetrahydrothieno[2,3-d]pyrimidine-5-carbaldehyde (See Compound 2, Step 4, 185 mg, 0.428 mmol) in THF (5 mL) was added (4-chlorophenyl)magnesium bromide (0.77 mL, 0.772 mmol). The reaction was stirred for 5 min, diluted with water (10 mL) and extracted with DCM (3×10 mL). The combined organic layers were dried over $Na_2SO_4$ and concentrated to a residue which was purified by chromatography eluted with PE/EA (5:1 to 1:1) to give 6-bromo-5-((4-chlorophenyl) (hydroxy)methyl)-1-methyl-3-(3-((tetrahydro-2H-pyran-2-yl)oxy)propyl)thieno[2,3-d]-pyrimidine-2,4(1H,3H)-dione (120 mg, 51.4% yield) as a solid. LCMS: [M$^+$-THP-OH] 441 and $T_R$=2.021 min.

Step 2 6-(3-chlorophenyl)-5-((4-chlorophenyl)(hydroxy)methyl)-1-methyl-3-(3-((tetrahydro-2H-pyran-2-yl)oxy)propyl)thieno[2,3-d]pyrimidine-2,4(1H,3H)-dione

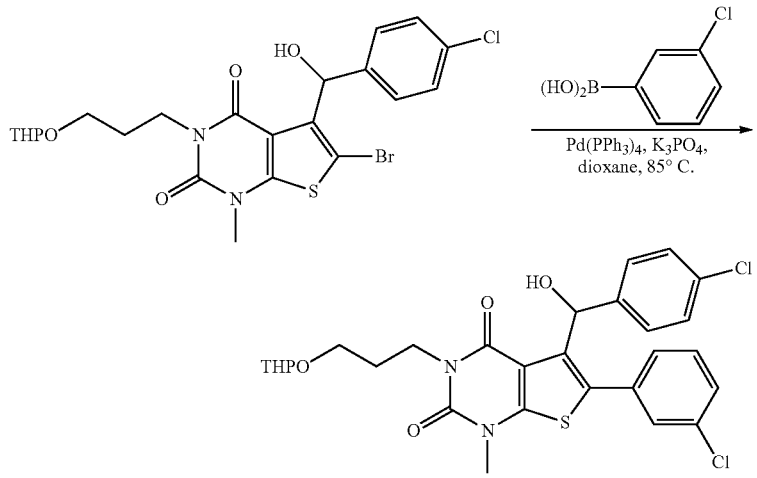

To a solution of 6-bromo-5-((4-chlorophenyl)(hydroxy)methyl)-1-methyl-3-(3-((tetrahydro-2H-pyran-2-yl)oxy)propyl)thieno[2,3-d]pyrimidine-2,4(1H,3H)-dione (50 mg, 0.091 mmol), (3-chlorophenyl)boronic acid (28.7 mg, 0.183 mmol) and aq. 2 M $K_3PO_4$ (0.4 mL) in dioxane (2 mL) was added Pd(PPh$_3$)$_4$ (10 mg). The reaction was heated at 85° C. for 2 h, cooled to RT, filtered and the filtrate was diluted DCM (10 mL) and water (10 mL). The organic layer was dried over $Na_2SO_4$ and concentrated to a residue which was purified by chromatography eluted with PE/EA (10:1 to 3:1) to give 6-(3-chlorophenyl)-5-((4-chlorophenyl)(hydroxy)methyl)-1-methyl-3-(3-((tetra hydro-2H-pyran-2-yl)oxy)propyl)thieno[2,3-d]pyrimidine-2,4(1H,3H)-dione (40 mg, 75.6% yield) as a solid. LCMS: [M$^+$-THP-OH] 473 and T$_R$=2.215 min.

Step 3 6-(3-chlorophenyl)-5-((4-chlorophenyl)(hydroxy)methyl)-3-(3-hydroxypropyl)-1-methylthieno[2,3-d]pyrimidine-2,4(1H,3H)-dione

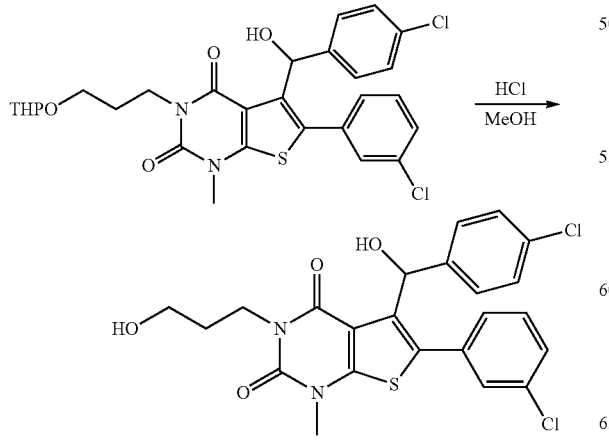

A solution of 6-(3-chlorophenyl)-5-((4-chlorophenyl)(hydroxy)methyl)-1-methyl-3-(3-((tetra hydro-2H-pyran-2-yl)oxy)propyl)thieno[2,3-d]pyrimidine-2,4(1H,3H)-dione (30 mg, 0.052 mmol) in 2N HCl/MeOH (5 mL) was stirred at RT for 1 h. The reaction was concentrated to a residue which was purified by Prep HPLC to give 6-(3-chlorophenyl)-5-((4-chlorophenyl) (hydroxy)methyl)-3-(3-hydroxypropyl)-1-methylthieno[2,3-d]pyrimidine-2,4(1H,3H)-dione (12 mg, 46.8% yield) as a white solid. $^1$H NMR (DMSO-d$_6$) δ: 7.53-7.36 (m, 3H), 7.29 (t, J=7.2 Hz, 3H), 7.19 (d, J=8.4 Hz, 2H), 6.32 (d, J=9.1 Hz, 1H), 6.14 (d, J=9.0 Hz, 1H), 4.47 (t, J=5.2 Hz, 1H), 3.92 (t, J=7.3 Hz, 2H), 3.51 (s, 3H), 3.42 (dd, J=11.6, 6.2 Hz, 2H), 1.68 (d, J=6.4 Hz, 2H). LCMS: [M$^+$-OH] 473 and T$_R$=3.107 min.

Parallel Synthesis Targets

Intermediate 1

6-bromo-3-(3-hydroxypropyl)-1,5-dimethylthieno[2,3-d]pyrimidine-2,4(1H,3H)-dione

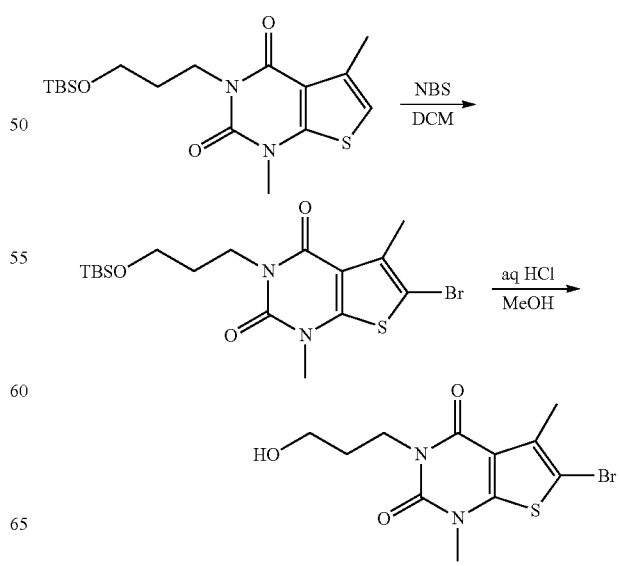

Step 1 6-bromo-3-(3-(tert-butyldimethylsilyloxy)propyl)-1,5-dimethylthieno[2,3-d]pyrimidine-2,4(1H,3H)-dione

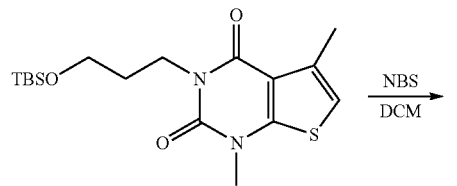

To a solution of 3-(3-(tert-butyldimethylsilyloxy)propyl)-1,5-dimethylthieno[2,3-d]pyrimidine-2,4(1H,3H)-dione (3.0 g, 8.14 mmol) in DCM (30 mL) at 0° C. was added NBS (1.6 g, 8.95 mmol). The reaction was stirred at 0° C. for 2 h then diluted with DCM (100 mL) and washed with water (2×50 mL). The organic layer was dried over $Na_2SO_4$ and concentrated to a residue which was purified by chromatography PE/EA (1:1) to give 6-bromo-3-(3-(tert-butyldimethylsilyloxy) propyl)-1,5-dimethylthieno[2,3-d]pyrimidine-2,4(1H,3H)-dione (3.4 g, 93.4% yield) as a white solid. LCMS: $MH^+$ 448 and $T_R$=2.917 min.

Step 2 6-bromo-3-(3-hydroxypropyl)-1,5-dimethylthieno[2,3-d]pyrimidine-2,4(1H,3H)-dione

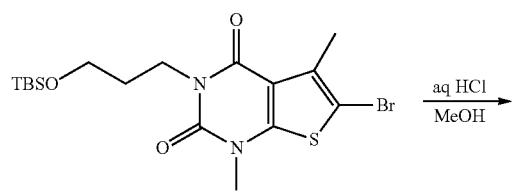

6-bromo-3-(3-(tert-butyldimethylsilyloxy)propyl)-1,5-dimethylthieno[2,3-d]pyrimidine-2,4 (1H,3H)-dione (2.4 g, 4.39 mmol) was dissolved in aq. 6N HCl (15 mL) and MeOH (15 mL). The reaction was stirred at RT for 30 min then diluted with DCM (20 mL) and washed with water (2×20 mL). The organic layer was dried over $Na_2SO_4$ and concentrated to give 6-bromo-3-(3-hydroxypropyl)-1,5-dimethylthieno[2,3-d]pyrimidine-2,4(1H,3H)-dione (1.7 g, 95.5% yield) as a white solid. LCMS: $MH^+$ 334 and $T_R$=1.049 min. Used without further purification.

Compound 5

6-(3,4-dichlorophenyl)-3-(3-hydroxypropyl)-1,5-dimethylthieno[2,3-d]pyrimidine-2,4(1H,3H)-dione

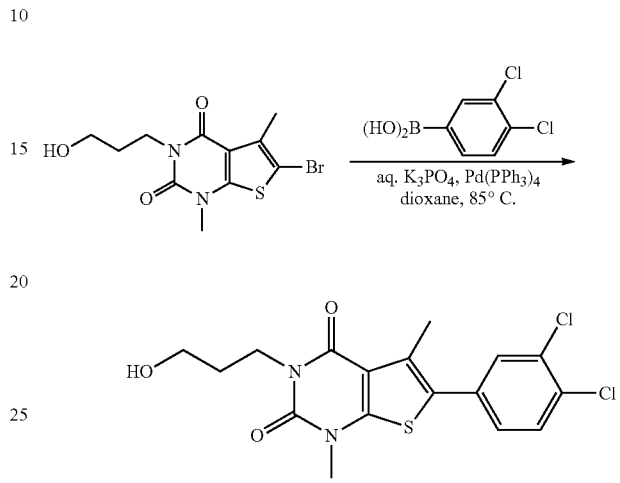

To a solution of 6-bromo-3-(3-hydroxypropyl)-1,5-dimethylthieno[2,3-d]pyrimidine-2,4(1H,3H)-dione (50 mg, 0.15 mmol) in dioxane (2 mL) was added 3,4-dichlorophenylboronic acid (57.3 mg, 0.3 mmol), $Pd(PPh_3)_4$ (17.3 mg, 0.015 mmol) and aq. 2M $K_3PO_4$ (0.4 mL). The reaction was heated at 85° C. for 1 h, cooled to RT then diluted with EA (20 mL). The organic layer was washed with brine (20 mL) and aq. $NH_4Cl$ (20 mL), dried with $Na_2SO_4$ and concentrated to a residue which was purified by Prep HPLC to give 6-(3,4-dichlorophenyl)-3-(3-hydroxypropyl)-1,5-dimethylthieno[2,3-d]pyrimidine-2,4(1H,3H)-dione (15.0 mg, 27.4% yield) as a white solid. $^1$H NMR (CDCl$_3$) δ: 7.55-7.48 (m, 2H), 7.24 (d, J=2.1 Hz, 1H), 4.27-4.14 (m, 2H), 3.60-3.50 (m, 5H), 3.27 (t, J=6.5 Hz, 1H), 2.54 (s, 3H), 2.00-1.85 (m, 2H). LCMS: $MH^+$ 399 and $T_R$=3.000 min.

The following Compounds 6 to 19 were prepared by substantially the same method as in Compound 5.

Compound 6

6-(4-fluoro-3-(trifluoromethyl)phenyl)-3-(3-hydroxypropyl)-1,5-dimethylthieno[2,3-d]pyrimidine-2,4(1H,3H)-dione

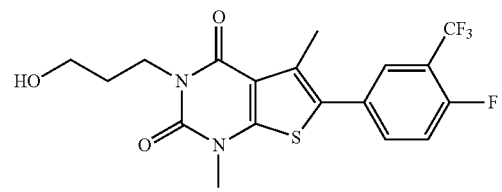 [SMILES: Cc1c(-c2ccc(F)c(C(F)(F)F)c2)sc2c1c(=O)n(CCCO)c(=O)n2C]

LCMS: $MH^+$ 417 and $T_R$=2.832 min

Compound 7

3-(3-hydroxypropyl)-1,5-dimethyl-6-(naphthalen-2-yl)thieno[2,3-d]pyrimidine-2,4(1H,3H)-dione

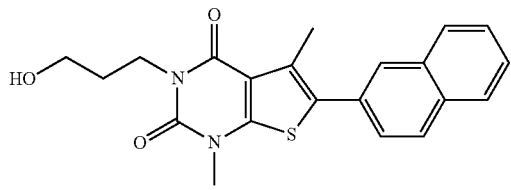 [SMILES: Cc1c(-c2ccc3ccccc3c2)sc2c1c(=O)n(CCCO)c(=O)n2C]

LCMS: MH$^+$ 381 and T$_R$=2.887 min

Compound 8

6-(5-chloropyridin-3-yl)-3-(3-hydroxypropyl)-1,5-dimethylthieno[2,3-d]pyrimidine-2,4(1H,3H)-dione

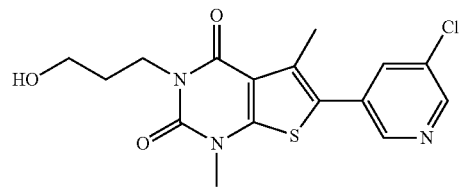 [SMILES: Cc1c(-c2cncc(Cl)c2)sc2c1c(=O)n(CCCO)c(=O)n2C]

LCMS: MH$^+$ 366 and T$_R$=2.227 min

Compound 10

6-(2,3-difluorophenyl)-3-(3-hydroxypropyl)-1,5-dimethylthieno[2,3-d]pyrimidine-2,4(1H,3H)-dione

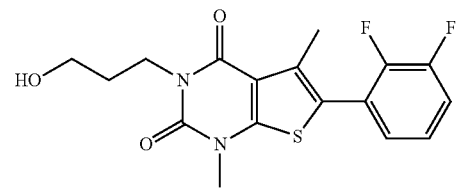 [SMILES: Cc1c(-c2cccc(F)c2F)sc2c1c(=O)n(CCCO)c(=O)n2C]

LCMS: MH$^+$ 367 and T$_R$=2.528 min

Compound 11

3-(3-hydroxypropyl)-1,5-dimethyl-6-(4-(trifluoromethyl)phenyl)thieno[2,3-d]pyrimidine-2,4(1H,3H)-dione

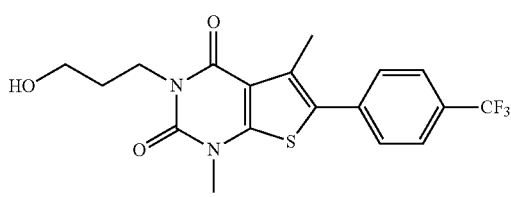 [SMILES: Cc1c(-c2ccc(C(F)(F)F)cc2)sc2c1c(=O)n(CCCO)c(=O)n2C]

LCMS: MH$^+$ 399 and T$_R$=2.849 min

Compound 12

3-(3-hydroxypropyl)-1,5-dimethyl-6-(4-(trifluoromethoxy)phenyl)thieno[2,3-d]pyrimidine-2,4(1H,3H)-dione

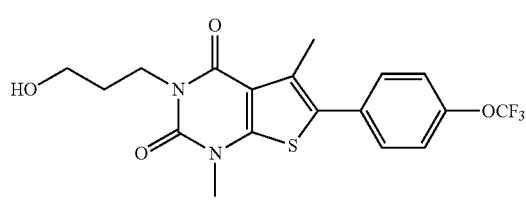 [SMILES: Cc1c(-c2ccc(OC(F)(F)F)cc2)sc2c1c(=O)n(CCCO)c(=O)n2C]

LCMS: MH$^+$ 415 and T$_R$=2.917 min

Compound 13

3-(3-hydroxypropyl)-1,5-dimethyl-6-(2-(trifluoromethoxy)phenyl)thieno[2,3-d]pyrimidine-2,4(1H,3H)-dione

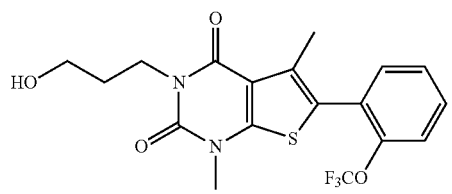 [SMILES: Cc1c(-c2ccccc2OC(F)(F)F)sc2c1c(=O)n(CCCO)c(=O)n2C]

LCMS: MH$^+$ 415 and T$_R$=2.776 min

Compound 14

3-(3-hydroxypropyl)-1,5-dimethyl-6-(3-(trifluoromethoxy)phenyl)thieno[2,3-d]pyrimidine-2,4(1H,3H)-dione

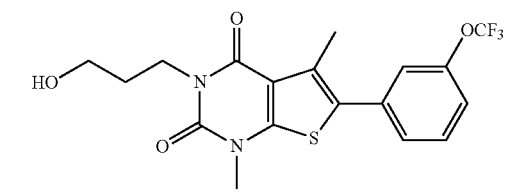 [SMILES: Cc1c(-c2cccc(OC(F)(F)F)c2)sc2c1c(=O)n(CCCO)c(=O)n2C]

LCMS: MH$^+$ 415 and T$_R$=2.903 min

Compound 15

6-(3,4-difluorophenyl)-3-(3-hydroxypropyl)-1,5-dimethylthieno[2,3-d]pyrimidine-2,4(1H,3H)-dione

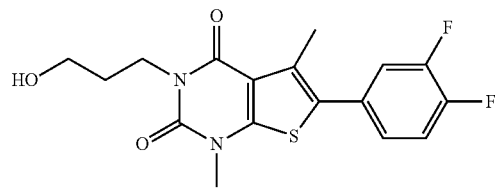 [SMILES: Cc1c(-c2ccc(F)c(F)c2)sc2c1c(=O)n(CCCO)c(=O)n2C]

LCMS: MH$^+$ 367 and T$_R$=2.656 min

Compound 16

6-(2-chlorophenyl)-3-(3-hydroxypropyl)-1,5-dimethylthieno[2,3-d]pyrimidine-2,4(1H,3H)-dione

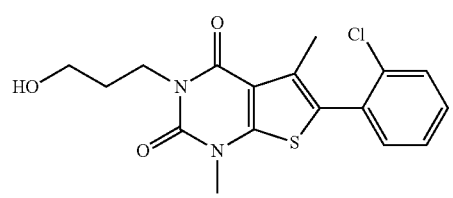 [SMILES: Cc1c(-c2ccccc2Cl)sc2c1c(=O)n(CCCO)c(=O)n2C]

LCMS: MH$^+$ 365 and T$_R$=2.627 min

Compound 17

6-(2,3-dichlorophenyl)-3-(3-hydroxypropyl)-1,5-dimethylthieno[2,3-d]pyrimidine-2,4(1H,3H)-dione

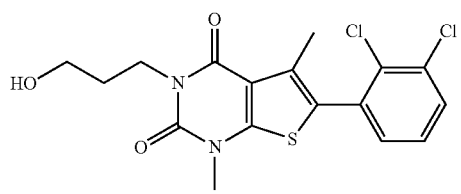 [SMILES: Cc1c(-c2cccc(Cl)c2Cl)sc2c1c(=O)n(CCCO)c(=O)n2C]

LCMS: MH$^+$ 400 and T$_R$=2.820 min

Compound 18

6-(3-fluorophenyl)-3-(3-hydroxypropyl)-1,5-dimethylthieno[2,3-d]pyrimidine-2,4(1H,3H)-dione

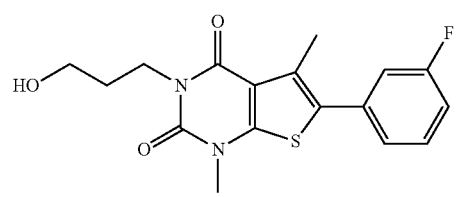 [SMILES: Cc1c(-c2cccc(F)c2)sc2c1c(=O)n(CCCO)c(=O)n2C]

LCMS: MH$^+$ 349 and T$_R$=2.473 min

Compound 19

6-(3-chlorophenyl)-3-(3-hydroxypropyl)-1,5-dimethylthieno[2,3-d]pyrimidine-2,4(1H,3H)-dione

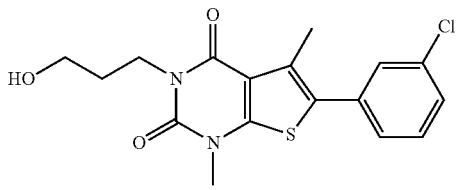 [SMILES: Cc1c(-c2cccc(Cl)c2)sc2c1c(=O)n(CCCO)c(=O)n2C]

LCMS: MH$^+$ 365 and T$_R$=2.678 min

Compound 20

3-(3-hydroxypropyl)-1-methyl-5-(3-methylbutanoyl)-6-(3-(trifluoromethoxy)phenyl)thieno[2,3-d]pyrimidine-2,4(1H,3H)-dione

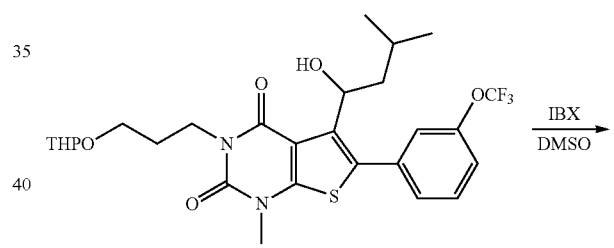

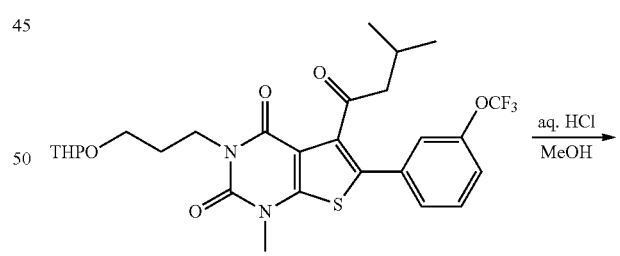

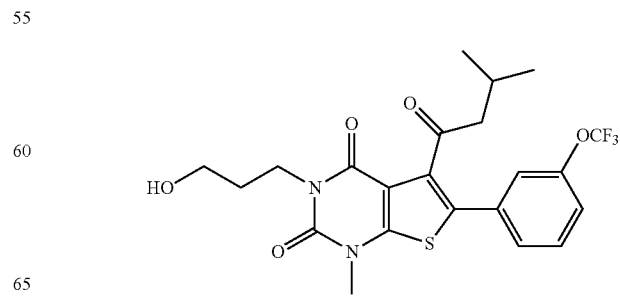

Step 1 1-methyl-5-(3-methylbutanoyl)-3-(3-((tetrahydro-2H-pyran-2-yl)oxy)propyl)-6-(3-(trifluoromethoxy)phenyl)thieno[2,3-d]pyrimidine-2,4(1H,3H)-dione Step 2 3-(3-hydroxypropyl)-1-methyl-5-(3-methylbutanoyl)-6-(3-(trifluoromethoxy)phenyl)thieno[2,3-d]pyrimidine-2,4(1H,3H)-dione

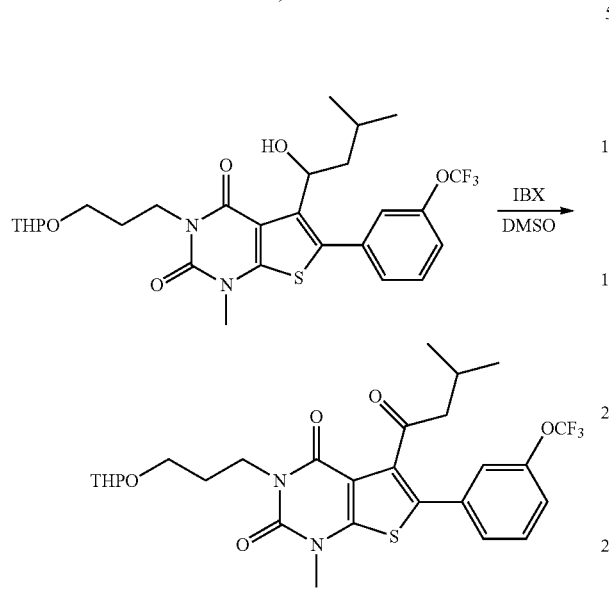

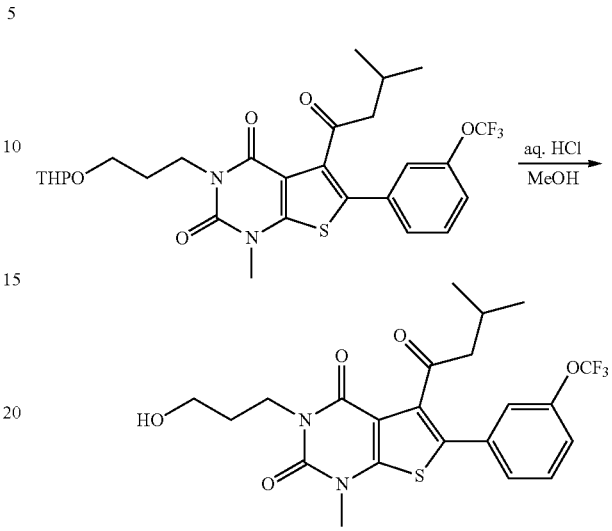

To a solution of 5-(1-hydroxy-3-methylbutyl)-1-methyl-3-(3-((tetrahydro-2H-pyran-2-yl)oxy) propyl)-6-(3-(trifluoromethoxy)phenyl)thieno[2,3-d]pyrimidine-2,4(1H,3H)-dione (See Compound 22, Step 3, 50 mg, 0.088 mmol) in DMSO (5 mL) was added 2-iodoxybenzoic acid (49.1 mg, 0.176 mmol). The reaction was heated at 50° C. for 2 h, cooled to RT, diluted with water (20 mL) and extracted with EA (3×10 mL). The combined organic layers were washed with aq. NH$_4$Cl (5 mL), dried over Na$_2$SO$_4$ and concentrated to a residue which was purified by chromatography eluted with PE/EA (5:1 to 1:1) to give 1-methyl-5-(3-methylbutanoyl)-3-(3-((tetrahydro-2H-pyran-2-yl)oxy)propyl)-6-(3-(trifluoromethoxy)phenyl)thieno[2,3-d]pyrimidine-2,4(1H, 3H)-dione (30 mg, 60.2% yield) as an oil. LCMS: MH$^+$ 569 and T$_R$=2.186 min.

A solution of 1-methyl-5-(3-methylbutanoyl)-3-(3-((tetrahydro-2H-pyran-2-yl)oxy)propyl)-6-(3-(trifluoromethoxy)phenyl)thieno[2,3-d]pyrimidine-2,4(1H,3H)-dione (30 mg, 0.053 mmol) in concentrated HCl (1 mL) and MeOH (5 mL) was stirred at RT for 1 h then concentrated to a residue which was purified by Prep HPLC to give 3-(3-hydroxypropyl)-1-methyl-5-(3-methylbutanoyl)-6-(3-(trifluoromethoxy)phenyl)thieno[2,3-d]pyrimidine-2,4(1H, 3H)-dione (6 mg, 23.4% yield) as a white solid. $^1$H NMR (CDCl$_3$) δ: 7.48-7.37 (m, 2H), 7.32 (s, 1H), 7.26-7.23 (m, 1H), 4.18 (t, J=6.1 Hz, 2H), 3.61 (s, 3H), 3.55 (dd, J=11.7, 6.3 Hz, 2H), 3.04 (t, J=7.0 Hz, 1H), 2.54 (d, J=6.6 Hz, 2H), 2.14 (dt, J=13.3, 6.7 Hz, 1H), 1.97-1.85 (m, 2H), 0.84 (d, J=6.7 Hz, 7H). LCMS: MH$^+$ 485 and T$_R$=3.100 min.

Compound 21

5-((4-chlorophenyl)(hydroxy)methyl)-3-(3-hydroxypropyl)-1-methyl-6-(3-(trifluoromethoxy) phenoxy)thieno[2,3-d]pyrimidine-2,4(1H,3H)-dione

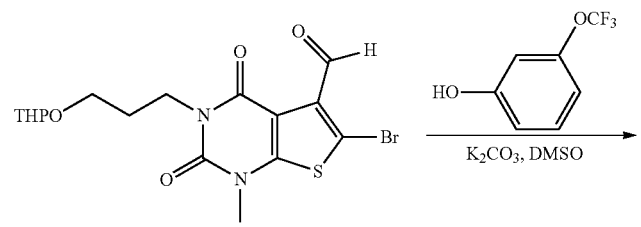

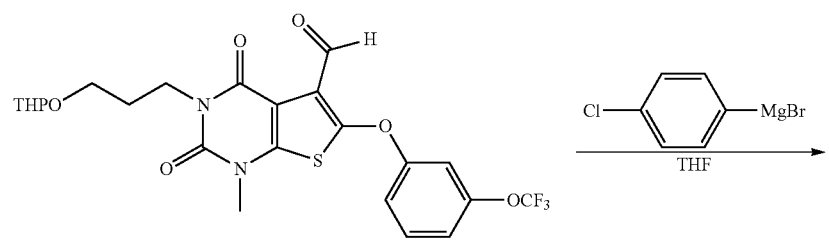

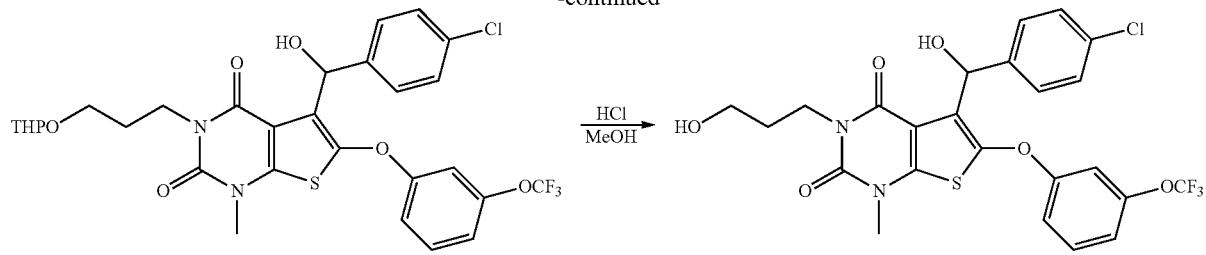

Step 1 1-methyl-2,4-dioxo-3-(3-((tetrahydro-2H-pyran-2-yl)oxy)propyl)-6-(3-(trifluoromethoxy)phenoxy)-1,2,3,4-tetrahydrothieno[2,3-d]pyrimidine-5-carbaldehyde

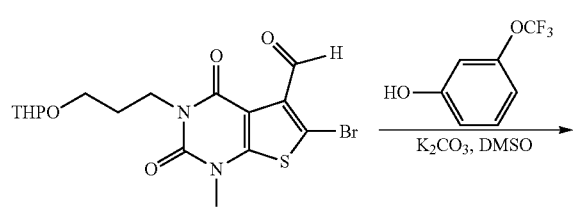

3-(trifluoromethoxy)phenol (82.6 mg, 0.464 mmol) and $K_2CO_3$ (96.1 mg, 0.696 mmol). The reaction was heated to 80° C. for 18 h, cooled to RT then diluted with EA (10 mL) and water (10 mL). The organic layer was washed with aq. 1N LiCl (3×5 mL), dried over $Na_2SO_4$ and concentrated to a residue which was purified by chromatography eluted with PE/EA (5:1 to 3:1) to give 1-methyl-2,4-dioxo-3-(3-((tetrahydro-2H-pyran-2-yl)oxy)propyl)-6-(3-(trifluoromethoxy)phenoxy)-1,2,3,4-tetrahydrothieno[2,3-d]pyrimidine-5-carbaldehyde (50 mg, 40.8% yield) as a solid. LCMS: [MH+-THP] 445 and $T_R$=1.834 min.

Step 2 5-((4-chlorophenyl)(hydroxy)methyl)-1-methyl-3-(3-((tetrahydro-2H-pyran-2-yl)oxy)propyl)-6-(3-(trifluoromethoxy)phenoxy)thieno[2,3-d]pyrimidine-2,4(1H,3H)-dione

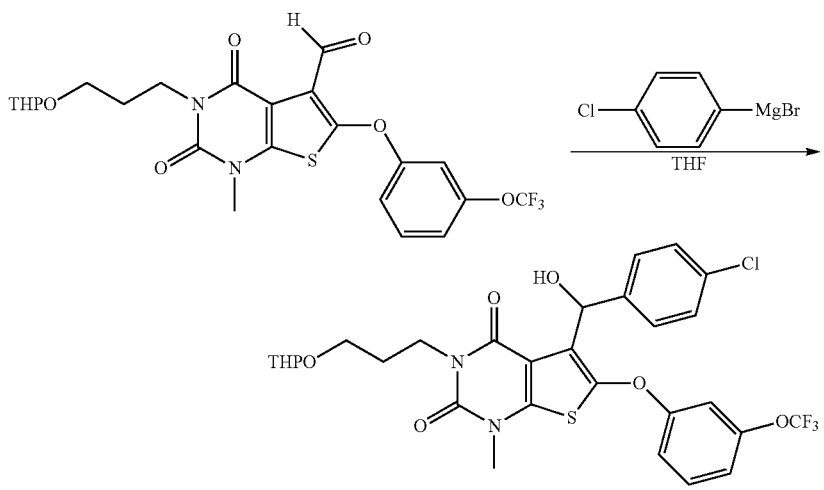

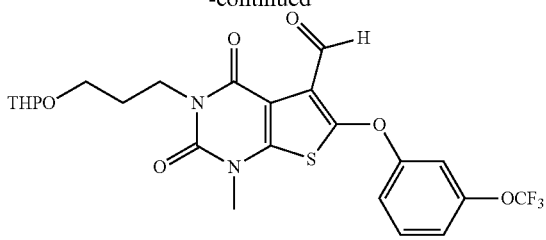

To a solution of 6-bromo-1-methyl-2,4-dioxo-3-(3-((tetrahydro-2H-pyran-2-yl)oxy)propyl)-1,2,3,4-tetrahydrothieno[2,3-d]pyrimidine-5-carbaldehyde (See Compound 2, Step 4, 100 mg, 0.232 mmol) in DMSO (2 mL) was added To a solution of 1-methyl-2,4-dioxo-3-(3-((tetrahydro-2H-pyran-2-yl)oxy)propyl)-6-(3-(trifluoro methoxy)phenoxy)-1,2,3,4-tetrahydrothieno[2,3-d]pyrimidine-5-carbaldehyde (50 mg, 0.095 mmol) in THF (2 mL) was added (4-chlorophenyl)magnesium bromide (0.19 mL, 0.190 mmol). The reaction was stirred for 2 min then diluted with DCM (5 mL) and water (5 mL). The organic layer was dried over $Na_2SO_4$ and concentrated to a residue which was purified by chromatography PE/EA (5:1 to 3:1) to give 5-((4-chlorophenyl)(hydroxy)methyl)-1-methyl-3-(3-((tetrahydro-2H-pyran-2-yl)oxy)propyl)-6-(3-(trifluoromethoxy)phenoxy)thieno[2,3-d]pyrimidine-2,4(1H,3H)-dione (30 mg, 49.5% yield) as a solid. LCMS: [M+-THP-OH] 539 and $T_R$=2.159 min.

Step 3 5-((4-chlorophenyl) (hydroxy)methyl)-3-(3-hydroxypropyl)-1-methyl-6-(3-(trifluoromethoxy)phenoxy)thieno[2,3-d]pyrimidine-2,4(1H,3H)-dione

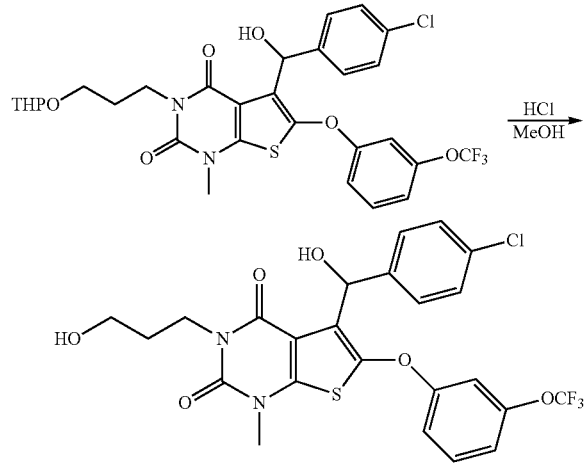

A solution of 5-((4-chlorophenyl)(hydroxy)methyl)-1-methyl-3-(3-((tetrahydro-2H-pyran-2-yl)oxy)propyl)-6-(3-(trifluoromethoxy)phenoxy)thieno[2,3-d]pyrimidine-2,4(1H,3H)-dione (30 mg, 0.047 mmol) in concentrated HCl (1 mL) and MeOH (5 mL) was stirred at RT for 1 h. The reaction was concentrated to a residue which was purified by Prep HPLC to give 5-((4-chlorophenyl) (hydroxy)methyl)-3-(3-hydroxypropyl)-1-methyl-6-(3-(trifluoromethoxy)phenoxy) thieno[2,3-d]pyrimidine-2,4(1H,3H)-dione (6 mg, 23.0% yield) as a white solid. $^1$H NMR (DMSO-$d_6$) δ: 7.47 (t, J=8.3 Hz, 1H), 7.34 (d, J=8.5 Hz, 2H), 7.26 (d, J=8.5 Hz, 2H), 7.10 (dd, J=28.1, 8.2 Hz, 2H), 6.98 (s, 1H), 6.33 (d, J=7.7 Hz, 1H), 6.16 (d, J=7.6 Hz, 1H), 4.51 (t, J=5.2 Hz, 1H), 3.95 (s, 2H), 3.45 (d, J=5.4 Hz, 2H), 3.41 (s, 3H), 1.71 (s, 2H). LCMS: [M$^+$-OH] 539 and $T_R$=3.084 min.

Compound 22

5-(1-hydroxy-3-methylbutyl)-3-(3-hydroxypropyl)-1-methyl-6-(3-(trifluoromethoxy)phenyl) thieno[2,3-d]pyrimidine-2,4(1H,3H)-dione

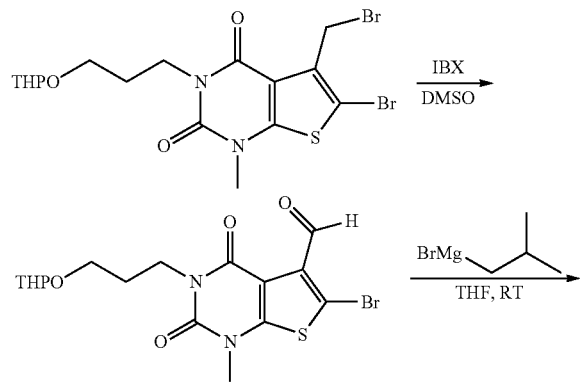

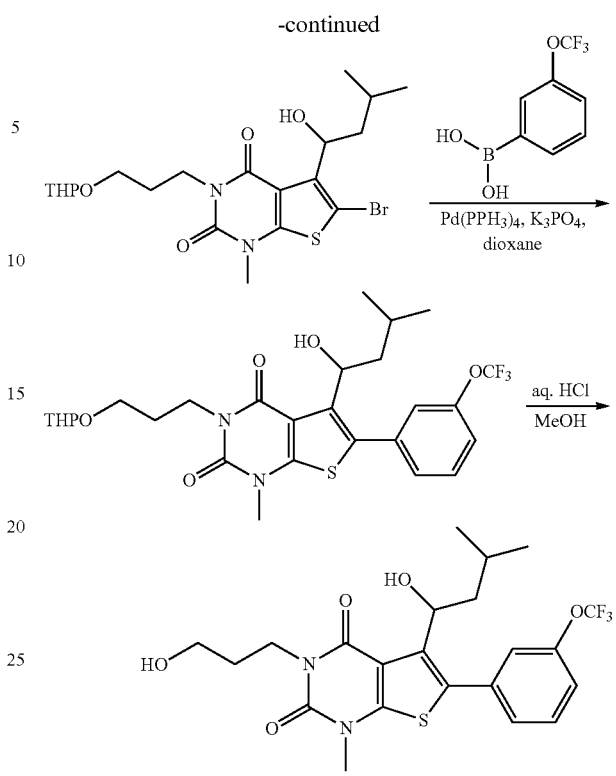

Step 1 Ethyl 6-bromo-1-methyl-2,4-dioxo-3-(3-((tetrahydro-2H-pyran-2-yl)oxy)propyl)-1,2,3,4 tetra hydrothieno[2,3-d]pyrimidine-5-carbaldehyde

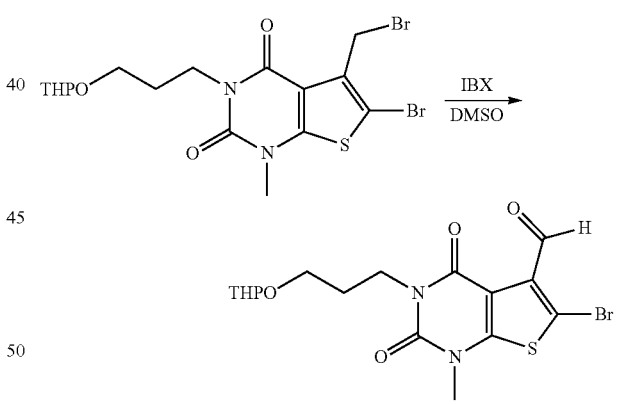

To a solution of 6-bromo-5-(bromomethyl)-1-methyl-3-(3-((tetrahydro-2H-pyran-2-yl)oxy) propyl)thieno[2,3-d]pyrimidine-2,4(1H,3H)-dione (See Compound 2, Step 3, 800 mg, 1.61 mmol) in DMSO (10 mL) was added 2-iodoxybenzoic acid (541.7 mg, 1.93 mmol). The reaction was heated at 50° C. for 1.5 h, cooled to RT, diluted with water (20 mL) and extracted with EA (3×10 mL). The combined organic layers were washed with aq. NH$_4$Cl (20 mL), dried over Na$_2$SO4 and concentrated to a residue which was purified by chromatography eluted with PE/EA (5:1 to 1:1) to give ethyl 6-bromo-1-methyl-2,4-dioxo-3-((tetrahydro-2H-pyran-2-yl)oxy)propyl)-1,2,3,4-tetrahydro thieno [2,3-d]pyrimidine-5-carbaldehyde (400 mg, 57.5% yield) as a white solid. LCMS: [MH$^+$-THP] 347 and $T_R$=1.665 min.

Step 2 6-bromo-5-(1-hydroxy-3-methylbutyl)-1-methyl-3-(3-((tetrahydro-2H-pyran-2-yl)oxy)propyl)thieno[2,3-d]pyrimidine-2,4(1H,3H)-dione

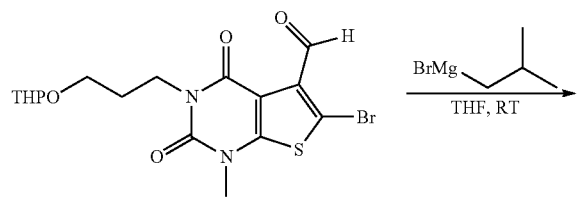

To a solution of 6-bromo-1-methyl-2,4-dioxo-3-(3-((tetrahydro-2H-pyran-2-yl)oxy)propyl)-1,2,3,4-tetrahydrothieno[2,3-d]pyrimidine-5-carbaldehyde (400 mg, 0.92 mmol) in THF (5 mL) was added isobutylmagnesium bromide (0.92 mL, 0.92 mmol) dropwise. The reaction was stirred at RT for 5 min then diluted with DCM (5 mL) and water (5 mL). The organic layer was dried over $Na_2SO_4$ and concentrated to a residue which was purified by chromatography eluted with PE/EA (5:1 to 1:1) to give 6-bromo-5-(1-hydroxy-3-methylbutyl)-1-methyl-3-(3-((tetrahydro-2H-pyran-2-yl)oxy)propyl)thieno[2,3-d]pyrimidine-2,4(1H,3H)-dione (70 mg, 15.4% yield) as a solid. LCMS: $MH^+$ 405 and $T_R$=1.922 min.

Step 3 5-(1-hydroxy-3-methylbutyl)-1-methyl-3-(3-((tetrahydro-2H-pyran-2-yl)oxy)propyl)-6-(3-(trifluoromethoxy)phenyl)thieno[2,3-d]pyrimidine-2,4(1H,3H)-dione

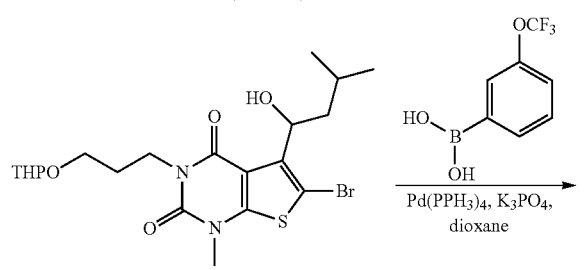

To a solution of 6-bromo-5-(1-hydroxy-3-methylbutyl)-1-methyl-3-(3-((tetrahydro-2H-pyran-2-yl)oxy)propyl)thieno[2,3-d]pyrimidine-2,4(1H,3H)-dione (70 mg, 0.143 mmol) in dioxane (2 mL) was added (3-(trifluoromethoxy)phenyl)boronic acid (58.9 mg, 0.286 mmol), Pd(PPh₃)₄ (10 mg) and aq. 2M $K_3PO_4$ (0.4 mL). The reaction was heated at 85° C. for 2 h then cooled to RT and filtered. The filtrate was diluted with DCM (10 mL) and water (10 mL). The organic layer was dried over $Na_2SO_4$ and concentrated to a residue which was purified by chromatography eluted with PE/EA (10:1 to 5:1) to give 5-(1-hydroxy-3-methylbutyl)-1-methyl-3-(3-((tetrahydro-2H-pyran-2-yl)oxy)propyl)-6-(3-(trifluoromethoxy)phenyl)thieno[2,3-d]pyrimidine-2,4(1H,3H)-dione (50 mg, 61.2% yield) as a solid. LCMS: $[MH^+$-THP] 487 and $T_R$=2.079 min.

Step 4 5-(1-hydroxy-3-methylbutyl)-3-(3-hydroxypropyl)-1-methyl-6-(3-(trifluoromethoxy)phenyl)thieno[2,3-d]pyrimidine-2,4(1H,3H)-dione

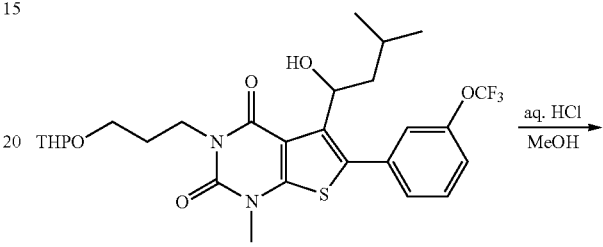

A solution of 5-(1-hydroxy-3-methylbutyl)-1-methyl-3-(3-((tetrahydro-2H-pyran-2-yl)oxy)propyl)-6-(3-(trifluoromethoxy)phenyl)thieno[2,3-d]pyrimidine-2,4(1H,3H)-dione (15 mg, 0.026 mmol) in concentrated HCl (1 mL) and MeOH (5 mL) was stirred at RT for 1 h. The reaction was concentrated to a residue which was purified by Prep HPLC to give 5-(1-hydroxy-3-methylbutyl)-3-(3-hydroxypropyl)-1-methyl-6-(3-(trifluoromethoxy)phenyl)thieno[2,3-d]pyrimidine-2,4(1H,3H)-dione (6 mg, 46.9% yield) as a white solid. $^1$H NMR (CDCl₃) δ: 7.49 (t, J=8.0 Hz, 1H), 7.35 (d, J=7.7 Hz, 1H), 7.29 (d, J=8.4 Hz, 1H), 5.39 (d, J=11.9 Hz, 1H), 4.85-4.65 (m, 1H), 4.26 (t, J=6.1 Hz, 2H), 3.70-3.49 (m, 5H), 2.89 (s, 1H), 2.06-1.89 (m, 3H), 1.76 (dt, J=13.4, 6.6 Hz, 1H), 1.43-1.33 (m, 1H), 0.80 (dd, J=9.3 and 6.7 Hz, 6H). LCMS: $MH^+$ 487 and $T_R$=2.971 min.

Compound 23

5-(4-chlorobenzyl)-6-(3-chlorophenyl)-3-(3-hydroxypropyl)-1-methylthieno[2,3-d]pyrimidine-2,4(1H,3H)-dione

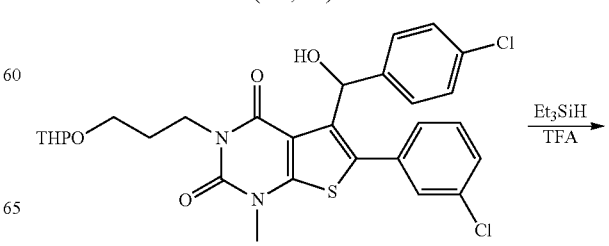

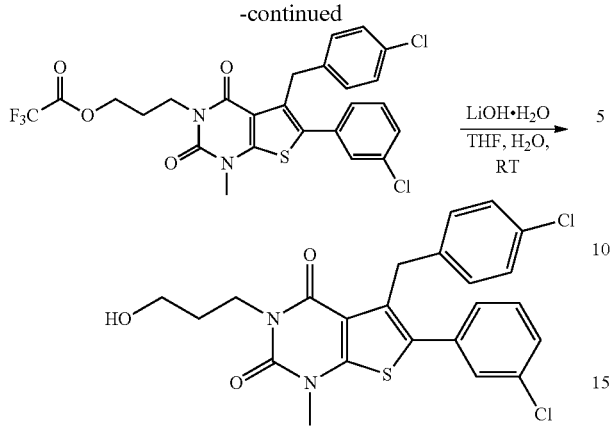

Step 1 3-(5-(4-chlorobenzyl)-6-(3-chlorophenyl)-1-methyl-2,4-dioxo-1,2-dihydrothieno[2,3-d]pyrimidin-3(4H)-yl)propyl 2,2,2-trifluoroacetate

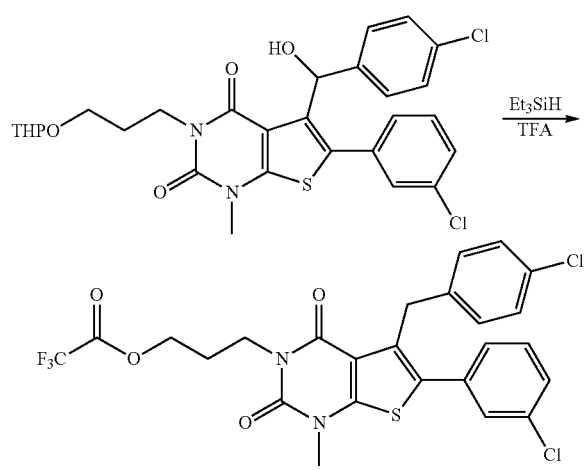

To a solution of 6-(3-chlorophenyl)-5-((4-chlorophenyl)(hydroxy)methyl)-1-methyl-3-(3-((tetra hydro-2H-pyran-2-yl)oxy)propyl)thieno[2,3-d]pyrimidine-2,4(1H,3H)-dione (See Compound 4, Step 2, 50 mg, 0.078 mmol) in TFA (1 mL) was added triethylsilane (0.5 mL). The reaction was stirred at RT for 2 h then diluted with DCM (5 mL) and water (5 mL). The organic layer was dried over Na$_2$SO$_4$ and concentrated to give 3-(5-(4-chlorobenzyl)-6-(3-chlorophenyl)-1-methyl-2,4-dioxo-1,2-dihydro thieno[2,3-d]pyrimidin-3(4H)-yl)propyl 2,2,2-trifluoroacetate (40 mg, 80.5% yield) as an oil. LCMS: MH$^+$ 571 and T$_R$=2.327 min. Used without further purification.

Step 2 5-(4-chlorobenzyl)-6-(3-chlorophenyl)-3-(3-hydroxypropyl)-1-methylthieno[2,3-d]pyrimidine-2,4(1H,3H)-dione

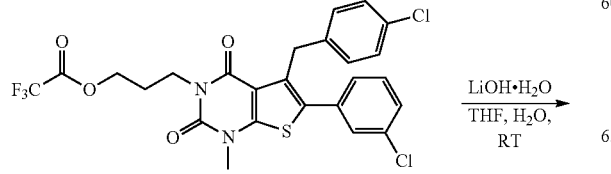

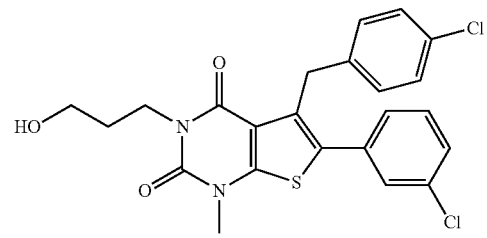

To a solution of 3-(5-(4-chlorobenzyl)-6-(3-chlorophenyl)-1-methyl-2,4-dioxo-1,2-dihydrothieno[2,3-d]pyrimidin-3(4H)-yl)propyl 2,2,2-trifluoroacetate (40 mg, 0.070 mmol) in THF (4 mL) and water (4 mL) was added LiOH.H$_2$O (5.88 mg, 0.14 mmol). The reaction was stirred at RT for 15 min then diluted with DCM (5 mL) and water (5 mL). The organic layer was dried over Na$_2$SO$_4$ and concentrated to a residue which was purified by Prep HPLC to give 5-(4-chlorobenzyl)-6-(3-chlorophenyl)-3-(3-hydroxypropyl)-1-methylthieno[2,3-d]pyrimidine-2,4(1H,3H)-dione (16 mg, 48.1% yield) as a white solid. $^1$H-NMR (DMSO-d$_6$) δ: 7.49 (d, J=5.1 Hz, 2H), 7.40 (s, 1H), 7.36-7.32 (m, 1H), 7.29 (d, J=8.4 Hz, 2H), 7.04 (d, J=8.4 Hz, 2H), 4.45 (t, J=5.2 Hz, 1H), 4.30 (s, 2H), 3.97-3.82 (m, 2H), 3.52 (d, J=14.8 Hz, 3H), 3.42 (dd, J=11.7, 6.3 Hz, 2H), 1.67 (dd, J=14.2, 6.9 Hz, 2H). LCMS: MH$^+$ 475 and T$_R$=3.252 min.

Compound 24

5-(4-chlorobenzyl)-6-(4-chlorophenyl)-3-(3-hydroxypropyl)-1-methylthieno[2,3-d]pyrimidine-2,4(1H,3H)-dione

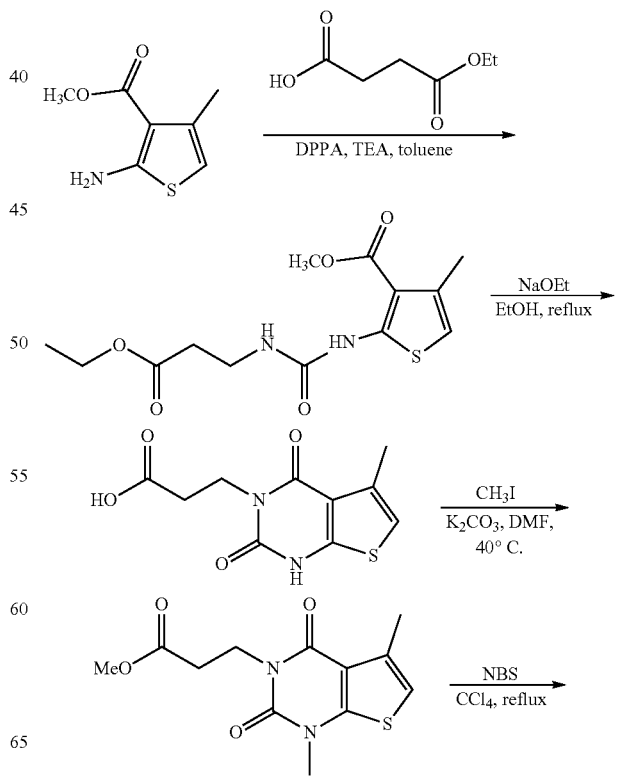

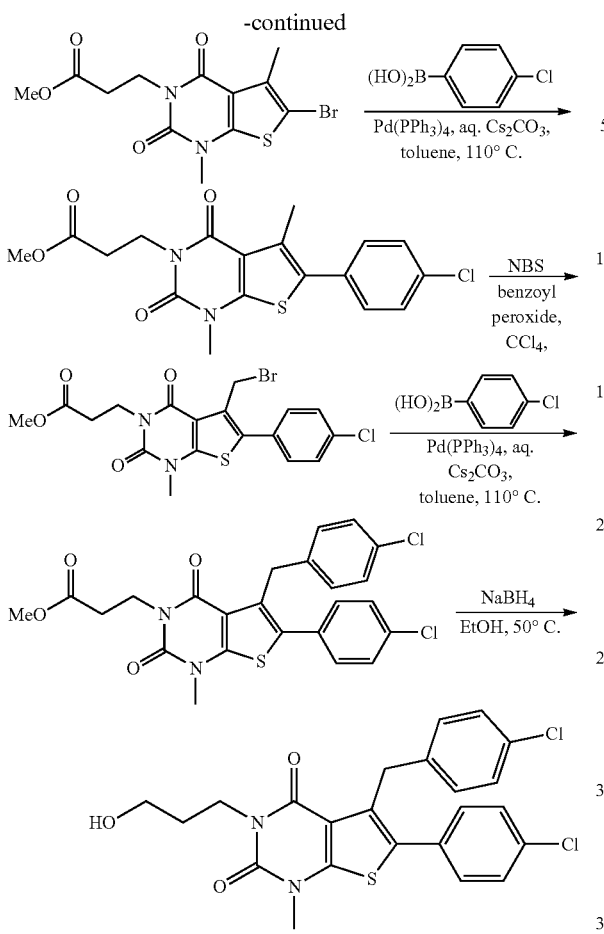

Step 1 Methyl 2-(3-(3-ethoxy-3-oxopropyl)ureido)-4-methylthiophene-3-carboxylate To a solution of 4-ethoxy-4-oxobutanoic acid (713 mg, 5.4 mmol) in toluene was added diphenylphosphoryl azide (1.48 g, 5.4 mmol) followed by TEA (600 mg, 5.94 mmol). The reaction was stirred at RT for 30 min then methyl 2-amino-4-methylthiophene-3-carboxylate (500 mg, 2.7 mmol) was added. The reaction was heated at reflux for 4 h, cooled to RT then diluted with EA (20 mL) and water (10 mL). The organic layer was washed with brine (10 mL), dried with $Na_2SO_4$ and concentrated to a residue which was purified by chromatography eluted with DCM/MeOH (50:1) to give 2-(3-(3-ethoxy-3-oxopropyl)ureido)-4-methylthiophene-3-carboxylate (470 mg, 55.3% yield) as a yellow solid. LCMS: $MH^+$ 315 and $T_R$=1.589 min.

Step 2 3-(5-methyl-2,4-dioxo-1,2-dihydrothieno[2,3-d]pyrimidin-3(4H)-yl)propanoic acid

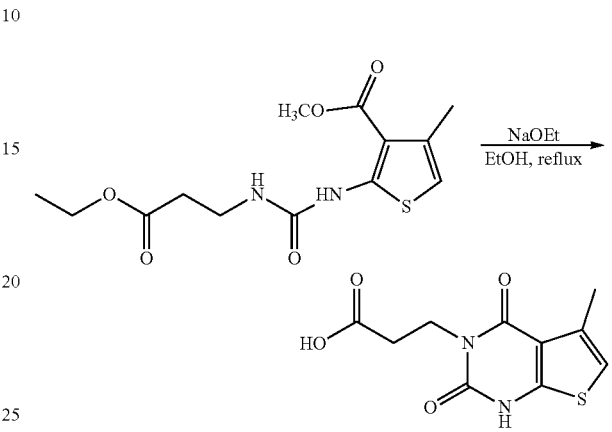

To a solution of 2-(3-(3-ethoxy-3-oxopropyl)ureido)-4-methylthiophene-3-carboxylate (470 mg, 1.5 mmol) in EtOH (10 mL) was added sodium ethoxide (203 mg, 2.19 mmol, freshly prepared). The reaction was heated at reflux for 4 h, concentrated, acidified with 1N HCl until PH=1 then extracted with EA (2×10 mL). The combined organic layers were dried over $Na_2SO_4$ and concentrated to give ethyl 3-(5-methyl-2,4-dioxo-1,2-dihydrothieno[2,3-d]pyrimidin-3(4H)-yl)propanoate (330 mg, 82% yield) as a yellow thick oil. LCMS: $MH^+$ 255 and $T_R$=0.718 min. Used without further purification.

Step 3 Methyl 3-(1,5-dimethyl-2,4-dioxo-1,2-dihydrothieno[2,3-d]pyrimidin-3 (4H)-yl)-propanoate

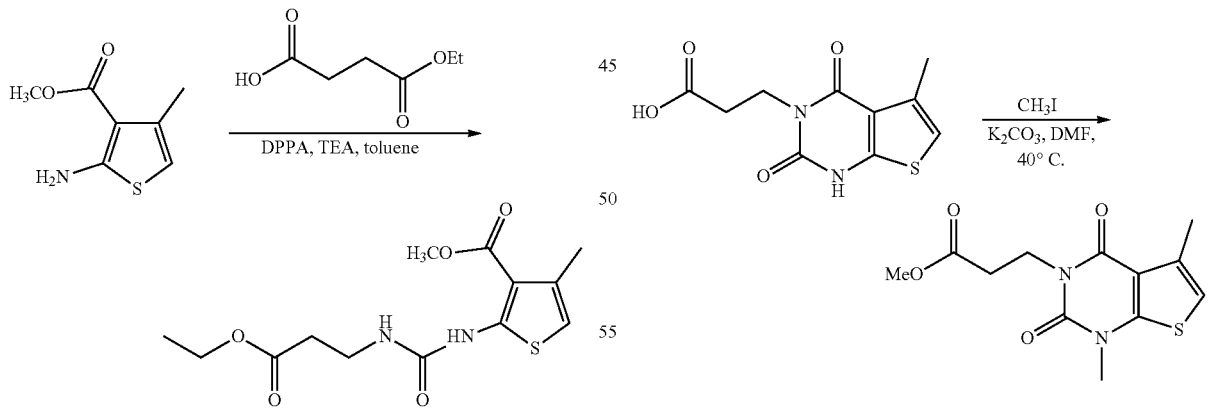

To a solution of 3-(5-methyl-2,4-dioxo-1,2-dihydrothieno[2,3-d]pyrimidin-3(4H)-yl)propanoic acid (330 mg, 1.17 mmol) in DMF (6 mL) was added $CH_3I$ (332 mg, 2.33 mmol) followed by $K_2CO_3$ (322 mg, 2.33 mmol). The reaction was heated in a sealed tube at 40° C. for 4 h, cooled to RT then diluted with EA (20 mL) and water (20 mL). The organic layer was washed with brine (10 mL), dried over $Na_2SO_4$ and concentrated to a residue which was purified by chromatography eluted with DCM/MeOH (50:1) to give methyl 3-(1,5-dimethyl-2,4-dioxo-1,2-dihydrothieno[2,3-d]pyrimidin-3(4H)-yl)propanoate (210 mg, 63.6% yield) as a yellow solid. LCMS: MH+ 283 and T$_R$=1.253 min.

Step 4 3-(6-bromo-1,5-dimethyl-2,4-dioxo-1,2-dihydrothieno[2,3-d]pyrimidin-3 (4H)-yl)propanoate

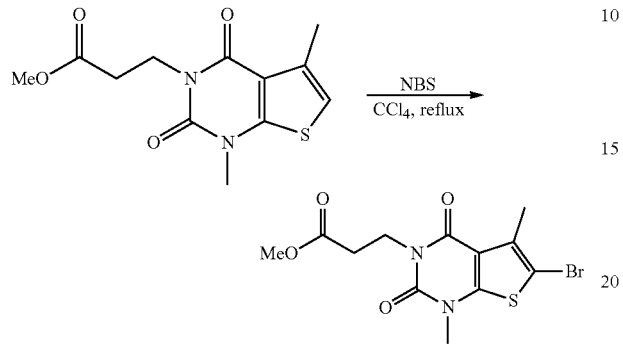

To a solution of methyl 3-(1,5-dimethyl-2,4-dioxo-1,2-dihydrothieno[2,3-d]pyrimidin-3(4H)-yl) propanoate (150 mg, 0.53 mmol) in CCl$_4$ (5 mL) was added NBS (95 mg, 0.53 mmol). The reaction was heated at reflux for 1 h, cooled to RT then diluted with DCM (10 mL) and water (10 mL). The organic layer was washed with aq. NaHCO$_3$ (10 mL), brine (10 mL), dried over Na$_2$SO$_4$ and concentrated to a residue which was purified by chromatography eluted with DCM/MeOH (80:1) to give methyl 3-(6-bromo-1,5-dimethyl-2,4-dioxo-1,2-dihydrothieno[2,3-d]pyrimidin-3(4H)-yl)propanoate (180 mg, 94% yield) as a yellow solid. LCMS: MH+ 361 and T$_R$=1.609 min.

Step 5 Methyl 3-(6-(4-chlorophenyl)-1,5-dimethyl-2,4-dioxo-1,2-dihydrothieno[2,3-d]pyrimidin-3 (4H)-yl)propanoate

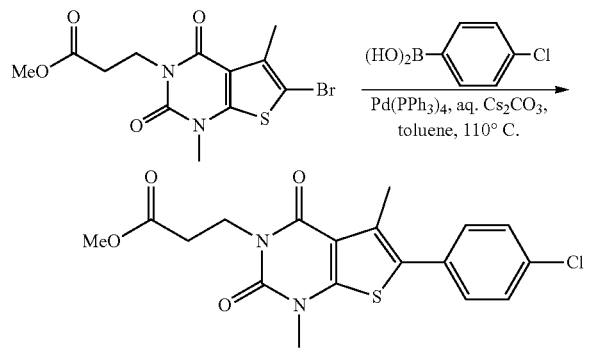

To a solution of methyl 3-(6-bromo-1,5-dimethyl-2,4-dioxo-1,2-dihydrothieno[2,3-d]pyrimidin-3(4H)-yl)propanoate (180 mg, 0.498 mmol) in toluene (5 mL) was added 4-chlorophenylboronic acid (78 mg, 0.498 mmol) and aq. Cs$_2$CO$_3$ solution (1 M, 1 mL). The reaction was degassed under nitrogen gas (3×) then Pd(PPh$_3$)$_4$ (10 mg) was added. The reaction was heated at 100° C. for 18 h, cooled to RT then diluted with EA (10 mL). The organic layer was washed with brine (10 mL), dried over Na$_2$SO$_4$ and concentrated to a residue which was purified by chromatography eluted with DCM/MeOH (80:1) to give methyl 3-(6-(4-chlorophenyl)-1,5-dimethyl-2,4-dioxo-1,2-dihydro thieno[2,3-d]pyrimidin-3(4H)-yl)propanoate (91 mg, 46.5% yield) as a yellow solid. LCMS: MH+ 393 and T$_R$=1.956 min.

Step 6 Methyl 3-(5-(bromomethyl)-6-(4-chlorophenyl)-1-methyl-2,4-dioxo-1,2-dihydrothieno[2,3-d]pyrimidin-3(4H)-yl)propanoate

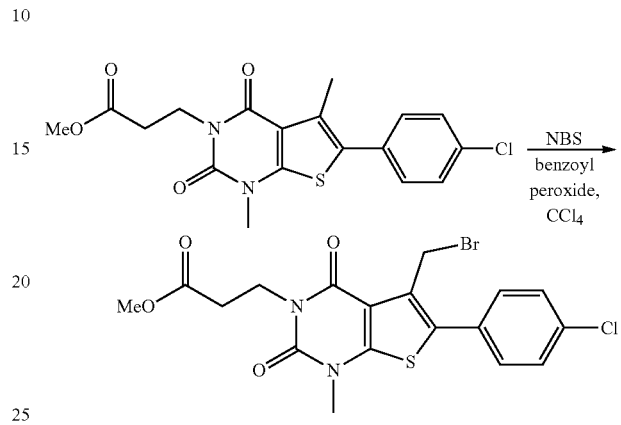

To a solution of methyl 3-(6-(4-chlorophenyl)-1,5-dimethyl-2,4-dioxo-1,2-dihydrothieno[2,3-d]pyrimidin-3(4H)-yl)propanoate (25 mg, 0.0636 mmol) in CCl$_4$ (1 mL) was added NBS (11.3 mg, 0.0636 mmol) followed by benzoyl peroxide (2 mg). The reaction was heated at reflux for 4 h, cooled to RT then diluted with DCM (10 mL). The mixture was washed with aq. NaHCO$_3$ (5 mL) and brine (10 mL). The organic layer was dried over Na$_2$SO$_4$ and concentrated to give methyl 3-(5-(bromomethyl)-6-(4-chlorophenyl)-1-methyl-2,4-dioxo-1,2-dihydrothieno[2,3-d]pyrimidin-3 (4H)-yl)propanoate (30 mg, 100% yield). LCMS: MH+ 473 and T$_R$=1.907 min. Used without further purification.

Step 7 Methyl 3-(5-(4-chlorobenzyl)-6-(4-chlorophenyl)-1-methyl-2,4-dioxo-1,2-dihydrothieno[2,3-d]pyrimidin-3(4H)-yl)propanoate

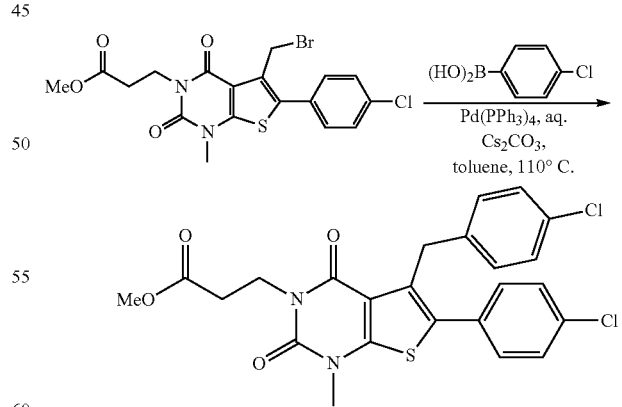

To a solution of methyl 3-(5-(bromomethyl)-6-(4-chlorophenyl)-1-methyl-2,4-dioxo-1,2-dihydrothieno[2,3-d]pyrimidin-3(4H)-yl)propanoate (30 mg, 0.064 mmol) in toluene (2 mL) was added (4-chlorophenyl)boronic acid (9.94 mg, 0.064 mmol) and aq. Cs$_2$CO$_3$ solution (1 M, 0.5 mL). The reaction was degassed under nitrogen gas (3×) then Pd(PPh₃)₄ (3 mg) was added. The reaction was heated at 100° C. for 18 h, cooled to RT then diluted with EA (10 mL). The organic layer was washed with brine (5 mL), dried over Na₂SO₄ and concentrated to a residue which was purified by Prep TLC eluted with PE/EA (1:1) to give methyl 3-(5-(4-chlorobenzyl)-6-(4-chlorophenyl)-1-methyl-2,4-dioxo-1,2-dihydrothieno[2,3-d]pyrimidin-3(4H)-yl)propanoate (13 mg, 40.6% yield) as a white solid. LCMS: MH⁺ 503 and T$_R$=2.145 min.

Step 8 5-(4-chlorobenzyl)-6-(4-chlorophenyl)-3-(3-hydroxypropyl)-1-methylthieno[2,3-d]pyrimidine-2,4(1H,3H)-dione

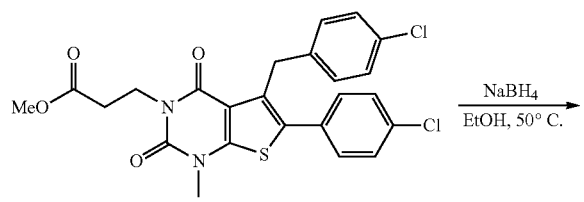

To a solution of methyl 3-(5-(4-chlorobenzyl)-6-(4-chlorophenyl)-1-methyl-2,4-dioxo-1,2-dihydrothieno[2,3-d]pyrimidin-3(4H)-yl)propanoate (13 mg, 0.0258 mmol) in EtOH (1 mL) was added NaBH₄ (2.9 mg, 0.0775 mmol). The reaction was stirred at 50° C. for 18 h, cooled to RT, quenched with aq. HCl (0.1 N, 2 mL) then concentrated to a residue which was purified by Prep HPLC to give 5-(4-chlorobenzyl)-6-(4-chlorophenyl)-3-(3-hydroxypropyl)-1-methylthieno[2,3-d]pyrimidine-2,4(1H,3H)-dione (8.6 mg, 70.1% yield) as a white solid. ¹H NMR (CD₃OD) δ: 7.43 (d, J=8.4 Hz, 2H), 7.37 (d, J=8.4 Hz, 2H), 7.19 (d, J=8.4 Hz, 2H), 7.02 (d, J=8.4 Hz, 2H) 4.32 (S, 2H), 4.05 (t, J=7.2 Hz, 2H), 3.55-3.58 (m, 5H), 1.84-1.82 (m, 2H). LCMS: MH⁺ 475 and T$_R$=3.131 min.

Compound 25

6-(4-chlorophenyl)-3-(3-hydroxypropyl)-1,5-dimethylthieno[2,3-d]pyrimidine-2,4(1H,3H)-dione

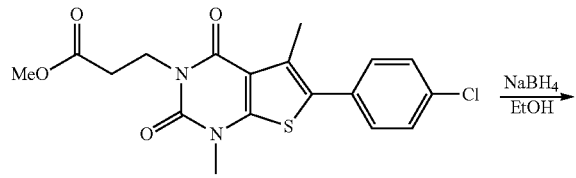

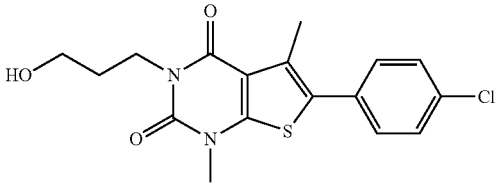

To a solution of methyl 3-(6-(4-chlorophenyl)-1,5-dimethyl-2,4-dioxo-1,2-dihydrothieno[2,3-d]pyrimidin-3(4H)-yl)propanoate (See Compound 24, Step 3, 25 mg, 0.064 mmol) in EtOH (1 mL) was added NaBH₄ (7.2 mg, 0.19 mmol). The reaction was stirred at 50° C. for 18 h, cooled to RT, quenched with diluted HCl (0.1N, 2 mL) then concentrated to a residue which was purified by Prep HPLC to give 6-(4-chlorophenyl)-3-(3-hydroxypropyl)-1,5-dimethylthieno[2,3-d]pyrimidine-2,4(1H,3H)-dione (10 mg, 43.0% yield) as a white solid. ¹H NMR (CD₃OD) δ: 7.46-7.45 (m, 4H), 4.10 (t, J=6.8 Hz, 2H), 3.62 (t, J=6.0 Hz, 2H), 3.55 (s, 3H), 2.49 (s, 3H), 1.89-1.86 (m, 2H). LCMS: MH⁺ 365 and T$_R$=2.742 min.

Compound 26

5-(4-chlorobenzyl)-3-(3-hydroxypropyl)-1-methyl-6-(3-(trifluoromethoxy)phenyl)thieno[2,3-d]pyrimidine-2,4(1H,3H)-dione

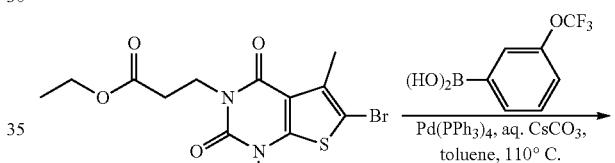

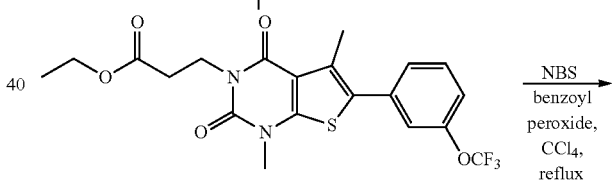

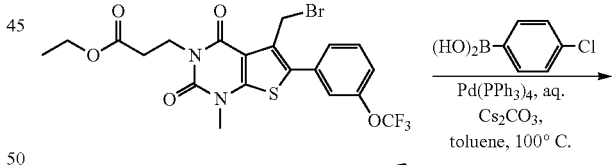

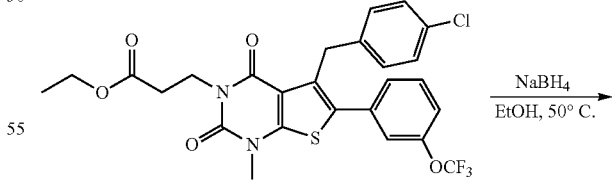

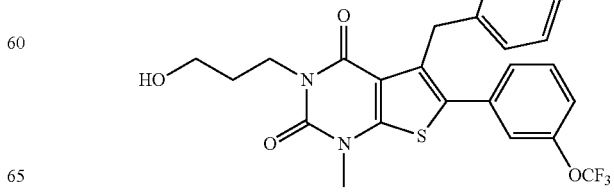

Step 1 Ethyl 3-(1,5-dimethyl-2,4-dioxo-6-(3-(trifluoromethoxy)phenyl)-1,2-dihydrothieno[2,3-d]pyrimidin-3 (4H)-yl)propanoate

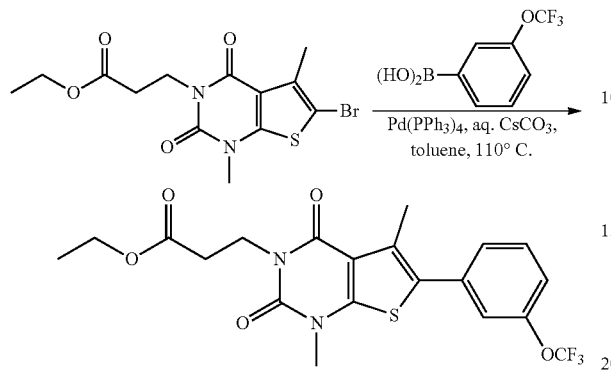

To a solution of ethyl 3-(6-bromo-1,5-dimethyl-2,4-dioxo-1,2-dihydrothieno[2,3-d]pyrimidin-3(4H)-yl)propanoate (See Compound 24, Step 4, 150 mg, 0.415 mmol) in toluene (3 mL) was added (3-(trifluoro methoxy)phenyl) boronic acid (102 mg, 0.498 mmol) and aq. $Cs_2CO_3$ solution (1 M, 0.5 mL). The reaction was degassed under nitrogen gas (3×) then $Pd(PPh_3)_4$ (24 mg) was added. The reaction was heated at 100° C. for 18 h, cooled to RT then diluted with EA (10 mL). The organic layer was washed with brine (10 mL), dried over $Na_2SO_4$ and concentrated to a residue which was purified by chromatography eluted with PE/EA (4:1) to give ethyl 3-(1,5-dimethyl-2,4-dioxo-6-(3-(trifluoromethoxy)phenyl)-1,2-dihydrothieno[2,3-d]pyrimidin-3 (4H)-yl)propanoate (120 mg, 63.8% yield) as a yellow solid. LCMS: $MH^+$ 457 and $T_R$=2.045 min.

Step 2 Ethyl 3-(5-(bromomethyl)-1-methyl-2,4-dioxo-6-(3-(trifluoromethoxy)phenyl)-1,2-dihydrothieno[2,3-d]pyrimidin-3(4H)-yl)propanoate

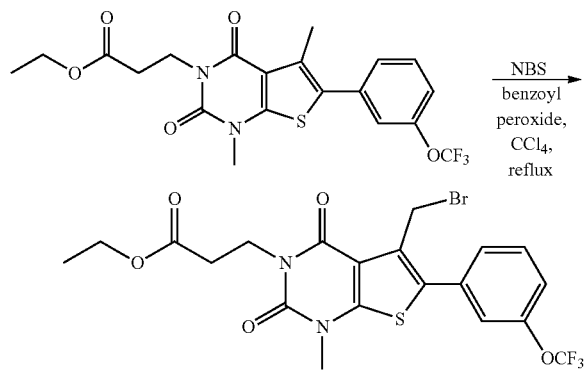

To a solution of ethyl 3-(1,5-dimethyl-2,4-dioxo-6-(3-(trifluoromethoxy)phenyl)-1,2-dihydrothieno[2,3-d]pyrimidin-3(4H)-yl)propanoate (120 mg, 0.22 mmol) in $CCl_4$ (3 mL) was added NBS (39 mg, 0.22 mmol) followed by benzoyl peroxide (5 mg). The reaction was heated at reflux for 4 h, cooled to RT and diluted with DCM (10 mL). The mixture was washed with aq. $NaHCO_3$ (10 mL), and brine (10 mL). The organic layer was dried over $Na_2SO_4$ and concentrated to give ethyl 3-(5-(bromomethyl)-1-methyl-2,4-dioxo-6-(3-(trifluoromethoxy)phenyl)-1,2-dihydrothieno[2,3-d]pyrimidin-3(4H)-yl)propanoate (100 mg, 85.7% yield) as an oil. LCMS: $MH^+$ 535 and $T_R$=2.087 min. Used without further purification.

Step 3 Ethyl 3-(5-(4-chlorobenzyl)-1-methyl-2,4-dioxo-6-(3-(trifluoromethoxy)phenyl)-1,2-dihydrothieno[2,3-d]pyrimidin-3 (4H)-yl)propanoate

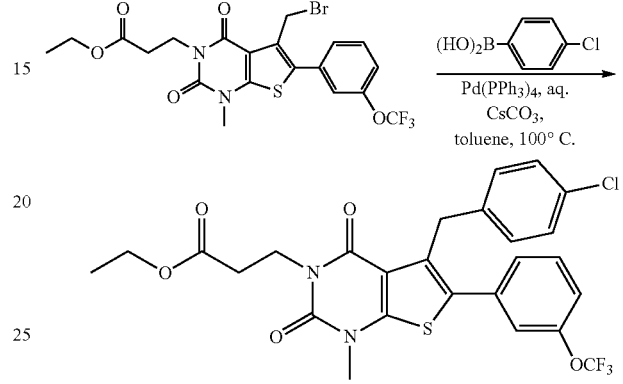

To a solution of ethyl 3-(5-(bromomethyl)-1-methyl-2,4-dioxo-6-(3-(trifluoromethoxy)phenyl)-1,2-dihydrothieno[2,3-d]pyrimidin-3(4H)-yl)propanoate (100 mg, 0.187 mmol) in toluene (5 mL) was added (4-chlorophenyl)boronic acid (32.1 mg, 0.205 mmol) and aq. $Cs_2CO_3$ (1 M, 0.28 mL). The reaction was degassed under nitrogen gas (3×) then $Pd(PPh_3)_4$ (10 mg) was added. The reaction was heated at 100° C. for 18 h, cooled to RT then diluted with EA (10 mL). The organic layer was washed with brine (5 mL), dried over $Na_2SO_4$ and concentrated to a residue which was purified by chromatography eluted with PE/EA (4:1 to 2:1) to give ethyl 3-(5-(4-chlorobenzyl)-1-methyl-2,4-dioxo-6-(3-(trifluoromethoxy)phenyl)-1,2-dihydrothieno[2,3-d]pyrimidin-3 (4H)-yl)propanoate (51 mg, 48.1% yield) as a yellow solid. LCMS: $MH^+$ 567 and $T_R$=1.710 min.

Step 4 5-(4-chlorobenzyl)-3-(3-hydroxypropyl)-1-methyl-6-(3-(trifluoromethoxy)phenyl)-thieno[2,3-d]pyrimidine-2,4(1H,3H)-dione

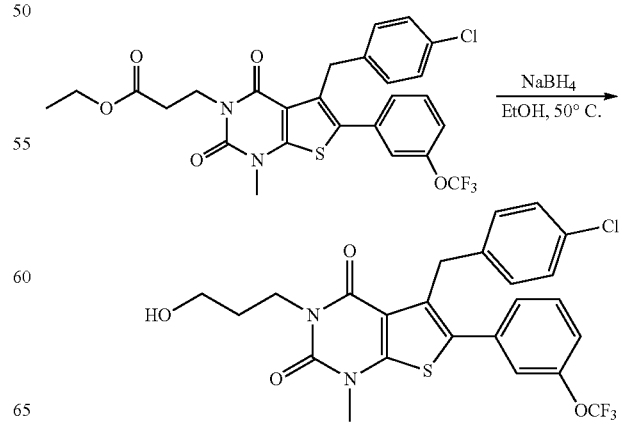

To a solution of ethyl 3-(5-(4-chlorobenzyl)-1-methyl-2,4-dioxo-6-(3-(trifluoromethoxy)phenyl)-1,2-dihydrothieno[2,3-d]pyrimidin-3(4H)-yl)propanoate (51 mg, 0.09 mmol) in EtOH (2 mL) was added NaBH₄ (10.2 mg, 0.27 mmol). The reaction was heated at 50° C. for 18 h, cooled to RT, quenched with aq. HCl (0.1N, 2 mL) then concentrated to a residue which was purified by Prep HPLC to give 5-(4-chlorobenzyl)-3-(3-hydroxypropyl)-1-methyl-6-(3-(trifluoromethoxy)phenyl) thieno[2,3-d]pyrimidine-2,4(1H,3H)-dione (8.9 mg, 29.7% yield) as a white solid. ¹H NMR (CD₃OD) δ: 7.54-7.50 (m, 1H), 7.39 (d, J=8.0 Hz, 2H), 7.31 (d, J=8.4 Hz, 2H), 7.26 (s, 1H), 7.18 (d, J=8.4 Hz, 2H), 7.01 (d, J=8.4 Hz, 2H), 4.34 (s, 2H), 4.04 (t, J=6.8 Hz, 2H), 3.58-3.55 (m, 5H), 1.84-1.80 (m, 2H). LCMS: MH⁺ 525 and $T_R$=3.382 min.

Compound 27

5-(4-chlorobenzyl)-6-(3-chlorophenyl)-3-(3-hydroxypropyl)furo[2,3-d]pyrimidine-2,4(1H,3H)-dione

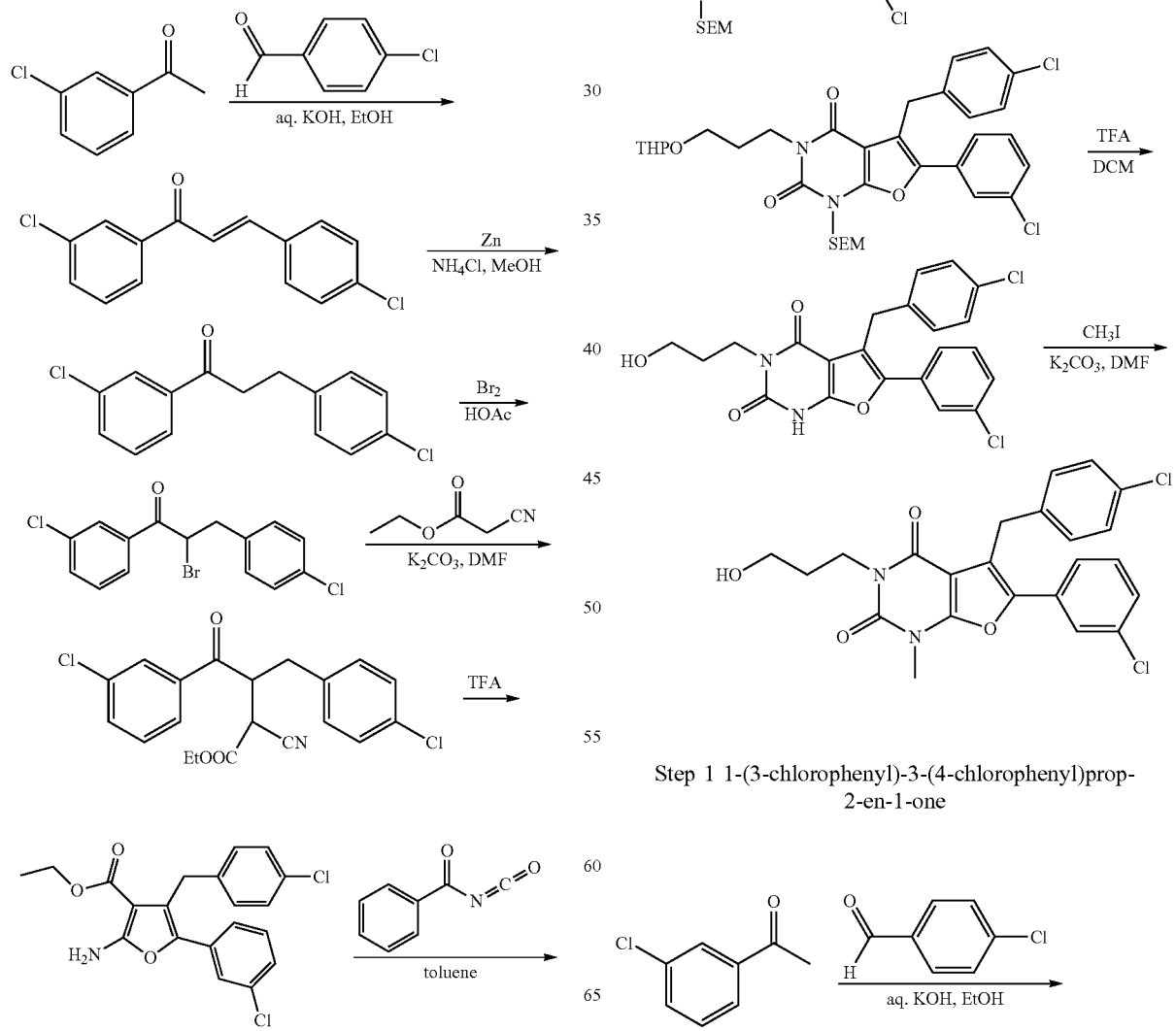

Step 1 1-(3-chlorophenyl)-3-(4-chlorophenyl)prop-2-en-1-one

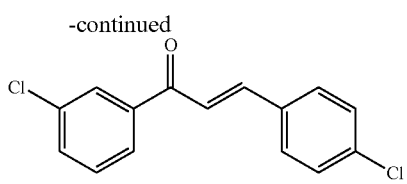

To a solution of 1-(3-chlorophenyl)ethanone (1.54 g, 10 mmol), 4-chlorobenzaldehyde (1.4 g, 10 mmol) in EtOH (25 mL) was added aq. KOH (50% wt, 10 mmol, 0.56 mL). The reaction was stirred at RT for 2 h then filtered the insoluble white solid. The solid was dried and washed with PE/EA (5:1, 10 mL) to give 1-(3-chlorophenyl)-3-(4-chlorophenyl)prop-2-en-1-one (2.3 g, 83% yield) as a white solid. LCMS: MH+ 277 and $T_R$=2.050 min. Used without further purification.

Step 2 1-(3-chlorophenyl)-3-(4-chlorophenyl)propan-1-one

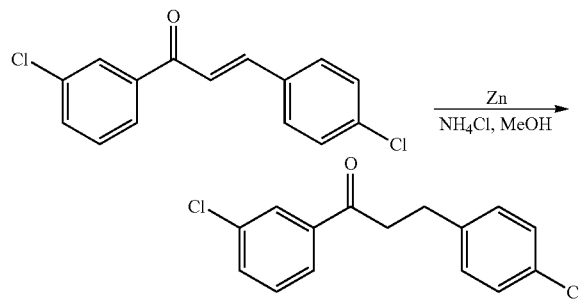

1-(3-chlorophenyl)-3-(4-chlorophenyl)prop-2-en-1-one (1.38 g, 5 mmol), Zn dust (1.95 g, 30 mmol), NH4Cl (2.67 g, 50 mmol) were combined in MeOH (10 mL) and water (5 mL). The reaction was refluxed for 4 h, cooled to RT then filtered. The filtrate was concentrated to a residue which was purified by chromatography PE/EA (5:1) to give 1-(3-chlorophenyl)-3-(4-chlorophenyl)propan-1-one (1.15 g, 83% yield) as a brown solid. MH+ 279 and $T_R$=2.025 min.

Step 3 2-bromo-1-(3-chlorophenyl)-3-(4-chlorophenyl)propan-1-one

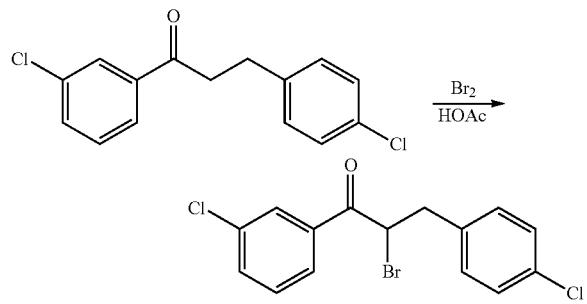

To a solution of 1-(3-chlorophenyl)-3-(4-chlorophenyl)propan-1-one (1.39 g, 5 mmol) in HOAc (15 mL) at 0° C. was added Br2 (800 mg, 5 mmol) dropwise. The reaction was refluxed for 8 h, cooled to RT, concentrated then diluted with EA (25 mL) and water (5 mL). The organic layer was washed with brine (5 mL), dried over Na2SO4 and concentrated to give a residue which was purified by chromatography eluted with PE/EA (50:1) to give 2-bromo-1-(3-chlorophenyl)-3-(4-chlorophenyl)propan-1-one (358 mg, 20% yield) as a brown solid. LCMS: MH+ 359 and $T_R$=2.029 min.

Step 4 ethyl 3-(4-chlorobenzyl)-4-(3-chlorophenyl)-2-cyano-4-oxobutanoate

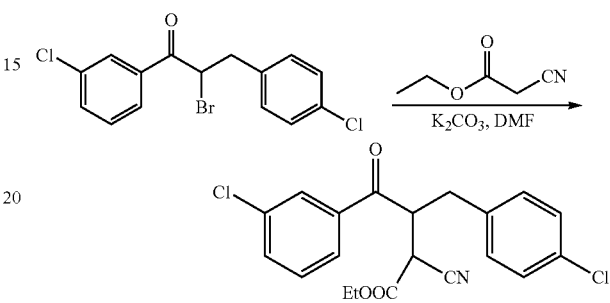

To a solution of 2-bromo-1-(3-chlorophenyl)-3-(4-chlorophenyl)propan-1-one (358 mg, 1 mmol) in DMF (3 mL) was added ethyl 2-cyanoacetate (226 mg, 2 mmol), followed by K2CO3 (276 mg, 2 mmol). The reaction was stirred at RT for 2 h then diluted with EA (10 mL) and water (3 mL). The organic layer was washed with brine (3 mL), dried over Na2SO4 and concentrated to give ethyl 3-(4-chlorobenzyl)-4-(3-chlorophenyl)-2-cyano-4-oxobutanoate (300 mg, 77% yield) as a yellow solid. LCMS: MH+ 390 and $T_R$=2.334 min. Used without further purification.

Step 5 Ethyl 2-amino-4-(4-chlorobenzyl)-5-(3-chlorophenyl)furan-3-carboxylate

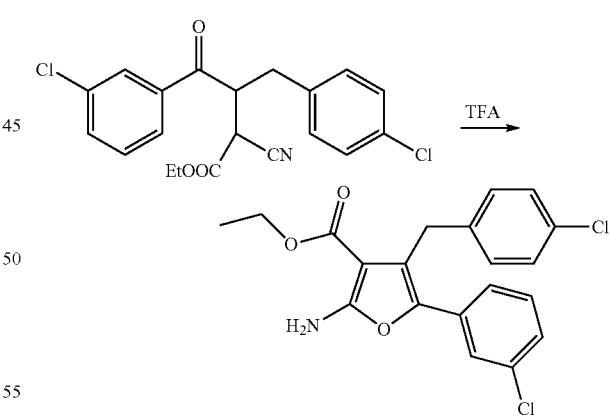

A solution of ethyl 3-(4-chlorobenzyl)-4-(3-chlorophenyl)-2-cyano-4-oxobutanoate (1.945 g, 5 mmol) in TFA (20 mL) was stirred at 100° C. for 3 h. The reaction was cooled to RT and concentrated to a residue which was diluted with EA (40 mL) and water (8 mL). The organic layer was dried over Na2SO4 and concentrated to a residue which was purified by chromatography eluted with PE/EA (5:1) to give ethyl 2-amino-4-(4-chlorobenzyl)-5-(3-chlorophenyl)furan-3-carboxylate (1.4 g, 72% yield) as a white solid. LCMS: MH+ 390 and $T_R$=2.503 min.

Step 6 Ethyl 2-(3-benzoylureido)-4-(4-chlorobenzyl)-5-(3-chlorophenyl)furan-3-carboxylate

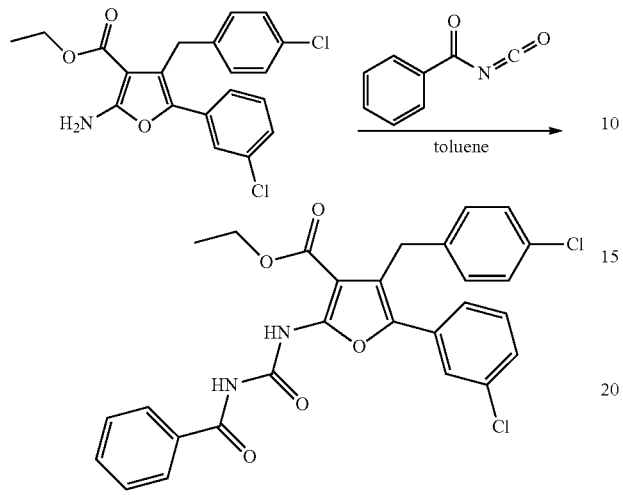

To a solution of ethyl 2-amino-4-(4-chlorobenzyl)-5-(3-chlorophenyl)furan-3-carboxylate (38.9 mg, 0.1 mmol) in toluene (5 mL) was added benzoyl isocyanate (14.7 mg, 0.1 mmol). The reaction was stirred at RT for 2 h then diluted with EA (5 mL) and water (2 mL). The organic layer was dried over $Na_2SO_4$ and concentrated to a residue which was purified by Prep HPLC to give ethyl 2-(3-benzoylureido)-4-(4-chlorobenzyl)-5-(3-chlorophenyl)furan-3-carboxylate (12 mg, 22% yield) as a white solid. $^1$H NMR (DMSO-$d_6$) δ: 12.41 (s, 1H), 11.51 (s, 1H), 8.10 (d, J=7.4 Hz, 2H), 7.75 (t, J=7.5 Hz, 1H), 7.63 (t, J=7.7 Hz, 2H), 7.60-7.51 (m, 3H), 7.48 (d, J=6.9 Hz, 1H), 7.42 (d, J=8.5 Hz, 2H), 7.27 (d, J=8.3 Hz, 2H), 4.34 (s, 2H), 4.28 (q, J=7.1 Hz, 2H), 1.23 (t, J=7.1 Hz, 3H). LCMS: MH$^+$ 537 and $T_R$=2.962 min.

Step 7 5-(4-chlorobenzyl)-6-(3-chlorophenyl)furo[2,3-d]pyrimidine-2,4(1H,3H)-dione

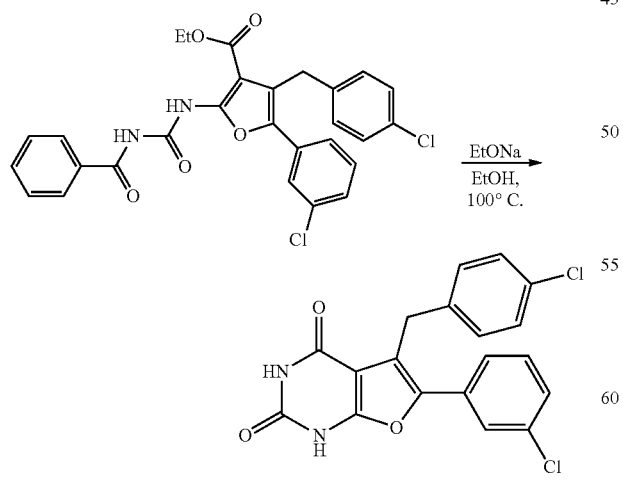

To a solution of ethyl 2-(3-benzoylureido)-4-(4-chlorobenzyl)-5-(3-chlorophenyl)furan-3-carboxylate (53.6 mg, 0.1 mmol) in EtOH (2 mL) was added sodium ethoxide (13.6 mg, 0.2 mmol). The reaction was heated at 100° C. (MW) for 20 min, cooled to RT and quenched with aq. NH$_4$Cl (2 mL). The reaction was concentrated to a residue which was diluted with water (3 mL) and extracted with EA (3×8 mL). The combined organic layers were dried over $Na_2SO_4$ and concentrated to give 5-(4-chlorobenzyl)-6-(3-chloro phenyl) furo[2,3-d]pyrimidine-2,4(1H,3H)-dione (2.3 g, 83% yield) as a white solid. $^1$H NMR (DMSO-$d_6$) δ: 9.70 (brd s, 1H), 7.38 (m, 3H), 7.33 (d, J=8.5 Hz, 2H), 7.30-7.21 (m, 3H), 4.24 (s, 2H). LCMS: MH$^+$ 387 and $T_R$=2.685 min. Used without further purification.

Step 8 5-(4-chlorobenzyl)-6-(3-chlorophenyl)-1-((2-(trimethylsilyl)ethoxy)methyl)furo[2,3-d]pyrimidine-2,4(1H,3H)-dione

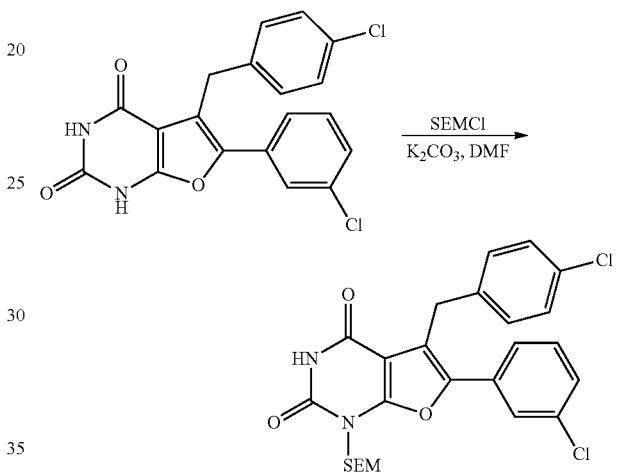

To a mixture of 5-(4-chlorobenzyl)-6-(3-chlorophenyl) furo[2,3-d]pyrimidine-2,4(1H,3H)-dione (38.7 mg, 0.1 mmol) and $K_2CO_3$ (13.8 mg, 0.1 mmol) in DMF (1 mL) at 0° C. was added chloromethyl-2-trimethylsilylethyl ether (33.4 mg, 0.2 mmol). The reaction was stirred at 0° C. for 1 h then diluted with EA (10 mL) and water (3 mL). The organic layer was washed with brine (3 mL), dried over $Na_2SO_4$ and concentrated to a residue which was purified by chromatography eluted with PE/EA (5:1) to give 5-(4-chlorobenzyl)-6-(3-chlorophenyl)-1-((2-(trimethylsilyl)ethoxy)methyl)furo[2,3-d]pyrimidine-2,4(1H,3H)-dione (31 mg, 60.7% yield) as a colorless oil. LCMS: MH$^+$ 517 and $T_R$=2.196 min.

Step 9 5-(4-chlorobenzyl)-6-(3-chlorophenyl)-3-(3-(tetrahydro-2H-pyran-2-yloxy)propyl)-1-((2-(trimethylsilyl)ethoxy)methyl)furo[2,3-d]pyrimidine-2,4(1H,3H)-dione

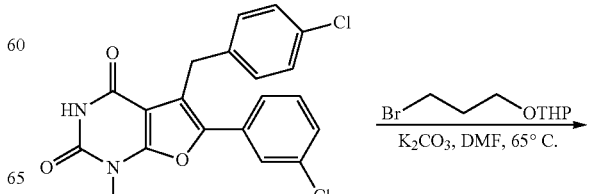

-continued

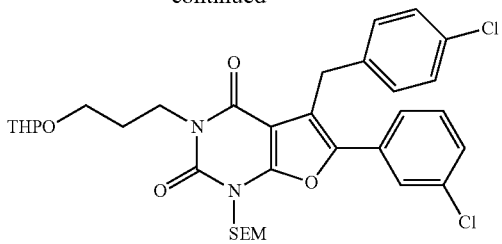

To a solution of 5-(4-chlorobenzyl)-6-(3-chlorophenyl)-1-((2-(trimethylsilyl)ethoxy)methyl)furo[2,3-d]pyrimidine-2,4(1H,3H)-dione (25.88 mg, 0.01 mmol) in DMF (3 mL) was added 2-(3-bromopropoxy)tetrahydro-2H-pyran (11.2 mg, 0.05 mmol) and K$_2$CO$_3$ (6.9 mg, 0.05 mmol). The reaction was stirred at 60° C. for 2 h, cooled to RT, then was diluted with EA (12 mL) and water (4 mL). The organic layer was washed with brine (3 mL), dried over Na$_2$SO$_4$, and concentrated to a residue which was purified by chromatography PE/EA (5:1) to give 5-(4-chlorobenzyl)-6-(3-chlorophenyl)-3-(3-(tetrahydro-2H-pyran-2-yloxy)propyl)-1-((2-(trimethylsilyl)ethoxy)methyl) furo[2,3-d]pyrimidine-2,4 (1H,3H)-dione (10 mg, 30.7% yield) as an oil. LCMS: (M$^+$+Na) 681 and T$_R$=2.289 min.

Step 10 5-(4-chlorobenzyl)-6-(3-chlorophenyl)-3-(3-hydroxypropyl)furo[2,3-d]pyrimidine-2,4(1H,3H)-dione

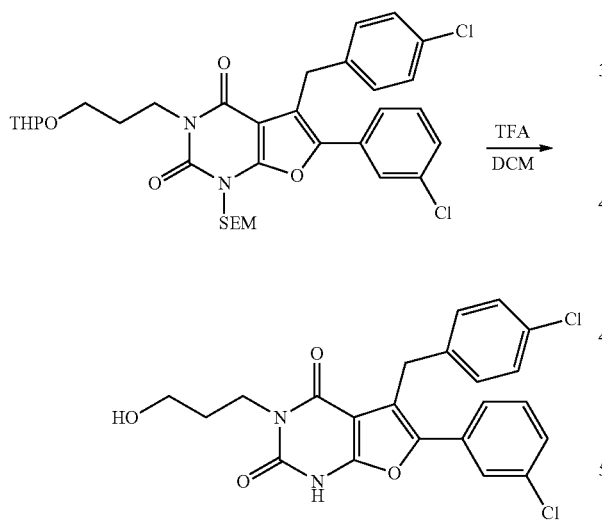

To a solution of 5-(4-chlorobenzyl)-6-(3-chlorophenyl)-3-(3-(tetrahydro-2H-pyran-2-yloxy) propyl)-1-((2-(trimethylsilyl)ethoxy)methyl)furo[2,3-d]pyrimidine-2,4(1H,3H)-dione (20 mg, 0.03 mmol) in DCM (0.8 mL) was added in TFA (0.8 mL). The reaction was stirred at RT for 2 h then diluted with DCM (5 mL) and water (2 mL). The organic layer was dried over Na$_2$SO$_4$ and concentrated to a residue which was purified by Prep HPLC to give 5-(4-chlorobenzyl)-6-(3-chlorophenyl)-3-(3-hydroxypropyl)furo[2,3-d]pyrimidine-2,4(1H,3H)-dione (3 mg, 23% yield) as an oil. $^1$H NMR (DMSO-d$_6$) δ: 7.43 (d, J=3.4 Hz, 3H), 7.34 (d, J=8.4 Hz, 3H), 7.26 (d, J=8.4 Hz, 2H), 4.53 (s, 1H), 4.28 (s, 2H), 3.85 (t, J=7.1 Hz, 2H), 3.40 (s, 2H), 1.71-1.58 (m, 2H). LCMS: MH$^+$ 445 and T$_R$=2.803 min.

Step 11 5-(4-chlorobenzyl)-6-(3-chlorophenyl)-3-(3-hydroxypropyl)-1-methylfuro[2,3-d]pyrimidine-2,4 (1H,3H)-dione

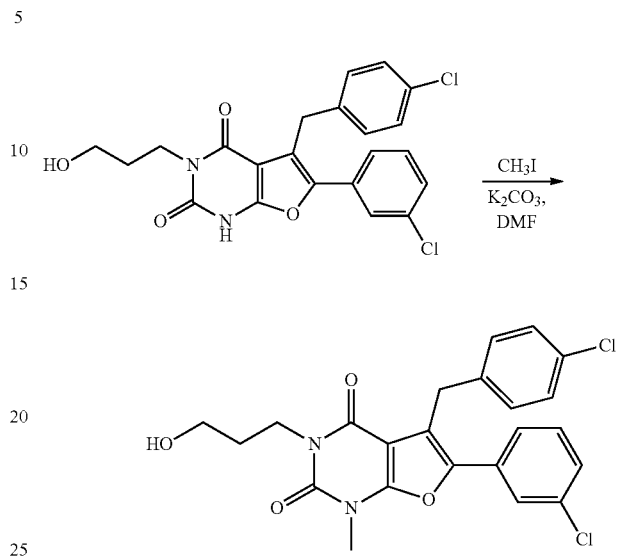

To a mixture of 5-(4-chlorobenzyl)-6-(3-chlorophenyl)-3-(3-hydroxypropyl)furo[2,3-d]pyrimidine-2,4(1H,3H)-dione (22.25 mg, 0.05 mmol), K$_2$CO$_3$ (13.8 mg, 0.1 mmol) in DMF (1 mL) was added CH$_3$I (8.5 mg, 0.06 mmol). The reaction was heated in a sealed tube at 65° C. for 2 h, cooled to RT then diluted with EA (10 mL) and water (3 mL). The organic layer was washed with brine (3 mL) dried over Na$_2$SO$_4$ and concentrated to a residue which was purified by Prep HPLC to give 5-(4-chlorobenzyl)-6-(3-chlorophenyl)-3-(3-hydroxypropyl)-1-methylfuro[2,3-d]pyrimidine-2,4 (1H,3H)-dione (3 mg, 13% yield) as a white solid. $^1$H NMR (DMSO-d$_6$) δ: 7.62 (s, 1H), 7.54 (d, J=8.0 Hz, 1H), 7.47 (t, J=7.9 Hz, 1H), 7.41 (d, J=8.0 Hz, 1H), 7.35 (d, J=8.5 Hz, 2H), 7.26 (d, J=8.5 Hz, 2H), 4.47 (t, J=5.2 Hz, 1H), 4.32 (s, 2H), 3.97-3.81 (m, 2H), 3.53 (s, 3H), 3.43 (dd, J=11.8, 6.4 Hz, 2H), 1.75-1.60 (m, 2H). LCMS: MH$^+$ 459 and T$_R$=3.047 min.

Compound 28

5-(4-chlorobenzyl)-6-(3-chlorophenyl)-1,3-bis(3-hydroxypropyl)furo[2,3-d]pyrimidine-2,4(1H,3H)-dione

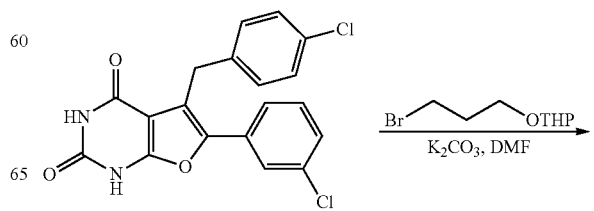

-continued

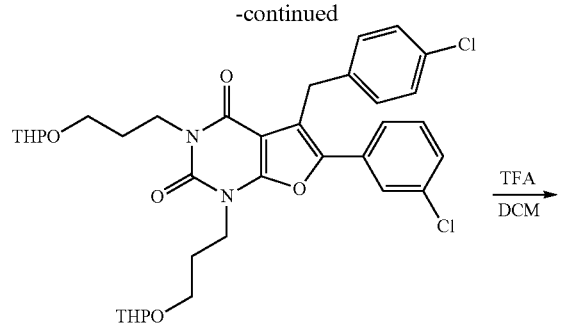

Step 1 5-(4-chlorobenzyl)-6-(3-chlorophenyl)-1,3-bis(3-(tetrahydro-2H-pyran-2-yloxy)propyl)furo[2,3-d]pyrimidine-2,4(1H,3H)-dione

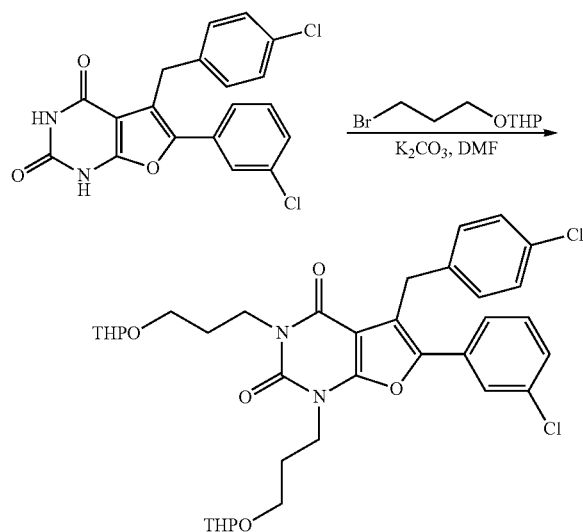

To a solution of 5-(4-chlorobenzyl)-6-(3-chlorophenyl)-1,3-bis(3-hydroxypropyl)furo[2,3-d]-pyrimidine-2,4(1H,3H)-dione (Compound 27, Step 7, 77.4 mg, 0.2 mmol) in DMF (4 mL) was added 2-(3-bromo propoxy)tetrahydro-2H-pyran (88.8 mg, 0.4 mmol) and K$_2$CO$_3$ (55.2 mg, 0.24 mmol). The reaction was stirred at RT for 2 h then diluted with EA (10 mL) and water (3 mL). The organic layer was washed with brine (3 mL), dried over Na$_2$SO$_4$ and concentrated to give 5-(4-chlorobenzyl)-6-(3-chlorophenyl)-1,3-bis(3-(tetrahydro-2H-pyran-2-yloxy)propyl)furo[2,3-d]pyrimi-dine-2,4(1H,3H)-dione (86.4 mg, 64% yield) as a yellow solid. LCMS: MH$^+$ 671 and T$_R$=2.435 min. Used without further purification.

Step 2 5-(4-chlorobenzyl)-6-(3-chlorophenyl)-1,3-bis(3-hydroxypropyl)furo[2,3-d]pyrimidine-2,4(1H, 3H)-dione

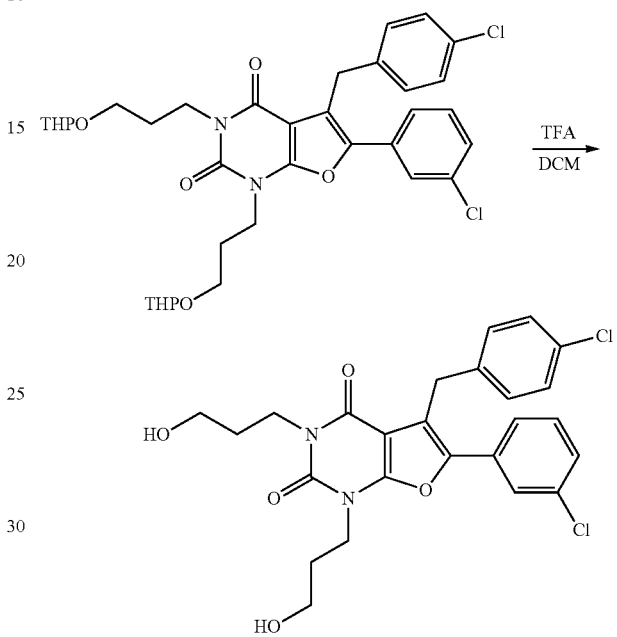

To a solution of 5-(4-chlorobenzyl)-6-(3-chlorophenyl)-1,3-bis(3-(tetrahydro-2H-pyran-2-yl oxy) propyl)furo[2,3-d]pyrimidine-2,4(1H,3H)-dione (67 mg, 0.1 mmol) in DCM (5 mL) was added TFA (1 mL). The reaction was stirred at RT for 1 h then concentrated to a residue which was diluted with EA (10 mL) and water (2 mL). The organic layer was dried over Na$_2$SO$_4$ and concentrated to a residue which was purified by Prep HPLC to give 5-(4-chlorobenzyl)-6-(3-chlorophenyl)-1,3-bis(3-hydroxypropyl)furo[2,3-d]pyrimi-dine-2,4(1H,3H)-dione (29 mg, 58% yield) as an oil. $^1$H NMR (DMSO-d$_6$) δ: 7.61 (s, 1H), 7.54 (d, J=7.7 Hz, 1H), 7.42 (t, J=7.9 Hz, 1H), 7.36 (d, J=8.2 Hz, 1H), 7.28 (s, 4H), 4.35 (s, 2H), 4.29 (t, J=6.9 Hz, 2H), 4.09 (t, J=7.1 Hz, 2H), 3.71 (t, J=5.9 Hz, 2H), 3.62 (t, J=6.3 Hz, 2H), 2.16-2.02 (m, 2H), 1.94-1.80 (m, 2H). LCMS: MH$^+$ 503 and T$_R$=2.826 min.

INCORPORATION BY REFERENCE

All publications and patents mentioned herein, are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A compound of Formula (I)

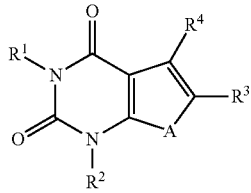

Formula (I)

or a pharmaceutically acceptable salt thereof, wherein:

A is S or O;

$R^1$ is $C_2$-$C_{10}$ hydroxyalkyl, wherein one or more carbon atom of the alkyl portion of the hydroxylalkyl group is optionally substituted with 1-3 $R^5$;

$R^2$ is $C_1$-$C_4$ alkyl or $C_1$-$C_4$ hydroxyalkyl;

$R^3$ is $C_1$-$C_6$ alkyl, $C_2$-$C_6$ alkenyl, $C_2$-$C_6$ alkynyl, $C_1$-$C_6$ acyl, $C_3$-$C_{10}$ cycloalkyl, $C_1$-$C_6$ alkoxy, $C_4$-$C_{10}$ cycloalkyloxy, halo, hydroxyl, alkylthio, thionyl, sulfonyl, sulfonamidyl, $C_6$-$C_{12}$ aryl, 5-14-membered heteroaryl, $C_6$-$C_{12}$ aryl-$C_1$-$C_6$ alkyl, 5-14-membered heteroaryl-$C_1$-$C_6$ alkyl, $C_6$-$C_{12}$ aryloxy, —O—$C_6$-$C_{12}$ aryl-$C_1$-$C_6$ alkyl, —O—$C_1$-$C_6$ alkyl-$C_6$-$C_{12}$ aryl, 5-14-membered heteroaryloxy, 3-18-membered heterocycloalkyl, amino, $C_1$-$C_6$ alkylamino, $C_2$-$C_{12}$ dialkylamino, —C(O)NH—$R^5$, —C(O)N—($C_1$-$C_6$ alkyl)-$R^5$, —NHC(O)—$R^5$, —N—($C_1$-$C_6$ alkyl)-C(O)—$R^5$, urea, sulfonylurea, nitro, or cyano, wherein each alkyl, alkenyl, alkynyl, acyl, cycloalkyl, alkoxy, cycloalkyloxy, alkylthio, aryl, heteroaryl, aryloxy, heteroaryloxy, and heterocycloalkyl represented by $R^3$ is optionally and independently substituted with 1-4 $R^5$;

$R^4$ is $C_1$-$C_6$ alkyl, $C_2$-$C_6$ alkenyl, $C_2$-$C_6$ alkynyl, $C_1$-$C_6$ acyl, $C_3$-$C_{10}$ cycloalkyl, $C_1$-$C_6$ alkoxy, $C_4$-$C_{10}$ cycloalkyloxy, halo, hydroxyl, alkylthio, thionyl, sulfonyl, sulfonamidyl, $C_6$-$C_{12}$ aryl, 5-14-membered heteroaryl, $C_6$-$C_{12}$ aryl-$C_1$-$C_6$ alkyl, 5-14-membered heteroaryl-$C_1$-$C_6$ alkyl, $C_6$-$C_{12}$ aryloxy, —O—$C_6$-$C_{12}$ aryl-$C_1$-$C_6$ alkyl, —O—$C_1$-$C_6$ alkyl-$C_6$-$C_{12}$ aryl, 5-14-membered heteroaryl-$C_1$-$C_6$ alkyl, 5-14-membered heteroaryloxy, 3-18-membered heterocycloalkyl, amino, $C_1$-$C_6$ alkylamino, $C_2$-$C_{12}$ dialkylamino, —C(O)NH—$R^5$, —C(O)N—($C_1$-$C_6$ alkyl)-$R^5$, —NHC(O)—$R^5$, —N—($C_1$-$C_6$ alkyl)C(O)—$R^5$, urea, sulfonylurea, nitro, or cyano, wherein each alkyl, alkenyl, alkynyl, acyl, cycloalkyl, alkoxy, cycloalkyloxy, alkylthio, aryl, heteroaryl, aryloxy, heteroaryloxy, and heterocycloalkyl represented by $R^4$ is optionally and independently substituted with 1-4 $R^5$;

each $R^5$ is independently $C_1$-$C_6$ alkyl, $C_2$-$C_6$ alkenyl, $C_2$-$C_6$ alkynyl, $C_1$-$C_6$ acyl, $C_3$-$C_{10}$ cycloalkyl, $C_1$-$C_6$ alkoxy, $C_4$-$C_{10}$ cycloalkyloxy, halo, hydroxyl, alkylthio, thionyl, sulfonyl, sulfonamidyl, amino, $C_1$-$C_6$ alkylamino, $C_2$-$C_{12}$ dialkylamino, —C(O)NH—$R^6$, —C(O)N—($C_1$-$C_6$ alkyl)-$R^6$, —NHC(O)—$R^6$, —N—($C_1$-$C_6$ alkyl)C(O)—$R^6$, urea, sulfonylurea, nitro, or cyano, wherein each alkyl, alkenyl, alkynyl, acyl, cycloalkyl, alkoxy, cycloalkoxy, and alkylthio represented by $R^5$ is optionally and independently substituted with 1-5 $R^6$; and each $R^6$ is independently $C_1$-$C_6$ alkyl, $C_2$-$C_6$ alkenyl, $C_2$-$C_6$ alkynyl, $C_1$-$C_6$ acyl, $C_1$-$C_6$ alkoxy, halo, $C_1$-$C_6$ haloalkyl, $C_1$-$C_6$ haloalkoxy, hydroxyl, amino, —C(O) $NH_2$, —C(O)NH$C_1$-$C_6$ alkyl, —NHC(O)($C_1$-$C_6$ alkyl), —N—($C_1$-$C_6$ alkyl)C(O)($C_1$-$C_6$ alkyl), nitro, or cyano.

2. The compound of claim 1, wherein $R^1$ is an unsubstituted $C_2$-$C_6$ hydroxyalkyl; or a pharmaceutically acceptable salt thereof.

3. The compound according to claim 1, wherein $R^1$ is 3-hydroxypropyl; or a pharmaceutically acceptable salt thereof.

4. The compound according to claim 1, wherein $R^2$ is methyl or 3-hydroxypropyl; or a pharmaceutically acceptable salt thereof.

5. The compound according to claim 1, wherein A is O; or a pharmaceutically acceptable salt thereof.

6. The compound according to claim 1, wherein A is S; or a pharmaceutically acceptable salt thereof.

7. The compound according to claim 1, wherein $R^3$ is $C_2$-$C_4$ alkyl, phenyl, pyridyl, or phenoxy, which the latter three groups are optionally substituted with one or more substituents selected from phenyl, halogen or —OCF$_3$; or a pharmaceutically acceptable salt thereof.

8. The compound according to claim 1, wherein $R^4$ is $C_1$-$C_5$ alkyl, $C_2$-$C_5$ acyl, or benzyl, each group optionally substituted with one or more methyl, hydroxyl, or halo; or a pharmaceutically acceptable salt thereof.

9. The compound accordingly to claim 1, wherein $R^3$ is

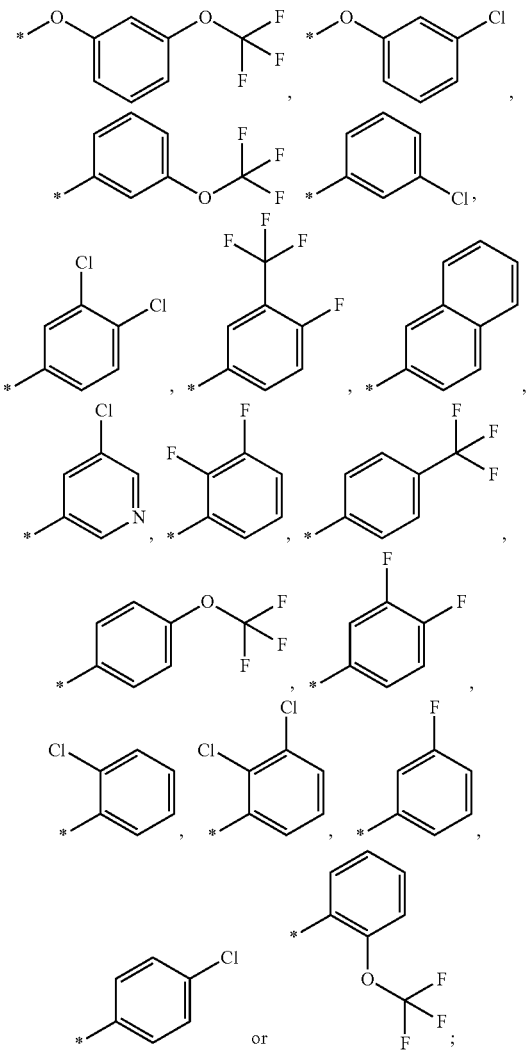

or pharmaceutically acceptable salt thereof.

10. The compound accordingly to claim 1, wherein $R^4$ is methyl,

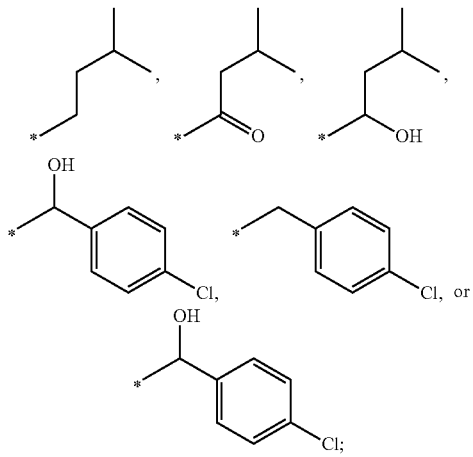

or a pharmaceutically acceptable salt thereof.

11. The compound according to claim 1, namely a compound of formula Ia or Ib

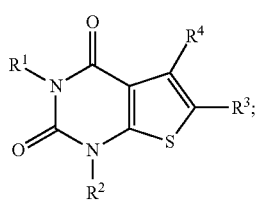

Ia

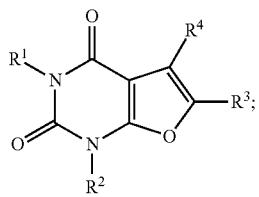

Ib in which
  $R^1$ is 3-hydroxypropyl;
  $R^2$ is methyl or 3-hydroxypropyl;
  $R^3$ is

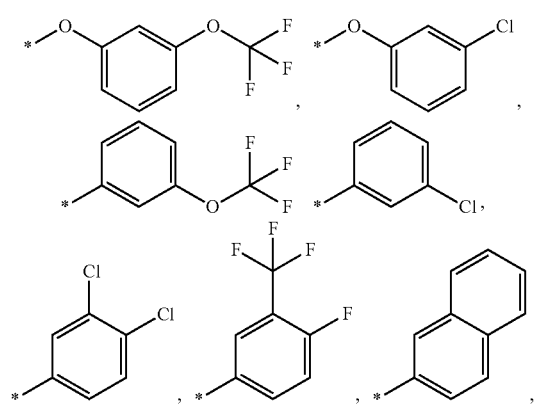

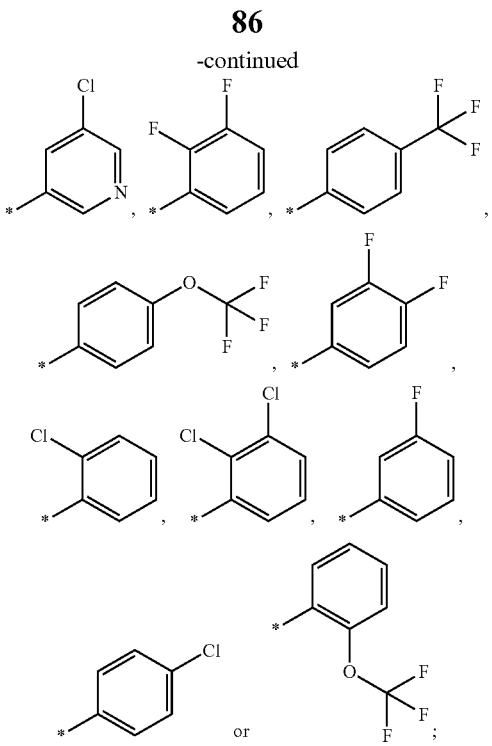

and
  $R^4$ is methyl,

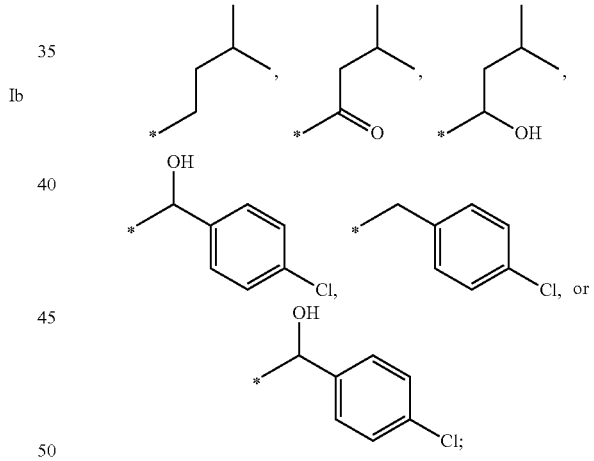

or a pharmaceutically acceptable salt thereof.

12. The compound of claim 1, wherein the compound is selected from the group consisting of:

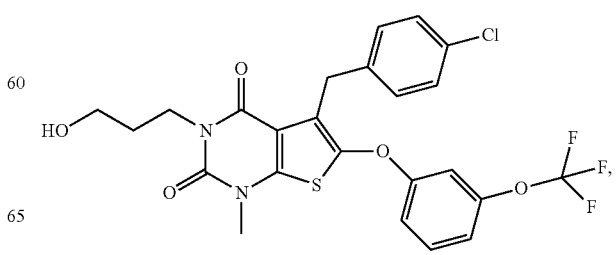

87
-continued
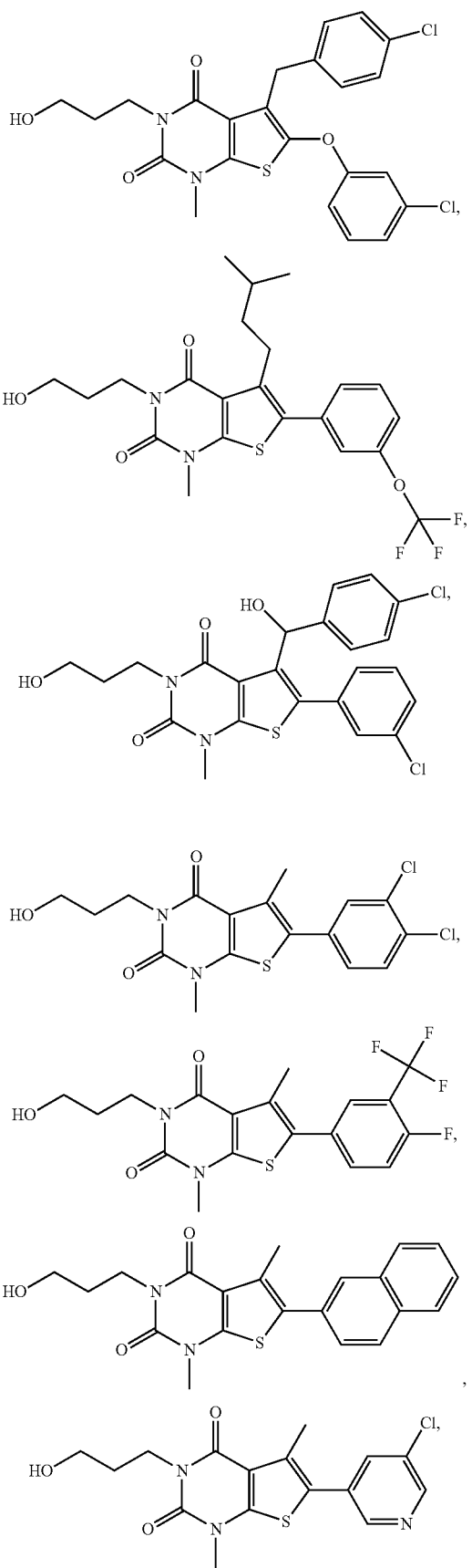
88
-continued
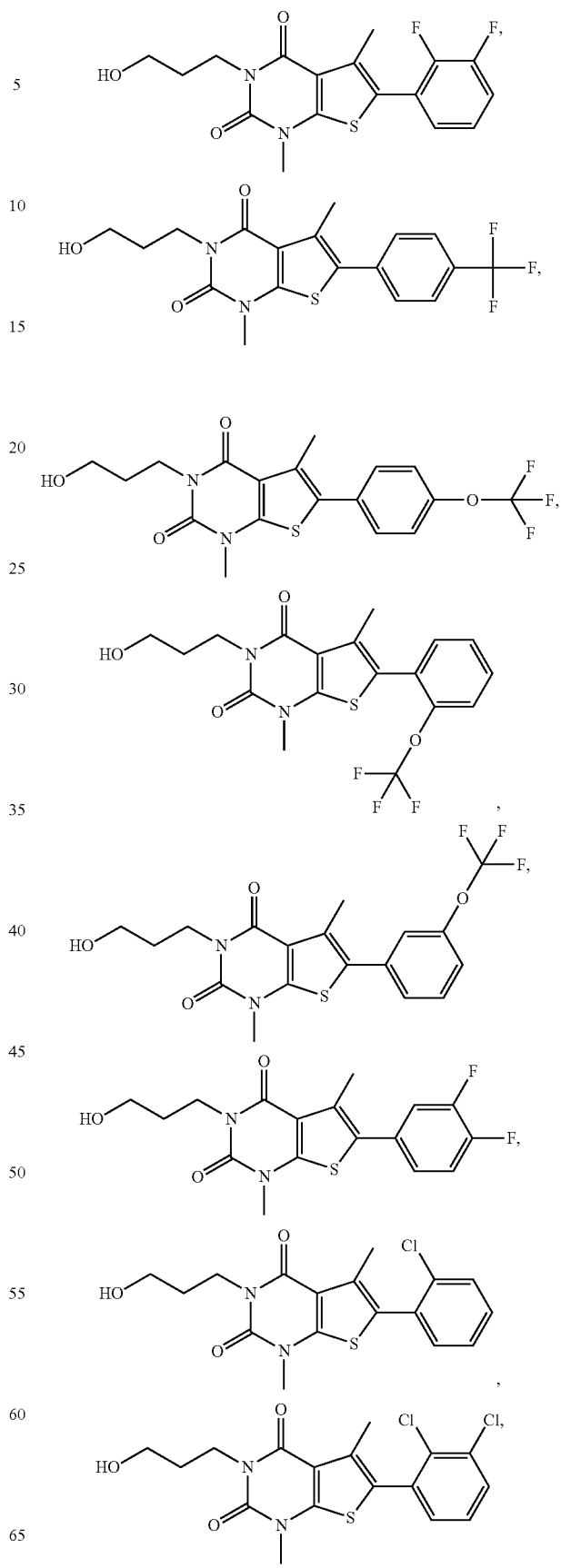

-continued

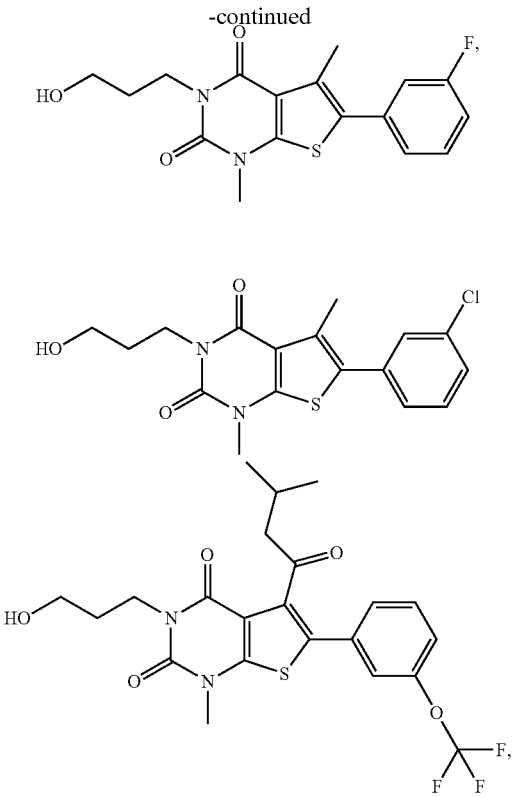

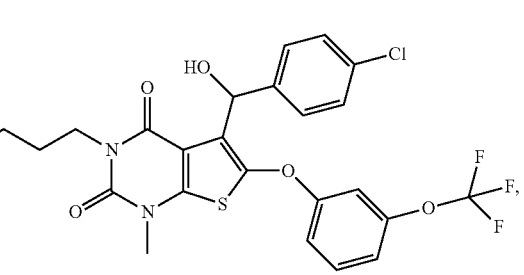

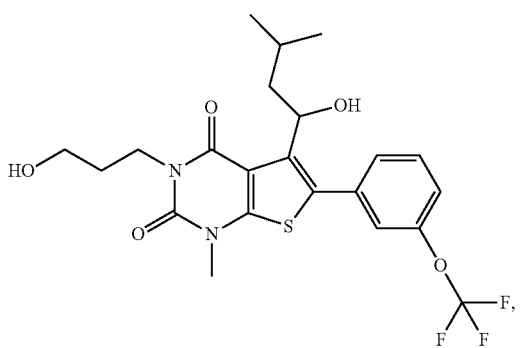

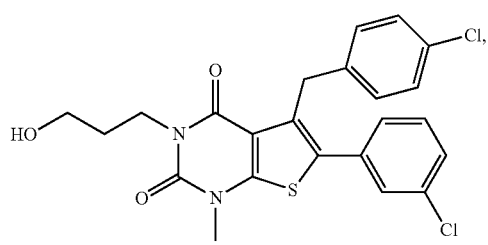

-continued

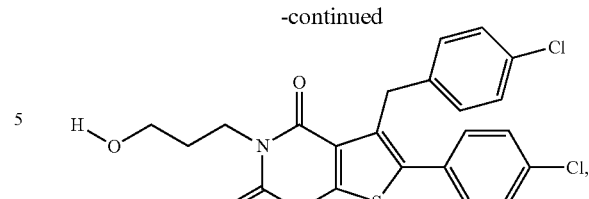

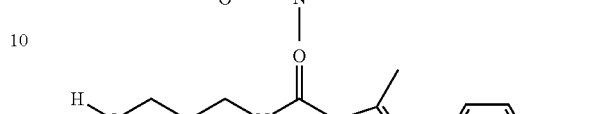

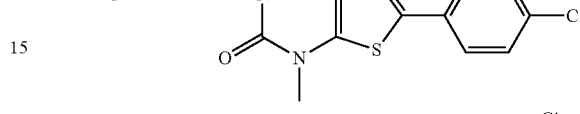

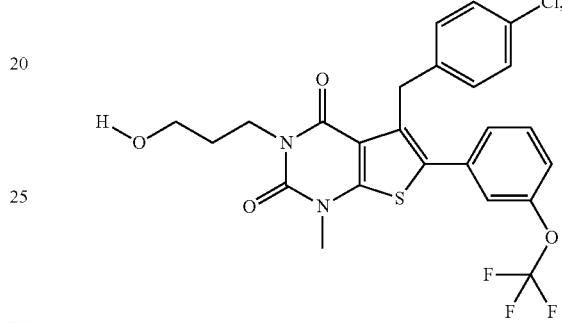

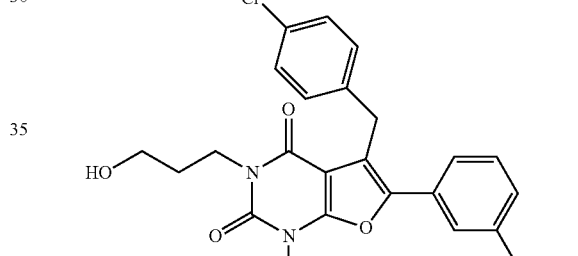

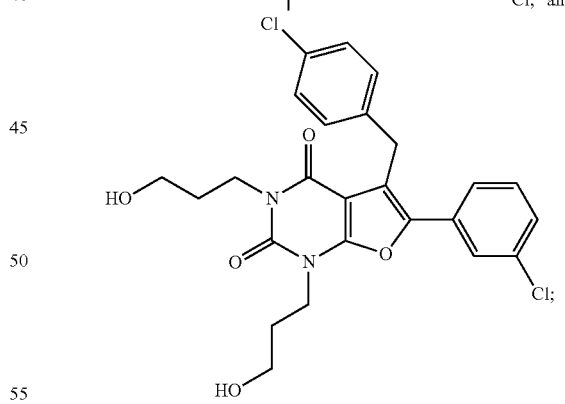

or a pharmaceutically acceptable salt thereof.

13. A pharmaceutical composition comprising at least one compound according to claim 1, or a pharmaceutically acceptable salt thereof, in a mixture with a pharmaceutically acceptable excipient, diluent or carrier.

14. A method of inhibiting TRPC5 comprising contacting a cell with the compound according to claim 1, or a pharmaceutically acceptable salt thereof.

15. The method of treating a TRPC5 mediated disorder in a subject in need thereof, comprising administering an effective amount of a compound according to claim 1, or a pharmaceutically acceptable salt thereof, to the subject, wherein the TRPC5 mediated disorder is selected from the group consisting of: depression, anxiety disorders, Alzheimers disease, Parkinson's disease, Huntingtons disease, ALS, proteinuric kidney disease and seizure disorder.

* * * * *